(12) United States Patent
Himmler

(10) Patent No.: US 10,059,777 B2
(45) Date of Patent: Aug. 28, 2018

(54) SECRETORY IMMUNOGLOBULIN COMPLEX

(71) Applicant: Gottfried Himmler, Vienna (AT)

(72) Inventor: Gottfried Himmler, Vienna (AT)

( * ) Notice: Subject to any disclaimer, the term of this patent is extended or adjusted under 35 U.S.C. 154(b) by 725 days.

(21) Appl. No.: 14/390,755

(22) PCT Filed: Apr. 5, 2013

(86) PCT No.: PCT/EP2013/057201
§ 371 (c)(1),
(2) Date: Oct. 3, 2014

(87) PCT Pub. No.: WO2013/150138
PCT Pub. Date: Oct. 10, 2013

(65) Prior Publication Data
US 2015/0166679 A1    Jun. 18, 2015

(30) Foreign Application Priority Data
Apr. 5, 2012 (EP) .................... 12163439

(51) Int. Cl.
| C07K 16/44 | (2006.01) |
|---|---|
| C07K 16/04 | (2006.01) |
| C07K 16/12 | (2006.01) |
| C07K 16/30 | (2006.01) |
| A61K 39/00 | (2006.01) |
| A61K 38/00 | (2006.01) |

(52) U.S. Cl.
CPC .............. *C07K 16/44* (2013.01); *C07K 16/04* (2013.01); *C07K 16/1282* (2013.01); *C07K 16/3076* (2013.01); *A61K 38/00* (2013.01); *A61K 2039/541* (2013.01); *C07K 2317/14* (2013.01); *C07K 2317/30* (2013.01); *C07K 2317/31* (2013.01); *C07K 2317/40* (2013.01); *C07K 2317/41* (2013.01); *C07K 2319/036* (2013.01)

(58) Field of Classification Search
None
See application file for complete search history.

(56) References Cited

U.S. PATENT DOCUMENTS

| 5,846,569 | A * | 12/1998 | Anderson | ............... | A61K 35/20 424/157.1 |
|---|---|---|---|---|---|
| 6,046,037 | A | 4/2000 | Hiatt et al. | | |
| 6,300,104 | B1 * | 10/2001 | Morrison | ......... | A61K 39/39591 424/133.1 |
| 2008/0145420 | A1 | 6/2008 | Simon | | |
| 2008/0260822 | A1 | 10/2008 | Simon et al. | | |

FOREIGN PATENT DOCUMENTS

| EP | 0799310 A1 | 10/1997 | | |
|---|---|---|---|---|
| WO | 1995/024495 | 9/1995 | | |
| WO | 1996/018734 | 6/1996 | | |
| WO | WO 9618734 A1 * | 6/1996 | ............. | C07K 14/47 |
| WO | 1998/057993 | 12/1998 | | |
| WO | 2009/139624 A1 | 11/2009 | | |

OTHER PUBLICATIONS

Perrier et al., J Biol Chem. May 19, 2006;281(20):14280-7. Epub Mar. 16, 2006.*
Jones et al., Biochim Biophys Acta. Dec. 8, 1998;1429(1):265-74.*
Royle et al., J Biol Chem. May 30, 2003;278(22):20140-53. Epub Mar. 10, 2003.*
Berdoz et al. "In vitro comparision of the antigen-binding and stability properties of the various molecular forms of IgA antibodies assembled and produced in CHO cells", 1999, Proc Natl Acad Sci U S A. vol. 96, pp. 3029-3034.
Chintalacharuvu, et al. "Production and characterization of recombinant IgA", 1999, Immunotechnology. vol. 4, pp. 165-174.
Dallas et al. "Binding of Clostridium difficile toxin A to human milk secretory component", J. Med. Microbiol. 47:879-888 (1998).
de Hoop et al. "Intracellular Routing of Wild-Type and Mutated Polymeric Imunoglobulin Receptor in Hippocampal Neurons in Culture", J Cell Biol., vol. 130, pp. 1447-1459.
Deshpande et al. "GlycoSpectrumScan: Fishing Glycopeptides from MS Spectra of Protease Digests of Human Colostrum sIgA", J. Proteome Res., 2010, 9:1063-1075.
Dwyer et al. "Considerations for the Use of Salivary IgA for Monitoring Mucosal Immune Function" in Aviation, Space, and Environmental Medicine, 2010, vol. 81, pp. 581-584.

(Continued)

*Primary Examiner* — Michael Szperka
(74) *Attorney, Agent, or Firm* — Loza & Loza, LLP; Michael Fedrick

(57) ABSTRACT

The invention provides a method of producing an immune complex preparation based on a secretory immunoglobulin, which is non-human secretion derived, comprising providing an industrial scale production system, capable of producing an N-glycosylated Secretory Component, producing by such system a Secretory Component comprising at least 0.01 mol non-core fucose per mol Secretory Component, and combining said Secretory Component with at least one of IgA or IgM immunoglobulins having a native glycosylation pattern to obtain an immune complex. The invention provides an isolated recombinant Secretory Component comprising the amino acid sequence of SEQ ID 1, or a functionally active variant thereof, which has a Lewis-type N-glucosylation pattern and at least 2 mol non-core fucose per mol Secretory Component; and an immune complex preparation based on a secretory immunoglobulin, derived from sources other than human secretions, comprising a Secretory Component with a Lewis-type N-glucosylation pattern and at least 0.01 mol non-core fucose per mol Secretory Component, and at least one of IgA or IgM immunoglobulins having a native glycosylation pattern.

18 Claims, 11 Drawing Sheets

Specification includes a Sequence Listing.

(56) References Cited

OTHER PUBLICATIONS

Grabenhorst et al. "Genetic engineering of recombinant glycoproteins and the glycosylation pathway in mammalian host cells", Glycoconjugate Journal, 1999, 16(2):81-97.
Gustafsson et al. "Carbohydrate phenotyping of human and animal milk glycoproteins", Glycoconjugate Journal, 2005, 22(3) 109-118.
Huang P et al. "Norovirus and Histo-Blood Group Antigens: Demonstration of a Wide Spectrum of Strain Specificities and Classification of Two Major Binding Groups among Multiple Binding Patterns", Journal of Virology, 2005, vol. 79, No. 11, pp. 6714-6722.
Johansen et al. "Recombinant expression of polymeric IgA: incorpration of J chain and secretory component of human origin", Eur J Immunol., 1999, vol. 29, pp. 1701-1708.
Larrick et al. "Production of secretory IgA antibodies in plants", 2001, Biomol Eng., vol. 18, pp. 87-94.
Löfling et al. "Studies of Lewis antigens and H. pylori adhesion in CHO cell lines engineered to express Lewis b determinants", 2008, Glycobiology, vol. 18, No. 7, pp. 494-501.
Ma B. et al. "Fucosylation in prokaryotes and eukaryotes", 2006, Glycobiology vol. 16, No. 12, pp. 158R-184R.
Matsumoto et al. "Release of Non-Glycosylated Polymeric Immunoglobulin Receptor Protein", 2003, Scand J Immunol., vol. 58, pp. 471-476.
Michetti et al. "Production and Use of Monoclonal IgA Antibodies Complexed with Recombinant Secretory Component for Passive Mucosal Protection", 1991, Adv Exp Med Biol, vol. 310, pp. 183-185.
North et al. "Glycobiology and Extracellular Matrices: Glycomics Profiling of Chinese Hamster Ovary Cells Glycosylation Mutants Reveals N-Glycans of a Novel Size and Complexity", 2010, J Biol Chem., vol. 285, pp. 5759-5775.
Ogura, "Transient expression of polymeric immunoglobulin receptor in human adenocarcinoma cell line HT-29", 2005, J Oral Sci., vol. 47, pp. 15-20.
Pabst et al. "Mass + Retention Time = Structure: A Strategy for the Analysis of N-Glycans by Carbon LC-ESI-MS and Its Application to Fibrin N-Glycans", 2007, Anal. Chem., 79, 5051-5057.
Perrier et al. "Glycobiology and Extracellular Matrices: Glycans on Secretory Component Participate in Innate Protection against Mucosal Pathogens", The Journal of Biological Chemistry, 281(20):14280-14287 (2006).
Phalipon et al. "Secretory Component: A New Role in Secretory IgA-Mediated Immune Exclusion In Vivo", 2002, Immunity, vol. 17, pp. 107-115.
Ploegaert et al. "Genetic variation of natural antibodies in milk of Dutch Holstein-Friesian cows", J. Dairy Sci., 2010, 93 (11):5467-5473.
Porter "Studies of Porcine Secretory IgA and its Component Chains in Relation to Intestinal Absorption of Colostral Immunoglobulins by the Neonatal Pig", Immunology, 1973, 24(1):163-176.
Potvin et al. "Transfection of a Human α-(1,3)Fucosyltransferase Gene into Chinese hamster Ovary Cells", Journal of Biological Chemistry, US, vol. 265, No. 3, pp. 1615-1622, 1990.
Prinsloo et al. "In vitro refolding of recombinant human free secretory component using equilibrium gradient dialysis", 2006, Protein Expr Purif., vol. 47, pp. 179-185.
Rindisbacher et al. "Production of Human Secretory Component with Dimeric IgA Binding Capacity Using Viral Expression Systems", 1995, J Biol Chem, vol. 270, pp. 14220-14228.
Rittershaus et al. "Carbohydrates, Lipids, and Other Natural Products: Recombinant Glycoproteins That Inhibit Complement Activation and Also Bind the Selectin Adhesion Molecules", 1999, J Biol Chem., vol. 274, pp. 11237-11244.
Schlaeger et al. "Propagation of a mouse myeloma cell line J558L producing human CD4 immunoglobulin G1", Journal of Immunologiocal Methods, NL, 1992, vol. 146, pp. 111-120.
Stadlmann et al. "Analysis of immunoglobulin glycosylation by LC-ESI-MS of glycopeptides and oligosaccharides", Proteomics, 8:2858-2871 (2008).
Suguro et al. "Novel approach for transient protein expression in primary cultures of human dental pulp-derived cells", Protein Expr Purif., 2011, vol. 78, pp. 143-148.
Svennerholm "Quantitative Estimation of Sialic Acids, II. A Colorimetric Resorcinol-Hydrochloric Acid Method", 1957, Biochim Biophys Acta., vol. 24, pp. 604-611.
Wuhrer et al "Glygosylation profiling of immunoglobulin G (IgA) subclasses from human serum", 2007, Proteomics 7:4070-4081.
Xu et al. "Effects of fucosylated milk of goat and mouse on Helicobacter pylori binding to the Lewis b antigen", World J. Gastroenterol., 10(14):2063-2066 (2004).
International Search Report for International Patent Application No. PCT/EP2013/057201, dated Jun. 17, 2013, 5 pages.
International Written Opinion for International Patent Application No. PCT/EP2013/057201, dated Jun. 17, 2013, 5 pages.
International Preliminary Report on Patentability for International Patent Application No. PCT/EP2013/057201, dated Oct. 7, 2014, 6 pages.
European Search Report for EP Application No. 11160464.1, dated Oct. 10, 2011, 10 pages.
Crottet et al, "Expression, purification and biochemical characterization of recombinant murine secretory aomponent: a novel tool in mucosal immunology", Biochemical Journal, vol. 341, No. 2, 1999, pp. 299-306.
Royle et al, "Secretory IgA N- and O-Glycans Provide a Link between the Innate and Adaptive Immune Systems", Journal of Biological Chemistry, vol. 278, No. 22, 2003, pp. 20140-20153.
Tang et al, "Important Role of Polymeric Immunoglobulin Receptor in Mucosal Immunity", Chinese Journal of Biochemistry and Molecular Biol., 2007, 9, pp. 724-729; English Abstract only.
Van Den Nieuwenhof et al, "Recombinant glycodelin carrying the same type of glycan structures as contraceptive glycodelin-A can be produced in human kidney 293 cells but not in Chinese hamster ovary cells", Eur. J. Biochem., vol. 267, pp. 4753-4762 (2000).
Xu et al, "The genomic sequence of the Chinese hamster ovary (CHO)-K1 cell line", Nature Biotechnolog, vol. 29, No. 8, pp. 735-742 (2011).

\* cited by examiner

Fig. 1

MLLFVLTCLLAVFPAISTKSPIFGPEEVNSVEGNSVSITCYYPPTSVNRHTRKYWCRQG
ARGGCITLISSEGYVSSKYAGRANLTNFPENGTFVVNIAQLSQDDSGRYKCGLGINSR
GLSFDVSLEVSQGPGLLNDTKVYTVDLGRTVTINCPFKTENAQKRKSLYKQIGLYPVLV
IDSSGYVNPNYTGRIRLDIQGTGQLLFSVVINQLRLSDAGQYLCQAGDDSNSNKKNAD
LQVLKPEPELVYEDLRGSVTFHCALGPEVANVAKFLCRQSSGENCDVVVNTLGKRAP
AFEGRILLNPQDKDGSFSVVITGLRKEDAGRYLCGAHSDGQLQEGSPIQAWQLFVNE
ESTIPRSPTVVKGVAGSSVAVLCPYNRKESKSIKYWCLWEGAQNGRCPLLVDSEGWV
KAQYEGRLSLLEEPGNGTFTVILNQLTSRDAGFYWCLTNGDTLWRTTVEIKIIEGEPNL
KVPGNVTAVLGETLKVPCHFPCKFSSYEKYWCKWNNTGCQALPSQDEGPSKAFVNC
DENSRLVSLTLNLVTRADEGWYWCGVKQGHFYGETAAVYVAVEERKAAGSRDVSLA
KADAAPDEKVLDSGFREIENKAIQDPRLFAE (Seq. ID. No. 1)

Fig. 2

*CCCCAAGCTT*ATGCTGCTGTTCGTGCTGACCTGCCTGCTGGCCGTGTTCCCCGC
CATCAGCACCAAGAGCCCCATCTTCGGCCCCGAGGAGGTGAACAGCGTGGAGGG
CAACAGCGTGAGCATCACCTGCTACTACCCCCCACCAGCGTGAACAGACACACC
AGAAAGTACTGGTGCAGACAGGGCGCCAGAGGCGGCTGCATCACCCTGATCAGC
AGCGAGGGCTACGTGAGCAGCAAGTACGCCGGCAGAGCCAACCTGACCAACTTC
CCCGAGAACGGCACCTTCGTGGTGAACATCGCCCAGCTGAGCCAGGACGACAGC
GGCAGATACAAGTGCGGCCTGGGCATCAACAGCAGAGGCCTGAGCTTCGACGTG
AGCCTGGAGGTGAGCCAGGGCCCCGGCCTGCTGAACGACACCAAGGTGTACAC
CGTGGACCTGGGCAGAACCGTGACCATCAACTGCCCCTTCAAGACCGAGAACGC
CCAGAAGAGAAAGAGCCTGTACAAGCAGATCGGCCTGTACCCCGTGCTGGTGATC
GACAGCAGCGGCTACGTGAACCCCAACTACACCGGCAGAATCAGACTGGACATC
CAGGGCACCGGCCAGCTGCTGTTCAGCGTGGTGATCAACCAGCTGAGACTGAGC
GACGCCGGCCAGTACCTGTGCCAGGCCGGCGACGACAGCAACAGCAACAAGAA
GAACGCCGACCTGCAGGTGCTGAAGCCCGAGCCCGAGCTGGTGTACGAGGACC
TGAGAGGCAGCGTGACCTTCCACTGCGCCCTGGGCCCCGAGGTGGCCAACGTG
GCCAAGTTCCTGTGCAGACAGAGCAGCGGCGAGAACTGCGACGTGGTGGTGAA
CACCCTGGGCAAGAGAGCCCCCGCCTTCGAGGGCAGAATCCTGCTGAACCCCCA
GGACAAGGACGGCAGCTTCAGCGTGGTGATCACCGGCCTGAGAAAGGAGGACG
CCGGCAGATACCTGTGCGGCGCCCACAGCGACGGCCAGCTGCAGGAGGGCAGC
CCCATCCAGGCCTGGCAGCTGTTCGTGAACGAGGAGAGCACCATCCCCAGAAGC
CCCACCGTGGTGAAGGGCGTGGCCGGCAGCAGCGTGGCCGTGCTGTGCCCCTA
CAACAGAAAGGAGAGCAAGAGCATCAAGTACTGGTGCCTGTGGGAGGGCGCCCA
GAACGGCAGATGCCCCCTGCTGGTGGACAGCGAGGGCTGGGTGAAGGCCCAGT
ACGAGGGCAGACTGAGCCTGCTGGAGGAGCCCGGCAACGGCACCTTCACCGTG
ATCCTGAACCAGCTGACCAGCAGAGACGCCGGCTTCTACTGGTGCCTGACCAAC
GGCGACACCCTGTGGAGAACCACCGTGGAGATCAAGATCATCGAGGGCGAGCCC
AACCTGAAGGTGCCCGGCAACGTGACCGCCGTGCTGGGCGAGACCCTGAAGGT
GCCCTGCCACTTCCCCTGCAAGTTCAGCAGCTACGAGAAGTACTGGTGCAAGTG
GAACAACACCGGCTGCCAGGCCCTGCCCAGCCAGGACGAGGGCCCCAGCAAGG
CCTTCGTGAACTGCGACGAGAACAGCAGACTGGTGAGCCTGACCCTGAACCTGG
TGACCAGAGCCGACGAGGGCTGGTACTGGTGCGGCGTGAAGCAGGGCCACTTCT
ACGGCGAGACCGCCGCCGTGTACGTGGCCGTGGAGGAGAAAGGCCGCCGGC
AGCAGAGACGTGAGCCTGGCCAAGGCCGACGCCGCCCCGACGAGAAGGTGCT
GGACAGCGGCTTCAGAGAGATCGAGAACAAGGCCATCCAGGACCCCAGACTGTT
CGCCGAGTGA*TCTAGACCCC* (Seq. ID. No. 2)

Fig. 3

MLVVQMPFSFPMAHFILFVFTVSTIFHVQQRLAKIQAMWELPVQIPVLASTSKALGPSQ
LRGMWTINAIGRLGNQMGEYATLYALAKMNGRPAFIPAQMHSTLAPIFRITLPVLHSAT
ASRIPWQNYHLNDWMEEEYRHIPGEYVRFTGYPCSWTFYHHLRQEILQEFTLHDHVR
EEAQKFLRGLQVNGSRPGTFVGVHVRRGDYVHVMPKVWKGVVADRRYLQQALDWF
RARYSSLIFVVTSNGMAWCRENIDTSHGDVVFAGDGIEGSPAKDFALLTQCNHTIMTIG
TFGIWAAYLTGGDTIYLANYTLPDSPFLKIFKPEAAFLPEWTGIAADLSPLLKH (Seq. ID.
No. 3)

Fig. 4

*GCTAGC*ATGCTGGTGGTGCAGATGCCGTTTAGCTTTCCGATGGCGCATTTTATTCT
GTTTGTGTTTACCGTGAGCACCATTTTTCATGTGCAGCAGCGCCTGGCGAAAATTC
AGGCGATGTGGGAACTGCCGGTGCAGATTCCGGTGCTGGCGAGCACCAGCAAAG
CGCTGGGCCCGAGCCAGCTGCGCGGCATGTGGACCATTAACGCGATTGGCCGCC
TGGGCAACCAGATGGGCGAATATGCGACCCTGTATGCGCTGGCGAAAATGAACGG
CCGCCCGGCGTTTATTCCGGCGCAGATGCATAGCACCCTGGCGCCGATTTTTCGC
ATTACCCTGCCGGTGCTGCATAGCGCGACCGCGAGCCGCATTCCGTGGCAGAACT
ATCATCTGAACGATTGGATGGAAGAAGAATATCGCCATATTCCGGGCGAATATGTGC
GCTTTACCGGCTATCCGTGCAGCTGGACCTTTTATCATCATCTGCGCCAGGAAATT
CTGCAGGAATTTACCCTGCATGATCATGTGCGCGAAGAAGCGCAGAAATTTCTGC
GCGGCCTGCAGGTGAACGGCAGCCGCCCGGGCACCTTTGTGGGCGTGCATGTG
CGCCGCGGCGATTATGTGCATGTGATGCCGAAAGTGTGGAAAGGCGTGGTGGCG
GATCGCCGCTATCTGCAGCAGGCGCTGGATTGGTTTCGCGCGCGCTATAGCAGCC
TGATTTTTGTGGTGACCAGCAACGGCATGGCGTGGTGCCGCGAAAACATTGATAC
CAGCCATGGCGATGTGGTGTTTGCGGGCGATGGCATTGAAGGCAGCCCGGCGAA
AGATTTTGCGCTGCTGACCCAGTGCAACCATACCATTATGACCATTGGCACCTTTG
GCATTTGGGCGGCGTATCTGACCGGCGGCGATACCATTTATCTGGCGAACTATACC
CTGCCGGATAGCCCGTTTCTGAAAATTTTTAAACCGGAAGCGGCGTTTCTGCCGG
AATGGACCGGCATTGCGGCGGATCTGAGCCCGCTGCTGAAACATTAA*GAATTC*
(Seq. ID. No. 4)

Fig. 5

MDPLGAAKPQWPWRRSLAALLFQLLVAVCFFSYLRVSRDDATGSPRAPSGSSRQDT
TPTRPTLLILLRTWPFHIPVALSRCSEMVPGTADCHITADRKVYPQADMVIVHHWDIMS
NPKSRLPPSPRPQGQRWIWFNLEPPPNCQHLEALDRYFNLTMSYRSDSDIFTPYGW
LEPWSGQPAHPPLNLSAKTELVAWAVSNWKPDSARVRYYQSLQAHLKVDVYGRSHK
PLPKGTMMETLSRYKFYLAFENSLHPDYITEKLWRNALEAWAVPVVLGPSRSNYERFL
PPDAFIHVDDFQSPKDLARYLQELDKDHARYLSYFRWRETLRPRSFSWALDFCKAC
WKLQQESRYQTVRSIAAWFT (Seq. ID. No.5)

Fig. 6

*TCTAGA*ATGGATCCGCTGGGCGCGGCGAAACCGCAGTGGCCGTGGCGCCGCAG
CCTGGCGGCGCTGCTGTTTCAGCTGCTGGTGGCGGTGTGCTTTTTTAGCTATCTG
CGCGTGAGCCGCGATGATGCGACCGGCAGCCCGCGCGCGCCGAGCGGCAGCA
GCCGCCAGGATACCACCCCGACCCGCCCGACCCTGCTGATTCTGCTGCGCACCT
GGCCGTTTCATATTCCGGTGGCGCTGAGCCGCTGCAGCGAAATGGTGCCGGGCA
CCGCGGATTGCCATATTACCGCGGATCGCAAAGTGTATCCGCAGGCGGATATGGT
GATTGTGCATCATTGGGATATTATGAGCAACCCGAAAAGCCGCCTGCCGCCGAGC
CCGCGCCCGCAGGGCCAGCGCTGGATTTGGTTTAACCTGGAACCGCCGCCGAAC
TGCCAGCATCTGGAAGCGCTGGATCGCTATTTTAACCTGACCATGAGCTATCGCAG
CGATAGCGATATTTTTACCCCGTATGGCTGGCTGGAACCGTGGAGCGGCCAGCCG
GCGCATCCGCCGCTGAACCTGAGCGCGAAAACCGAACTGGTGGCGTGGGCGGT
GAGCAACTGGAAACCGGATAGCGCGCGCGTGCGCTATTATCAGAGCCTGCAGGC
GCATCTGAAAGTGGATGTGTATGGCCGCAGCCATAAACCGCTGCCGAAAGGCACC
ATGATGGAAACCCTGAGCCGCTATAAATTTTATCTGGCGTTTGAAAACAGCCTGCAT
CCGGATTATATTACCGAAAAACTGTGGCGCAACGCGCTGGAAGCGTGGGCGGTG
CCGGTGGTGCTGGGCCCGAGCCGCAGCAACTATGAACGCTTTCTGCCGCCGGAT
GCGTTTATTCATGTGGATGATTTTCAGAGCCCGAAAGATCTGGCGCGCTATCTGCA
GGAACTGGATAAAGATCATGCGCGCTATCTGAGCTATTTTCGCTGGCGCGAAACCC
TGCGCCCGCGCAGCTTTAGCTGGGCGCTGGATTTTTGCAAAGCGTGCTGGAAAC
TGCAGCAGGAAAGCCGCTATCAGACCGTGCGCAGCATTGCGGCGTGGTTTACCTA
A*GCGGCCGC* (Seq. ID. No. 6)

Fig. 7

MASKVSCLYVLTVVCWASALWYLSITRPTSSYTGSKPFSHLTVARKNFTFGNIRTRPIN
PHSFEFLINEPNKCEKNIPFLVILISTTHKEFDARQAIRETWGDENNFKGIKIATLFLLGK
NADPVLNQMVEQESQIFHDIIVEDFIDSYHNLTLKTLMGMRWVATFCSKAKYVMKTDS
DIFVNMDNLIYKLLKPSTKPRRRYFTGYVINGGPIRDVRSKWYMPRDLYPDSNYPPFC
SGTGYIFSADVAELIYKTSLHTRLLHLEDVYVGLCLRKLGIHPFQNSGFNHWKMAYSLC
RYRRVITVHQISPEEMHRIWNDMSSKKHLRC (Seq. ID. No. 7)

Fig. 8

*CCCCCGCTAGC*ATGGCCAGCAAGGTGAGCTGCCTGTACGTGCTGACCGTGGTGT
GCTGGGCCAGCGCCCTGTGGTACCTGAGCATCACCAGACCCACCAGCAGCTACA
CCGGCAGCAAGCCCTTCAGCCACCTGACCGTGGCCAGAAAGAACTTCACCTTCG
GCAACATCAGAACCAGACCCATCAACCCCCACAGCTTCGAGTTCCTGATCAACGA
GCCCAACAAGTGCGAGAAGAACATCCCCTTCCTGGTGATCCTGATCAGCACCACC
CACAAGGAGTTCGACGCCAGACAGGCCATCAGAGAGACCTGGGGCGACGAGAA
CAACTTCAAGGGCATCAAGATCGCCACCCTGTTCCTGCTGGGCAAGAACGCCGA
CCCCGTGCTGAACCAGATGGTGGAGCAGGAGAGCCAGATCTTCCACGACATCATC
GTGGAGGACTTCATCGACAGCTACCACAACCTGACCCTGAAGACCCTGATGGGCA
TGAGATGGGTGGCCACCTTCTGCAGCAAGGCCAAGTACGTGATGAAGACCGACA
GCGACATCTTCGTGAACATGGACAACCTGATCTACAAGCTGCTGAAGCCCAGCAC
CAAGCCCAGAAGAAGATACTTCACCGGCTACGTGATCAACGGCGGCCCCATCAGA
GACGTGAGAAGCAAGTGGTACATGCCCAGAGACCTGTACCCCGACAGCAACTACC
CCCCCTTCTGCAGCGGCACCGGCTACATCTTCAGCGCCGACGTGGCCGAGCTGA
TCTACAAGACCAGCCTGCACACCAGACTGCTGCACCTGGAGGACGTGTACGTGG
GCCTGTGCCTGAGAAAGCTGGGCATCCACCCCTTCCAGAACAGCGGCTTCAACC
ACTGGAAGATGGCCTACAGCCTGTGCAGATACAGAAGAGTGATCACCGTGCACCA
GATCAGCCCCGAGGAGATGCACAGAATCTGGAACGACATGAGCAGCAAGAAGCA
CCTGAGATGCTGA*GCGGCCGCCCCCC* (Seq. ID. No. 8)

Fig. 9

MAHMKTRLVYASILMMGALCLYFSMDSFRELPFVFKKSHGKFLQIPDIDCKQKPPFLVL
LVTSSHKQLAARMAIRKTWGRETSVQGQQVRTFFLLGTSDSTEEMDATTLESEQHRD
IIQKDFKDAYFNLTLKTMMGMEWVYHFCPQTAYVMKTDSDMFVNVGYLTELLLKKNKT
TRFFTGYIKPHDFPIRQKFNKWFVSKFEYPWDRYPPFCSGTGYVFSSDVAIQVYNVSE
SVPFIKLEDVFVGLCLAKLKIRPEELHTKQTFFPGGLRFSVCRFQKIVACHFMKPQDLL
TYWQALENSKEQDCPAV (Seq. ID. No. 9)

Fig. 10

*CCCCCGCTAGC*ATGGCCCACATGAAGACCAGACTGGTGTACGCCAGCATCCTGAT
GATGGGCGCCCTGTGCCTGTACTTCAGCATGGACAGCTTCAGAGAGCTGCCCTTC
GTGTTCAAGAAGAGCCACGGCAAGTTCCTGCAGATCCCCGACATCGACTGCAAG
CAGAAGCCCCCCTTCCTGGTGCTGCTGGTGACCAGCAGCCACAAGCAGCTGGCC
GCCAGAATGGCCATCAGAAAGACCTGGGGCAGAGAGACCAGCGTGCAGGGCCA
GCAGGTGAGAACCTTCTTCCTGCTGGGCACCAGCGACAGCACCGAGGAGATGGA
CGCCACCACCCTGGAGAGCGAGCAGCACAGAGACATCATCCAGAAGGACTTCAA
GGACGCCTACTTCAACCTGACCCTGAAGACCATGATGGGCATGGAGTGGGTGTAC
CACTTCTGCCCCCAGACCGCCTACGTGATGAAGACCGACAGCGACATGTTCGTGA
ACGTGGGCTACCTGACCGAGCTGCTGCTGAAGAAGAACAAGACCACCAGATTCTT
CACCGGCTACATCAAGCCCCACGACTTCCCCATCAGACAGAAGTTCAACAAGTGG
TTCGTGAGCAAGTTCGAGTACCCCTGGGACAGATACCCCCCCTTCTGCAGCGGCA
CCGGCTACGTGTTCAGCAGCGACGTGGCCATCCAGGTGTACAACGTGAGCGAGA
GCGTGCCCTTCATCAAGCTGGAGGACGTGTTCGTGGGCCTGTGCCTGGCCAAGC
TGAAGATCAGACCCGAGGAGCTGCACACCAAGCAGACCTTCTTCCCCGGCGGCC
TGAGATTCAGCGTGTGCAGATTCCAGAAGATCGTGGCCTGCCACTTCATGAAGCC
CCAGGACCTGCTGACCTACTGGCAGGCCCTGGAGAACAGCAAGGAGCAGGACTG
CCCCGCCGTGTGA*GCGGCCGCCCCCC* (Seq. ID. No. 10)

Fig. 11

MSVGRRRVKLLGILMMANVFIYLIVEVSKNSSQDKNGKGGVIIPKEKFWKPPSTPRAY
WNREQEKLNRWYNPILNRVANQTGELATSPNTSHLSYCEPDSTVMTAVTDFNNLPDR
FKDFLLYLRCRNYSLLIDQPKKCAKKPFLLLAIKSLIPHFARRQAIRESWGRETNVGNQ
TVVRVFLLGKTPPEDNHPDLSDMLKFESDKHQDILMWNYRDTFFNLSLKEVLFLRWV
STSCPDAEFVFKGDDDVFVNTHHILNYLNSLSKSKAKDLFIGDVIHNAGPHRDKKLKY
YIPEVFYTGVYPPYAGGGGFLYSGPLALRLYSATSRVHLYPIDDVYTGMCLQKLGLVPE
KHKGFRTFDIEEKNKKNICSYIDLMLVHSRKPQEMIDIWSQLQSPNLKC (Seq. ID. No.
11)

Fig. 12

*CCCCCGCTAGC*ATGAGCGTGGGCAGAAGAAGAGTGAAGCTGCTGGGCATCCTGA
TGATGGCCAACGTGTTCATCTACCTGATCGTGGAGGTGAGCAAGAACAGCAGCCA
GGACAAGAACGGCAAGGGCGGCGTGATCATCCCCAAGGAGAAGTTCTGGAAGCC
CCCCAGCACCCCCAGAGCCTACTGGAACAGAGAGCAGGAGAAGCTGAACAGATG
GTACAACCCCATCCTGAACAGAGTGGCCAACCAGACCGGCGAGCTGGCCACCAG
CCCCAACACCAGCCACCTGAGCTACTGCGAGCCCGACAGCACCGTGATGACCGC
CGTGACCGACTTCAACAACCTGCCCGACAGATTCAAGGACTTCCTGCTGTACCTG
AGATGCAGAAACTACAGCCTGCTGATCGACCAGCCCAAGAAGTGCGCCAAGAAG
CCCTTCCTGCTGCTGGCCATCAAGAGCCTGATCCCCCACTTCGCCAGAAGACAG
GCCATCAGAGAGAGCTGGGGCAGAGAGACCAACGTGGGCAACCAGACCGTGGT
GAGAGTGTTCCTGCTGGGCAAGACCCCCCCGAGGACAACCACCCCGACCTGAG
CGACATGCTGAAGTTCGAGAGCGACAAGCACCAGGACATCCTGATGTGGAACTAC
AGAGACACCTTCTTCAACCTGAGCCTGAAGGAGGTGCTGTTCCTGAGATGGGTGA
GCACCAGCTGCCCCGACGCCGAGTTCGTGTTCAAGGGCGACGACGACGTGTTCG
TGAACACCCACCACATCCTGAACTACCTGAACAGCCTGAGCAAGAGCAAGGCCAA
GGACCTGTTCATCGGCGACGTGATCCACAACGCCGGCCCCCACAGAGACAAGAA
GCTGAAGTACTACATCCCCGAGGTGTTCTACACCGGCGTGTACCCCCCCTACGCC
GGCGGCGGCGGCTTCCTGTACAGCGGCCCCCTGGCCCTGAGACTGTACAGCGC
CACCAGCAGAGTGCACCTGTACCCCATCGACGACGTGTACACCGGCATGTGCCT
GCAGAAGCTGGGCCTGGTGCCCGAGAAGCACAAGGGCTTCAGAACCTTCGACAT
CGAGGAGAAGAACAAGAAGAACATCTGCAGCTACATCGACCTGATGCTGGTGCAC
AGCAGAAAGCCCCAGGAGATGATCGACATCTGGAGCCAGCTGCAGAGCCCCAAC
CTGAAGTGCTGA*GCGGCCGCCCCCC* (Seq. ID. No. 12)

Fig. 13

<u>mgwswiflfllsgtagvls</u>QVQLQQPGAELVKPGASVKLSCKASGYTFTSYWMHWVKQRPGR
GLEWIGRIDPNSGGTKYNEKFKSKATLTVDKPSSTAYMQLSSLTSEDSAVYYCARYDY
YGSSYFDYWGQGTTVTVSSASPTSPKVFPLSLDSTPQDGNVVVACLVQGFFPQEPLS
VTWSESGQNVTARNFPPSQDASGDLYTTSSQLTLPATQCPDGKSVTCHVKHYTNPS
QDVTVPCPVPPPPPCCHPRLSLHRPALEDLLLGSEANLTCTLTGLRDASGATFTWTPS
SGKSAVQGPPERDLCGCYSVSSVLPGCAQPWNHGETFTCTAAHPELKTPLTANITKS
GNTFRPEVHLLPPPSEELALNELVTLTCLARGFSPKDVLVRWLQGSQELPREKYLTWA
SRQEPSQGTTTFAVTSILRVAAEDWKKGDTFSCMVGHEALPLAFTQKTIDRLAGKPTH
VNVSVVMAEVDGTCY (Seq. ID. No. 13)

Fig. 14

*CCCCAAGCTT*ATGGGCTGGAGCTGGATCTTCCTGTTCCTGCTGAGCGGCACCGC
CGGCGTGCTGAGCCAGGTGCAGCTGCAGCAGCCCGGCGCCGAGCTGGTGAAGC
CCGGCGCCAGCGTGAAGCTGAGCTGCAAGGCCAGCGGCTACACCTTCACCAGCT
ACTGGATGCACTGGGTGAAGCAGAGACCCGGCAGAGGCCTGGAGTGGATCGGC
AGAATCGACCCCAACAGCGGCGGCACCAAGTACAACGAGAAGTTCAAGAGCAAG
GCCACCCTGACCGTGGACAAGCCCAGCAGCACCGCCTACATGCAGCTGAGCAGC
CTGACCAGCGAGGACAGCGCCGTGTACTACTGCGCCAGATACGACTACTACGGCA
GCAGCTACTTCGACTACTGGGGCCAGGGCACCACCGTGACCGTGAGCAGCGCCA
GCCCCACCAGCCCCAAGGTGTTCCCCCTGAGCCTGGACAGCACCCCCCAGGAC
GGCAACGTGGTGGTGGCCTGCCTGGTGCAGGGCTTCTTCCCCCAGGAGCCCCT
GAGCGTGACCTGGAGCGAGAGCGGCCAGAACGTGACCGCCAGAAACTTCCCCC
CCAGCCAGGACGCCAGCGGCGACCTGTACACCACCAGCAGCCAGCTGACCCTG
CCCGCCACCCAGTGCCCCGACGGCAAGAGCGTGACCTGCCACGTGAAGCACTAC
ACCAACCCCAGCCAGGACGTGACCGTGCCCTGCCCCGTGCCCCCCCCCCCCCC
CTGCTGCCACCCCAGACTGAGCCTGCACAGACCCGCCCTGGAGGACCTGCTGCT
GGGCAGCGAGGCCAACCTGACCTGCACCCTGACCGGCCTGAGAGACGCCAGCG
GCGCCACCTTCACCTGGACCCCCAGCAGCGGCAAGAGCGCCGTGCAGGGCCCC
CCCGAGAGAGACCTGTGCGGCTGCTACAGCGTGAGCAGCGTGCTGCCCGGCTG
CGCCCAGCCCTGGAACCACGGCGAGACCTTCACCTGCACCGCCGCCCACCCCG
AGCTGAAGACCCCCCTGACCGCCAACATCACCAAGAGCGGCAACACCTTCAGAC
CCGAGGTGCACCTGCTGCCCCCCCCAGCGAGGAGCTGGCCCTGAACGAGCTG
GTGACCCTGACCTGCCTGGCCAGAGGCTTCAGCCCCAAGGACGTGCTGGTGAGA
TGGCTGCAGGGCAGCCAGGAGCTGCCCAGAGAGAAGTACCTGACCTGGGCCAG
CAGACAGGAGCCCAGCCAGGGCACCACCACCTTCGCCGTGACCAGCATCCTGAG
AGTGGCCGCCGAGGACTGGAAGAAGGGCGACACCTTCAGCTGCATGGTGGGCC
ACGAGGCCCTGCCCCTGGCCTTCACCCAGAAGACCATCGACAGACTGGCCGGCA
AGCCCACCCACGTGAACGTGAGCGTGGTGATGGCCGAGGTGGACGGCACCTGC
TACTGA*TCTAGACCCC* (Seq. ID. No. 14)

ns and IgM, along with the
SECRETORY IMMUNOGLOBULIN COMPLEX

CROSS-REFERENCE TO RELATED APPLICATIONS

This application is the U.S. national stage of International Patent Application No. PCT/EP2013/057201, filed on Apr. 5, 2013 and entitled SECRETORY IMMUNOGLOBULIN COMPLEX, which claims the benefit of priority under 35 U.S.C. § 119 from European Patent Application No. 12163439.8, filed on Apr. 5, 2012. The disclosures of the foregoing applications are incorporated herein by reference in their entirety.

SEQUENCE LISTING

The entire content of a Sequence Listing titled "Sequence_Listing.txt," created on Oct. 3, 2014 and having a size of 43 kilobytes, which has been submitted in electronic form in connection with the present application, is hereby incorporated by reference herein in its entirety.

FIELD OF THE INVENTION

The invention refers to a method of producing an immune complex preparation based on a secretory immunoglobulin, which is not derived from human milk, the immune complex preparation and a recombinant Secretory Component.

BACKGROUND

The Secretory Component (SC) is a component of secretory immunoglobulin (SIgA and SIgM), comprising the extracellular part of the polymeric immunoglobulin receptor (pIgR). Polymeric IgA and IgM binds, mediated by the J-chain, to the polymeric immunoglobulin receptor on the basolateral surface of epithelial cells and is taken up into the cell via transcytosis. The receptor-immunoglobulin complex passes through the cellular compartments before being secreted on the luminal surface of the epithelial cells, still attached to the receptor. Proteolysis of the receptor occurs and the dimeric IgA molecule or the IgM, along with the Secretory Component, are free to diffuse throughout the lumen.

The Secretory Component has been described to occur in various body secretions such as saliva, tears, mucus and milk. It can be found either as part of secretory immunoglobulins (SIg, i.e. SIgA and SIgM) as well as free Secretory Component (fSC).

Human Secretory Component (hSC) is derived from the polymeric immunoglobulin receptor by cleavage of the extracellular part of the receptor molecule in the process of transcytosis. It has an apparent molecular weight of about 80 kDa and consists of the first about 585 amino acids of the pIgR (polymeric Ig-Receptor) arranged in five V-type immunoglobulin domains. It has 7 potential N-glycosylation sites. This strong glycosylation contributes to the large apparent molecular weight. The composition of these glycans includes bi- and triantennarry structures, Lewis type structures as well as galactose and sialic acids. These glycans constitute binding epitopes for bacterial, viral, fungal and protozoan structures such as adhesins and toxins as well as mucins and receptors on host tissues.

A proporsed function of the Secretory Component is the protection of polymeric immunglobulin from proteolytic degradation and binding to pathogen related structures and toxins such as *Helicobacter pylori*, enteropathogenic *E. coli*, *Clostridium difficile* toxin A and *Streptococcus pneumoniae* cholin binding protein A. Glycans on SC have proven to participate in innate protection against mucosal pathogens (Perrier et al. THE JOURNAL OF BIOLOGICAL CHEMISTRY Vol. 281(20), pp. 14280-14287, 2006). The authors reported that recombinant human SC produced from transfected Chinese Hamster Ovary cells (CHO) behaved identically to the SC purified from human milk. The interaction with pathogen antigens was mediated by glycans present on hSC and involved galactose and sialic acid residues. hSC was identified as a microbial scavenger contributing to the antipathogenic arsenal that protects the body epithelial surface.

SC purified from human milk was found to competitively inhibit *Clostridium difficile* toxin A binding to receptors (Dallas et al. J. Med. Microbiol. 47: 879-888 (1998)). Removing carbohydrates from SIgA and SC by enzymatic digestion showed that *Clostridium difficile* toxin A binds much less to deglycosylated SC than to glycosylated SC.

Human SC presents a wide range of glycan structures, including all of the different Lewis and sialyl-Lewis epitopes that can potentially bind lectins and bacterial adhesins. One can find galactose linked both beta1-4 and beta1-3 to GlcNAc; fucose linked alpha1-3 and alpha1-4 to GlcNAc and alpha1-2 to galactose, as well as both alpha2-3- and alpha2-6-linked sialic acids. More than 50% of the glycans of SC from human milk show various types of non-core fucosylation, the most abundant fucose-containing antigen is Lewis x. About 30% of Lewis-type fucosylated antigens in human SC are sialylated. Altogether, SC from human milk displays more than 50 different glycoforms.

Proposed functions of glycans on SC are e.g.
mediation of anchoring of secretory immunoglobulin in the mucus,
mediation of binding of secretory immunoglobulin/antigen complexes to certain receptors (e.g. DC-SIGN),
the action as competitive inhibitor ("decoy") of pathogen structure binding to host cells, e.g. by acting as decoy for lectin-like receptors expressed by pathogenic toxins, viruses and bacteria.
the protection of secretory immunoglobulin and of SC against proteases The multitude of glycan structures found in natural SC may reflect the multitude of functions. However for certain therapeutic and prophylactic uses of secretory immunoglobulins it may be advantageous to reduce the complexity of the glycan population in a preparation of secretory immunoglobulin. A bias towards certain glycan structures and modifications may increase efficacy and/or reduce potential side effects of such a preparation of secretory immunoglobulin.

Human Secretory Component has been recombinantly expressed in a variety of genetically engineered organisms and cells such as bacteria (*E. coli*), insect cells (Sf9 cells), mammalian cells (Chinese hamster ovary cells, African green monkey kidney CV-1 cells, human osteosarcoma cells TK-143B, human HeLa cells, Baby hamster kidney cells, human adenocarcinoma cells HT29, mouse fibroblasts, Madin-Darby canine kidney cells) and plants (e.g. US20080260822, EP799310, Michetti et al. 1991 Adv Exp Med Biol, vol 310, pp 183-5; Suguro et al. 2011, Protein Expr Purif. Vol. 78, pp 143-8; Prinsloo et al. 2006 Protein Expr Purif. vol 47, pp 179-85; Ogura, 2005, J Oral Sci. vol 47, pp 15-20; Matsumoto et al. 2003 Scand J Immunol. Vol 58, pp 471-6; Johansen et al. 1999 Eur J Immunol., Vol 29, pp 1701-8; Chintalacharuvu and Morrison 1999, Immunotechnology. Vol 4, pp 165-74; de Hoop et al. 1995. J Cell Biol. Vol 130, pp 1447-59; Larrick et al. 2001 Biomol Eng. Vol 18, pp 87-94; Berdoz et al. 1999, Proc Natl Acad Sci USA. vol 96, pp 3029-34; Rindisbacher et al. 1995, J Biol Chem vol. 270, pp 14220-8).

The glycan pattern found on recombinant SC is dependent on the host species, the host organism, the tissue of origin and the physiological state of the genetically engineered cell.

While *E. coli* is unable to produce N-glycosylated proteins at all, most of the other hosts used so far for expressing recombinant SC are unable to produce Lewis x fucosylation (Sf9 cells, plant cells, HeLa, CHO cells, CV-1 cells, 143B cells, BHK cells, mouse fibroblasts, MDCK cells). Under the conditions described, HT-29 do not efficiently produce Lewis antigens on N-Glycans. HT-29 cells cultured in glucose have properties of undifferentiated multipotent transit cells, are very unstable, the conversion of high-mannose to complex glycoproteins is, however, severely reduced in HT-29 cells grown in differentiation non-permissive conditions (HT-29 Glc+) whatever the phase of growth studied.

Carbohydrate epitopes in breast milk are known to differ between species, with human milk expressing the most complex one. Gustafsson et al. (Glycoconjugate 22: 109-118 (2005)) investigated the expression of protein-bound carbohydrate epitopes in individual milk samples from man, cow, goat, sheep, pig, horse, dromedary and rabbit.

The glycan pattern found on SC is dependent on the host species, host organism, tissue of origin, and physiological status of the organism (e.g. health status, lactation phase).

Xu et al. (World J. Gastroenterol. 10(14) 2063-2066 (2004)) analysed the effects of fucosylated milk obtained from a transgenic goat. Human alpha1-2/4 fucosyltransferase gene was transiently expressed in goat mammary gland to produce "humanized" goat milk. The goat milk samples were found to inhibit bacterial binding to Lewis b antigen.

WO95/24495A1 describes the transgenic production of oligosaccharides and glycoconjugates in milk of transgenic mammals expressing human glycosyltransferase.

Grabenhorst et al. (Glycoconjugate Journal 1999, 16(2): 81-97) describe the genetic engineering of recombinant glycoproteins in frequently used host cells, e.g. transfection of CHO cells with gylcosyltransferases.

Porter P (Immunology 1973, 24(1) 163-176) describes the purification of porcine Secretory Component and secretory IgA from sow milk.

Gustafsson et al. (Glycoconjugate Journal 2005, 22(3) 109-118) describe the Lewis-type N-glycosylation of human and animal milk proteins.

The pIgR-pIg complex is transcytosed across the cell, and at the luminal surface the pIgR is cleaved by protease within a 42-amino acid region adjacent to the cell membrane thus releasing SIg into the lumen.

The cleaved extracellular portion of pIgR remains bound to pIg and is herein termed Secretory Component (SC). pIgR can also be transported into the mucosa even if pIg is not bound to it, thus most exocrine fluids contain SC both bound within SIg and also free SC.

The precise cleavage site is still ambiguous, as human SC was found to have a ragged C-terminus, varying from Ala-550 to Lys-559, with Ser-552 as the dominant C-terminal residue.

It is possible that additional proteolysis can occur after cleavage of the pIgR. The fact that free SC from different mucosal fluids appear to have slightly different molecular weights might suggest that proteolysis does occur in vivo after release of free SC from pIgR.

Free SC from colostrum has a molecular mass of approximately 76.5 kDa compared with approximately 80 kDa for bound SC to dIgA. The difference has been shown to stem from a difference in length of the polypeptide chain. There is, however, not a clear consensus about the C-terminal end of milk derived SC bound to polymeric immunoglobulin.

The generally larger size of SC in SIgA1 and SIgA2 compared to free SC may result from the presence of dimeric IgA in the former, which may shield the C-terminal linker of SC when the pIgR is cleaved after transcytosis. This shielding by dimeric IgA would be absent when free SC is cleaved in similar circumstances.

Human colostrum and milk are rich in both proteases and protease inhibitors. The ratio of inhibitor to protease defines whether active protease is present. The ratio changes markedly with the time after birth and appears to differ in different individuals. Since the free SC C-terminal linker peptide is highly susceptible to proteases, it might well be the case that there is no "correct" C-terminus for colostral and milk free SC. Moreover, the C-terminus for SC from other tissues than mammary gland (such as gut, bronchial, nasal tissues) may show different C-termini either because of different enzymatic cleavage from pIgR or because of the presence of different proteases trimming the free SC or pIg-bound SC.

One of the most important molecules for protection against infection of humans at mucosal sites (eyes, nose, mouth, lung, ears, traches, esophagus, gastric tract, intestine, urogenital tract and colon) is secretory IgA which may act both via its four antigen binding sites as well as via the glycan mediated binding of the Secretory Component.

Many studies demonstrate strong correlations between titers of specific SIgA antibodies in secretions and resistance to infection. Some studies demonstrate protection against systemic challenge with capsule forming bacterial pathogens.

Saliva and colostrum from normal subjects contain polyreactive SIgA antibodies which recognize a variety of autoantigens and several bacterial antigens. It has been suggested that these are products of B-1 cells, constituting part of the "natural antibody" repertoire encoded in the germline, and lacking memory capability and affinity maturation. These antibodies may provide protection of the mucosal surfaces prior to the generation of specific antibodies from conventional B-2-cells after exposure to nominal antigens. Although they have low intrinsic affinity for antigens, the presence of four antigen-binding sites in SIgA increases its functional activity. There is indeed evidence which suggests that bacterial adhesins have evolved because they are able to avoid recognition by these naturally occurring polyreactive antibodies.

In humans there are two unique IgA-subclasses (IgA1 and IgA2). Two or three allotypes of human IgA2 have been described (different combinations of constant region domains of the alpha-heavy chains). The predominant molecular form of circulating (plasma) IgA is monomeric, in contrast to the dimeric (polymeric) pIgA produced in epithelium and transported into the secretions as SIgA.

Human IgA1 and IgA2 (including allotypes) appear to have few, if any, distinct biologically properties but a notable exception is seen in the differences between IgA subclasses in their susceptibility to bacterial proteases. IgA1 and IgA2 also differ in the distribution of antibody specificities.

Immunization of adults with protein antigens elicits mainly IgA1 and immunization with polysaccharides provokes mainly an IgA2 antibody response. Of the immunoglobulin isotypes that reach mucosal surfaces, SIgA is one of the most stable and this stability has been largely ascribed to SC which masks potential cleavage sites within the Fc-portion.

The specificity of SIgA antibodies for surface structures of microbial surfaces to inhibit adherence to pharyngeal, intestinal, genitourinary tract and gingival epithelia was demonstrated. In addition to a specific, antibody-mediated inhibition of adherence, human IgA, and SIgA in particular, bind to many bacterial species and antigens by means of their carbohydrate chains. A notable example of this is seen in the case of IgA2, which can agglutinate E. coli by a mechanism involving the type I (mannose dependent) pili and type I pilus-dependent adherence of E. coli to epithelial cells.

IgM in external secretions is also associated with a Secretory Component (secretory IgM, SIgM) resulting from its transport into secretions by the pIgR. The concentration of SIgM is lower than that of SIgA either because of the lower proportion of IgM-producing cells in mucosal tissues or because IgM may be less well transported than pIgA due to a molecular weight restriction in pIgR-dependent transport.

Natural antibodies, by definition, are produced in the apparent absence of antigenic stimulation. They are produced by a specific subset of B-cells and do not extensively affinity mature. Natural antibodies of the classes IgA, IgM and IgG have been described. These antibodies are encoded usually by germline genes with few, if any, mutations and have in many cases broad reactivity against PAMPs (pathogen-associated molecular pattern), tumor antigens and a number of autoantigens. Because of their low affinity and germ-line configuration, such polyreactive antibodies do not appear to be true autoantibodies and certainly do not fit into the same category as antigen-specific, somatically-mutated, high affinity pathological autoantibodies.

Natural antibodies are considered as part of the innate immune system. They have been proposed for certain therapeutic uses, e.g. cancer therapy or in infectious diseases.

Many of the polyreactive antibodies have a germ-line or near germ-line sequence and are primarily IgM, but some are also IgG and IgA.

Contrary to the classic "lock and key" rigid structure hypothesis of antigen-antibody interaction, the antigen binding pocket of polyreactive antibodies, perhaps because of their germ-line configuration, are believed to be more flexible and therefore can accommodate different antigenic configurations.

Although some reports have suggested that SIgA is polyreactive in nature, other findings point to a restricted specificity that may be cross-reactive.

WO2009139624A1 discloses a process for producing compositions that are rich in secretory IgA by fractionating non-human milk. Such compositions may be used in particular for treating and/or preventing infections and/or inflammation of the mucosal surfaces, e.g. the gastro-intestinal tract, urogenital tract, respiratory tract, nasal cavity or oral cavity, treating and/or preventing obesity and related diseases, or treating and/or preventing food allergies in subjects in need of such treatment.

It is well known that human milk contains high amounts of Lewis-glycosylated glycoconjugates such as glycoproteins (such as SIgA and SC) and it is well accepted that one of the values of human milk is its high protective potency against infection by antibodies, glycans, oligosaccharides and other active substances such as lysozyme and lactoferrin. While the human milk analysis revealed a 75% fucosylation distribution, only 31% fucosylation distribution was observed in the bovine milk analysis. Only core fucosylation has been detected in the bovine milk analysis.

Though human secretory immunoglobulins with certain glycosylation have proven an advantageous effect with respect to binding to pathogen structures, mucins and receptors, they could not yet been produced on a large scale in a desirable quality. For ethical reasons human milk is typically not considered as a suitable source material.

SUMMARY OF THE INVENTION

It is the objective of the present invention to provide an improved method for producing a secretory immunoglobulin preparation of high quality on an industrial scale. It is further the objective to provide improved SC and immune complex preparations, particularly suitable for mucosal applications.

The objective has been solved by the subject matter of the claims.

According to the invention there is provided a method of producing an immune complex preparation based on a secretory immunoglobulin, which is non-human secretion derived, comprising
  providing an industrial scale production system, capable of producing an N-glycosylated Secretory Component,
  producing by such system a Secretory Component comprising at least 0.01 mol non-core fucose per mol of the Secretory Component, and
  combining said Secretory Component with at least one of IgA or IgM immunoglobulins having a native glycosylation pattern to obtain an immune complex, in particular a native N-glycosylation pattern. Such immune complex preparation is herein specifically understood as an innate immune complex preparation, which would specifically support the innate immune system of a mammal.

The non-core fucose specifically provides for the Lewis epitopes. Therefore, the immune complex according to the invention is herein also referred to as comprising at least 0.01 mol Lewis epitopes per mol of the Secretory Component. In most cases, however, the non-core fucosylation of the SC is determined in a suitable assay.

It is preferred that the production system is capable of producing Lewis-type N-glycosylated proteins, specifically a Secretory Component with peripheral or antennary, such as outer arm, fucosylation as determined by suitable analytical means, such as electrophoretic, chromatographic, mass spectroscopic, chemical and enzymatic techniques or combinations thereof.

Specifically the invention provides a Secretory Component which is derived from an amino acid or nucleotide sequence of mammalian origin, specifically human, cow, goat, sheep, non-human primates, pig, camel, dromedary, donkey or horse, or chimeric sequences thereof.

Specifically the method according to the invention employs a production system that is selected from pooled sources of mammary gland secretions and recombinant cell cultures.

In a specific embodiment said Secretory Component is derived from an amino acid or nucleotide sequence of a species, such as human, cow, goat, sheep, non-human primate, pig, mouse, rat, rabbit, dog, wallaby, possum, panda, fish, chicken, bird, frog, or chimeric sequences thereof. Preferably the Secretory Component is derived from an amino acid or nucleotide sequence of mammalian origin, specifically human, cow, goat, sheep, non-human primates, pig, camel, dromedary, donkey or horse, or chimeric sequences thereof.

In a preferred method the Secretory Component is enriched in a fraction of the production system, such as a milk fraction, and optionally isolated from said fraction. Specifically the Secretory Component preparation of the present invention is obtained from such enriched fraction. Specifically said Secretory Component is enriched in the fraction as immune complex.

According to a specific method, said Secretory Component is obtained from pooled sources selected from the group consisting of milk, milk concentrates, milk powders, whey, whey concentrates and whey powders, derived from at least 10 female individuals in the lactating phase.

Immune complex preparations according to the invention, if selected from a pool of secretions, such as milk, saliva, or mucosal excretions, specifically contain a mixture of SCs with varying C-termini.

Specifically said individuals are non-transgenic and of a species selected from the group consisting of goat, pig, cow, sheep, horse, donkey, dromedary and camel, with a preference of goat, pig, cow and sheep.

Preferably said individuals are selected from a population for the capability of producing glycoproteins with Lewis-type N-glycosylation. A specific selection can be made from a population or herd for the capability of expressing native N-glycosylated proteins, i.e. non-recombinant proteins. Such individuals would produce "human-like" SC, but not "humanized" milk, which would contain unnecessary changes in the glycosylation pattern. For example, such individuals are selected to produce native N-glycosylated proteins to express the immune complex with a native glycosylation pattern, including the Lewis epitopes on SC, specifically with non-core fucose or Lewis epitopes in the peripheral fucosylation, but not on N-glycosylation sites of immunoglobulin heavy chains.

Native glycosylated immunoglobulins only have core-fucosylated N-glycans. This is in contrast to immunoglobulins from transgenic animals expressing heterologous glycosyltransferases, which would result in an immunoglobulin preparation comprising surplus non-core or peripheral fucosylation and Lewis epitopes.

In an effort to obtain the immune complex preparation according to the invention with the native glycosylation pattern from a human being or animals, it is preferred that such preparation is based on non-recombinant proteins, or not obtained from such transgenic animals expressing heterologous glycosyltransferases.

Selections are made, for instance according to the capability of the individual mammal or cell to produce glycoproteins with Lewis-type N-glycosylation, in particular the non-core fucosylation or Lewis-type glycosylation on SC.

Preferably the relative content of non-core fucose is at least 0.01 mol/mol SC, preferably at least 0.02 mol/mol SC, more preferred at least 0.03, 0.04, 0.05, 0.06, 0.07, 0.08, 0.09, or 0.1 mol/mol SC, more preferred at least 0.2, 0.3, 0.4, or 0.5 mol/mol SC, even more preferred at least 1 mol/mol SC or even higher, e.g. at least 2 mol/mol SC, at least 3 mol/mol SC, at least 4 mol/mol SC, at least 5 mol/mol SC, at least 6 mol/mol SC, at least 7 mol/mol SC, at least 8 mol/mol SC, at least 9 mol/mol SC, or at least 10 mol/mol SC.

In specific cases the theoretical number of N-glycosylation sites amounts to 2 (fish), 3 (cow), 4 (horse, dog, rat) 5 (chicken, orang-utan, pig), 6 (chimpanzee, frog) or 7 (human, mouse, cartilaginous fish) mol/mol SC. According to the invention it is specifically preferred that the amount of non-core fucose or Lewis epitopes amounts to at least 1%, preferably at least 2, 3, 4, 5, 6, 7, 8, 9 or 10% of the theoretical value of N-glycosylation sites, more preferred at least 20%, 30%, 40%, 50%, 60%, 70%, 80% or 90% up to the theoretical value. The amount of non-core fucose may exceed the theoretical amount of N-glycosylation sites, e.g. through multiple fucosylation per N-glycosylation site, thereby obtaining more Lewis epitopes than the number of N-glycosylation sites on a molar basis. In specifically preferred cases, the amount of non-core fucose or Lewis epitopes is at least 1.1-fold, preferably at least 1.2 fold, or at least 1.3 fold, at least 1.4 fold, at least 1.5 fold, at least 1.6 fold, at least 1.7 fold, at least 1.8 fold, at least 1.9 fold, or at least 2 fold, in specific case, the amount is even higher, e.g. at least 3-fold, or at least 4-fold, or at least 5-fold, or at least 6-fold, or at least 7-fold, or at least 8-fold, or at least 9-fold, e.g. up to 10-fold the theoretical amount of N-glycosylation sites.

While the lower threshold, e.g. of at least 0.01 mol non-core fucose per mol SC, reflects the high quality of an SC preparation in particular of cattle or ruminants, a higher threshold, e.g. of at least 0.1 or at least 0.5, even at least 1.0 mol/mol may be applicable to the high quality of an SC preparation obtained from sources like horse, donkey or pig.

The degree of non-core fucosylation in a preparation may be increased by selection for SC with a high non-core fucosylation (per mol of SC). This can be done at the level of selection of a production host (such screening for a cell line, a microbial clone or an organism), or it can be done on the level of individual donors which are selected to provide secretions containing SC with a high molar non-core fucosylation for subsequent pooling of these samples. The fucosylation can be increased by enzymatic or chemical fucosylation of a preparation of SC or an immune complex of the invention.

According to a specific embodiment, the SC and/or the immunoglobulin is obtained from pooled sources comprising the SC and/or the immunoglobulin of the desired quality, which are provided as intermediates. Such intermediates may be selected from pooled and dried milk or whey powder, e.g. lyophilized or spray-dried, or plasma pools or pooled plasma fractions containing plasma immunoglobulin. The intermediates may then be further processed to enrich the SC and/or the immunoglobulin fraction, e.g. at least 10 fold, preferably at least 20 fold or even higher.

A specific preparation according to the invention enriched in SC and/or SIgA specifically comprises at least 20% SC and/or SIgA, or at least 30%, or at least 40%, or at least 50%, (w/w total protein).

Though the SIgA or SIgM immune complex is preferably not completely obtained from recombinant sources such as transgenic animals or genetically engineered cells, in particular with respect to the IgA or IgM component of the immune complex, which is preferably non-recombinant, according to a specific embodiment the Secretory Component may be obtained from a recombinant host cell, e.g. obtained from a host cell expressing autologous or heterologous N-glucosyltransferases and especially fucosyltransferases, preferably a recombinant production host cell line expressing autologous or heterologous functional alpha-1, x-fucosyltransferase, wherein x is 2, 3 or 4, preferably selected from the group consisting of human cell line, mammalian cell line, avian cell line, bacteria, plant, yeast, insect, fungal, moss and archaea.

According to a specific aspect, the invention provides for an isolated recombinant Secretory Component comprising the amino acid sequence of SEQ ID 1, or a functionally active variant thereof, which has a Lewis-type N-glycosylation pattern and at least 2 mol non-core fucose per mol Secretory Component. Specifically, the recombinant SC comprises a human SC sequence, or a sequence of human SC origin. According to a preferred embodiment, the recombinant SC is a human SC, or a functionally active variant thereof.

Specifically, the recombinant Secretory Component of the invention comprises sialic acid, preferably at least 2 mol sialic acid per mol Secretory Component. More specifically the recombinant SC comprises at least 2 mol sialyl Lewis x per mol SC.

Alternatively, the recombinant Secretory Component of the invention is non-sialylated, preferably comprising less than 0.1 mol sialic acid per mol Secretory Component.

Recombinant SC can be produced by introduction of either the complete gene of pIgR, e.g. human pIgR, into a host cells, subsequent expression of the transmembrane protein pIgR followed by a cleavage and release of the extracellular part, the SC, into the culture supernatant. An alternative expression is the transcription of the nucleotide sequence of the SC, i.e. only the extracellular domains, such as encoding the amino acid sequence of SEQ ID 1. In all cases, the expression of recombinant SC allows for exact selection of production conditions that guarantee a homogeneous C-terminus of the final product.

It also allows choosing the translation termination site according to the needs. Preferably the stop codon on the SC gene to be expressed is located between coding for the last extracellular immunoglobulin-like domain (domain 5) and the transmembrane region. However, the recombinant SC of the invention may be even shorter as long as it is able to bind to polymeric immunoglobulin and contain the required level of non-core fucose.

The first 18 amino acids in SEQ ID 1 comprise the signal peptide which may be replaced by a different signal peptide depending on the host cells or organisms used and the secretion efficiency required. For production by chemical synthesis or intracellular production of SC the signal peptide is not required (e.g. for production of the non-glycosylated form in $E.\ coli$ inclusion bodies). The protein may also be modified to contain additional amino acids at the C-terminus of SEQ ID 1.

The protein may be terminated by a stop codon at the required position in the nucleic acid respectively after the codon for amino acid G545, preferably at any amino acid site between K566 and E607 (including these sites), more preferred between R603 and E607 (including these sites), or after E607. Most preferably, the SC is terminated after R603. Numbering refers to SEQ ID 1.

Preferably, the SC preparation of the invention is homogeneous, wherein at least 80%, or at least 90%, or at least 95%, up to 100% of the SC molecules have the same C-terminus.

The glycan pattern of the recombinant SC is dependent on the host species, the host organism, the tissue of origin and the physiological state of the genetically engineered cell.

Preferably the host cell is selected from the group consisting of human cells such as PerC.6, Chinese Hamster Ovary cells, Baby Hamster Kidney cells, murine cells, avian cells lines, bacterial, yeast fungal, plant and insect cells. A recombinant SC may be obtained with the desired non-core fucosylation or Lewis-type N-glycosylation. Preferably the host cells are selected or modified to express the required glycosyltransferases to produce non-core N-glycosylation fucosylation. The non-core fucosylation may be introduced or increased after expressing recombinant SC, e.g. by enzymatic or chemical or chemoenzymatic techniques.

The degree of non-core fucosylation in a preparation of the invention may be increased by selection for SC with a high non-core fucosylation (per mol of SC). This can be done at the level of selection of a production host (such screening for a cell line, a microbial clone or a transgenic organism), it can also be done on the level of individual donors which are selected to provide secretions containing SC with a high molar non-core fucosylation for subsequent pooling of these samples. The fucosylation can be introduced or increased by enzymatic or chemical fucosylation of a preparation of SC or an innate immune complex of the invention.

Preferably the relative content of Lewis x epitopes on SC as used according to the invention is at least 0.01 mol/mol SC, preferably at least 0.02 mol/mol SC, more preferred at least 0.03, 0.04, 0.05, 0.06, 0.07, 0.08, 0.09, or 0.1 mol/mol SC, more preferred at least 0.2, 0.3, 0.4, or 0.5 mol/mol SC, even more preferred at least 1 mol/mol SC or even higher, e.g. at least 2 mol/mol SC, 3 mol/mol SC, 4 mol/mol SC, 5 mol/mol SC, 6 mol/mol SC, 7 mol/mol SC, 8 mol/mol SC, 9 mol/mol SC, or at least 10 mol/mol SC.

A specifically preferred isolated recombinant SC, e.g. in a recombinant SC preparation, has a Lewis-type N-glucosylation pattern and at least 2 mol non-core fucose per mol Secretory Component.

Specifically it comprises at least 2 mol Lewis x epitopes per mol SC, in some cases at least 6 mol/mol.

Specifically it comprises sialic acid, preferably at least 2 mol sialic acid per mol Secretory Component. Specifically, it comprises at least 2 mol sialyl Lewis x per mol Secretory Component.

Alternatively, recombinant SC is specifically non-sialylated, preferably comprising less than 0.1 mol sialic acid per mol Secretory Component.

According to a specific aspect there is provided an immune complex preparation comprising a recombinant Secretory Component of the invention, and at least one of IgA or IgM immunoglobulins, preferably human immunoglobulins. Specifically, the immunoglobulins are plasma immunoglobulins, e.g. derived from human blood plasma or a blood plasma fraction.

According to the invention there is further provided an immune complex preparation based on a secretory immunoglobulin, derived from sources other than human secretions, comprising
  a Secretory Component with a non-core fucosylation or Lewis-type N-glucosylation pattern and at least 0.01 mol Lewis epitopes per mol Secretory Component, and
  at least one of IgA or IgM immunoglobulins having a native glycosylation pattern.

The preparation according to the invention specifically comprises a polymeric immunoglobulin, such as a dimeric, or pentameric or other polymeric immunoglobulin, e.g. dimeric SIgA or pentameric SIgM. Preferably the immunoglobulin is obtained from animal milk, colostrum or any of milk or colostrum fractions or concentrates and blood plasma or fractions thereof.

Specifically the preparation according to the invention comprises a polyreactive immunoglobulin, preferably a natural immunoglobulin, including germline antibodies.

According to a specific embodiment there is further provided a formulation comprising the isolated or purified (recombinant) Secretory Component of the invention or an immune complex preparation of the invention, in the form of a liquid, emulsion or suspension or in the dried form, preferably spray-dried or freeze-dried.

The formulation according to the invention specifically may be provided in the form of a natural formulation like a dairy product, where the immune complex is provided in the natural context, such as milk, or milk products such as cheese, yoghurt, whey, whey concentrate, or else a synthetic formulation that comprises the isolated or purified SC or immune complex. Specifically the formulation according to the invention may be provided in the form of a liquid, syrup, lozenge, tablet, such as an effervescent tablet, a spray, inhalator formulation, powder, instant powder, granules, suppository, capsules, cream, paste, gel, drops, suspension, emulsion, or food product, including dairy products and chewing gum.

Preferably the formulation is a formulation for mucosal use, in particular for oral use.

According to a further specific embodiment, the invention provides for the isolated or purified (recombinant) Secretory Component of the invention or an immune complex preparation of the invention or a formulation of the invention, for use in the therapy or prophylaxis of immunoglobulin deficiency, e.g. e.g. selective IgA deficiency, selective IgM deficiency, or CVID, in particular mucosal immunoglobulin deficiency, preferably in a formulation for mucosal application, preferably oral, bronchial, nasal, vaginal, intragastric or rectal use.

Therefore, the invention further provides for a respective method of treatment or prevention of mucosal immunoglobulin deficiency, by administering an effective amount of the compounds or compositions of the invention to a subject in need thereof.

Subjects—in particular human subjects—may be in need for treatment of transient, acquired and chronic immunodeficiency, e.g. being at risk of or suffering from mucosal immunoglobulin deficiency, and thus, eligible to such treatment, e.g. to normalize and/or elevate the level of SIgA and/or SIgM in the mucosa, e.g. as determined in mucosal samples, or indirectly in blood.

Specific therapeutic indications are, for instance, infectious diseases, such as of the naso-pharyngeal tract, urogenital tract, eyes and gastric tract, e.g. bacterial overgrowth in the proximal small intestine, recurrent urinary tract infections or chronic bronchopulmonary infections.

A preferred use is the prevention of a disease or disorder caused by a pathogen, including microbial substances or organism, antigens or disease causing agents, such as toxins.

Specifically, the subject is treated that is at risk of or suffering from infections, allergies, e.g. a subject at risk of or suffering from allergic symptoms, and autoimmune diseases. Specifically, the subject is suffering from IgA and/or IgM deficiency, including selective IgA and/or IgM deficiency, SIgA deficiency and/or SIgM deficiency, and specifically a combined secretory IgA/IgM deficiency.

According to a further specific aspect, the subject is treated with an oral preparation, e.g. to provide a single-dose of 10 mg to 10 g SIgA and/or SIgM, e.g. a preparation wherein either of the SIgA or the SIgM is contained in an amount of 10 mg to 10 g per administration unit, e.g. as the predominant immunoglobulin, or a combination of the SIgA and SIgM in the amount of 10 mg to 10 g in total.

The formulation according to the invention may particularly be provided for use as a food product and/or for therapeutic use. Specifically the formulation may be provided as a dietary supplement, nutritional management food, food additive or medical food.

FIGURES

FIG. 1 shows the amino acid sequence of human Secretory Component

FIG. 2 shows the nucleic acid sequence of the human Secretory Component including cloning sites at the 5' and 3' ends FIG. 3 shows the amino acid sequence of alpha 1,2-fucosyltransferase (FUT2)

FIG. 4 shows the gene for alpha 1,2-fucosyltransferase (FUT2) with respective cloning sites (underlined)

FIG. 5 shows the protein sequence of fucosyltransferase 3

FIG. 6 shows the gene for fucosyltransferase 3 with respective cloning sites (underlined, italic)

FIG. 7 shows the amino acid sequence of beta 1,3-galactosyltransferase I

FIG. 8 shows the gene for beta 1,3-galactosyltransferase I with respective cloning sites (underlined, italic)

FIG. 9 shows the amino acid sequence of beta 1,3-galactosyltransferase V

FIG. 10 shows the gene for beta 1,3-galactosyltransferase V with respective cloning sites (underlined, italic)

FIG. 11 shows the amino acid sequence of beta 1,3-galactosyltransferase II

FIG. 12 shows the gene for beta 1,3-galactosyltransferase II with respective cloning sites (underlined, italic)

FIG. 13 shows the protein sequence of chimeric anti-nitrophenyl IgA heavy chain (small letters=leader peptide, underlined=murine VH)

FIG. 14 shows the DNA sequence of the chimeric anti-nitrophenyl IgA heavy chain construct, including HindIII and XbaI restriction sites (underlined)

Figure 16:
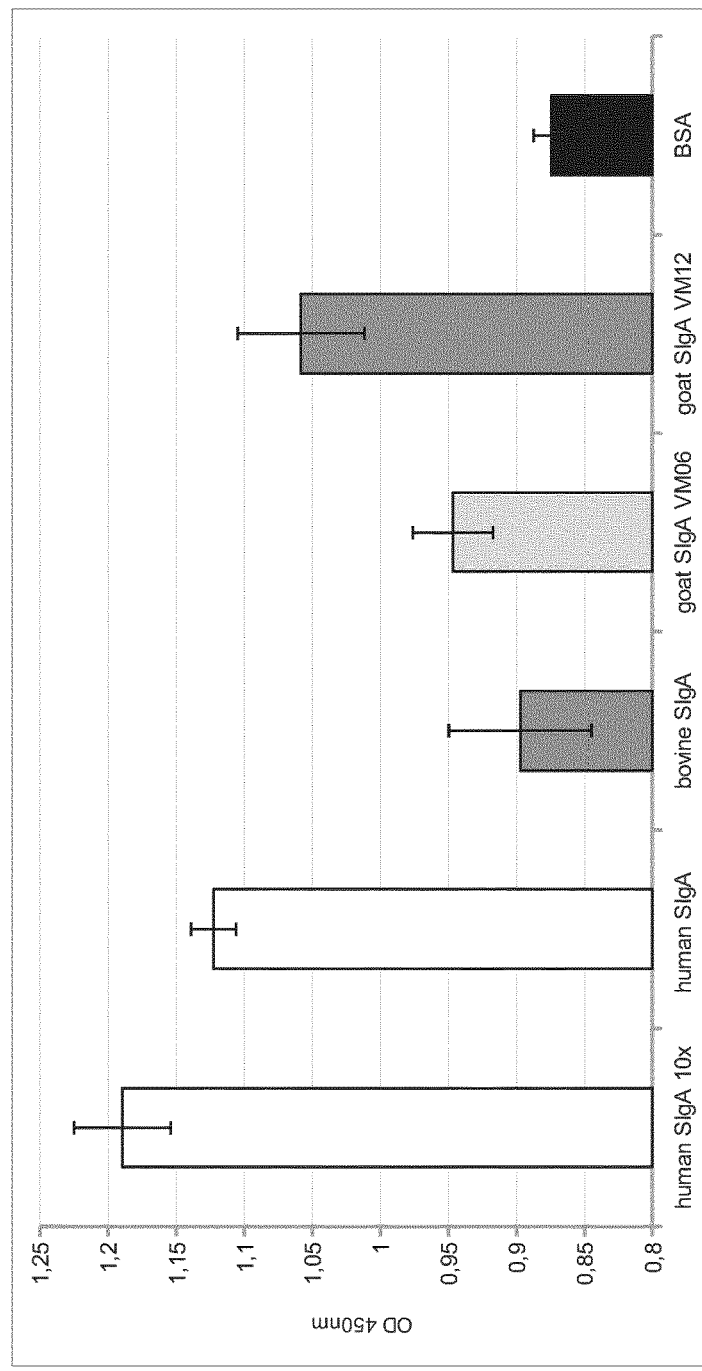

FIG. 16 shows the reduction of cytotoxicity of *Clostridium difficile* Toxin A upon incubation with preparations of secretory immunoglobulin. Two SIgA preparations of individual goats with different non-core fucosylation are tested in comparison with a bovine SIgA sample, each of them in an amount equimolar to the toxin. As a positive control, human SIgA is used in an equimolar amount and in a tenfold higher amount. As a negative control, bovine serum albumin (BSA) is used.

Figure 17:
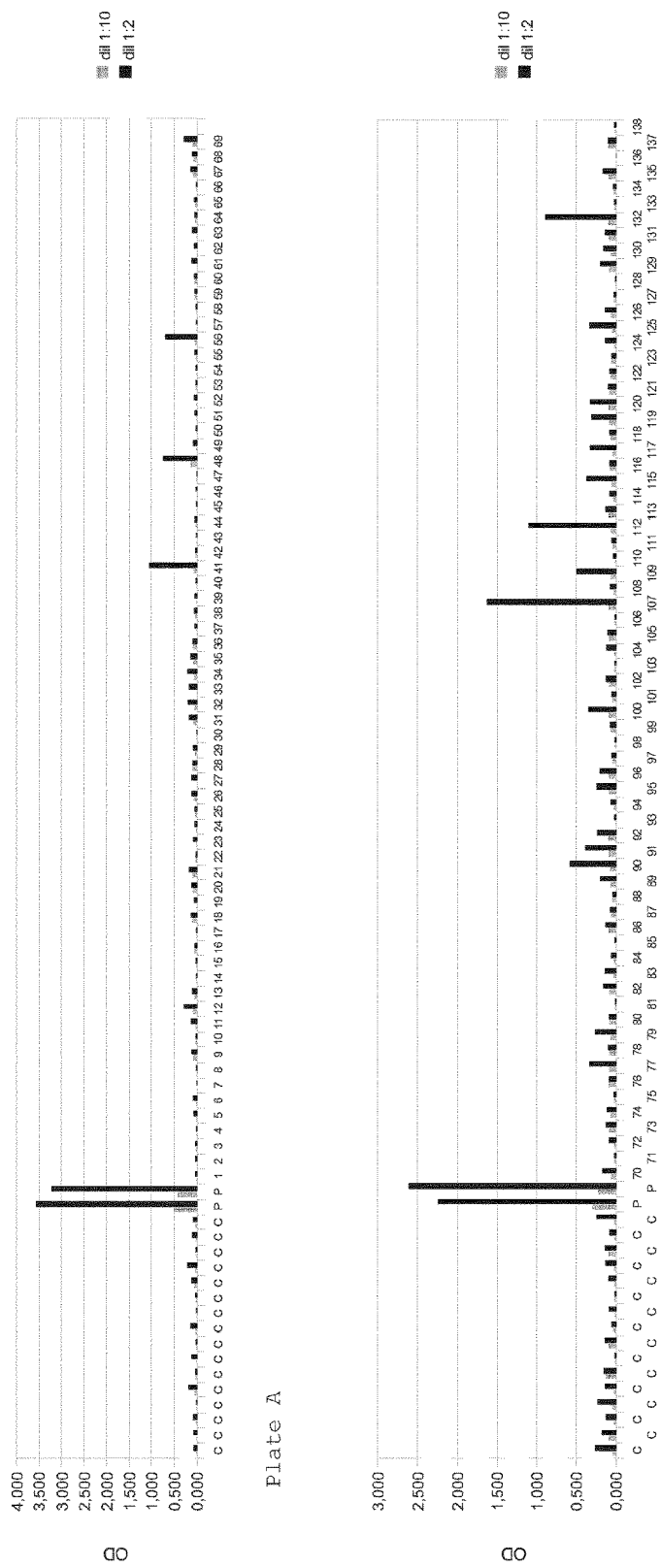

FIG. 17 shows the results of screening of SIgA preparations obtained from milk of individual animals. In the ELISA assay the non-core fucosylation of SIgA is determined by the Lewis-specific glycosylation binding to the lectin DC-SIGN. As a positive control, SIgA from human milk is used. As a negative control, SIgA from commercial goat milk (pooled without screening milk from individual animals) is used.

DETAILED DESCRIPTION OF THE INVENTION

The term "human-like" or "humanized" as used herein with respect to a Secretory Component (SC) or immune complex preparation shall refer to a human SC, e.g. recombinant human SC, or derived from other species, but not derived from human secretions, such as human milk. The humanized SC is specifically engineered or selected to obtain a SC preparation with a N-glycosylation pattern comprising non-core fucose or Lewis epitopes. Specifically a "human-like" or "humanized" SC or immune complex is preferred comprising a human-like or humanized SC, which is either obtained from non-human secretions of mammary gland and selected for the high degree of glycosylation with Lewis epitopes, or obtained as a recombinant SC based on a sequence of human origin or a humanized sequence with a fucosylation pattern comprising the desired Lewis epitopes. The humanized SC specifically comprises peripheral, antennary or outer arm fucosylation (summarized under the term "non-core fucosylation"), which proved to confer an anti-pathogen effect and specific receptor binding properties (e.g. binding to DC-SIGN on dendritic cells).

A "humanized" SC or immune complex as described herein differs from a "humanized" milk obtained from transgenic animals, essentially in that it has a selected high level of Lewis epitopes on the SC, and still a native N-glycosylation pattern on other glycoproteins, such as immunoglobulins, so to avoid surplus fucosylation, specifically excess peripheral fucosylation. Accordingly, the immunoglobulins in the immune complex have a native glycosylation pattern, e.g. a native N-glycosylation pattern with only core fucosylated N-glycans.

The term "native" as used herein with respect to the glycosylation pattern of immunoglobulins, in particular IgA and/or IgM, shall mean the glycosylation produced by B cells of a mammal, which is specifically characterized by the glycosylation without non-core fucosylation, and specifically without Lewis epitopes. Lewis epitopes are typically not produced by native or unmodified B-cells of a mammal.

The term "non-core fucosylation" or "Lewis epitopes" as used herein shall refer to glycan antennae with fucosylation, in particular at non-core positions, including peripheral, antennary or outer arm fucosylation. It specifically refers to epitopes of a Lewis antigen or H-type antigen recognisable by a specific immunoglobulin or antibody. Lewis epitopes may be presented by Lewis blood group antigens, including Lewis x (LeX), Lewis y (LeY), Lewis b (LeB) and Lewis a (LeA) antigens. The term "Lewis epitopes" shall also refer to H-type I and H-type II antigens as well as blood antigens A and B. The Lewis antigens may be further modified, e.g. by sialic acid, to form e.g. sialylated Lewis epitopes. The Lewis antigens may be sialylated and/or sulfated. Preferred Lewis epitopes stem from LeX and sialylated LeX antigens.

Reference to a specific "non-core fucosylation" with respect to SC as made herein shall refer to a SC glycoprotein preparation, e.g. isolated recombinant SC or isolated from pooled sources, e.g. milk or milk fractions. It therefore applies to a preparation comprising individual SC molecules, each having a specific glycosylation pattern, such as having one or more outer antennary (or non-core) fucose residues attached to it. The SC glycosylation is thus determined in the preparation as described herein.

For purposes of illustration and not limitation, a recombinant SC may be expressed in a genetically engineered (modified) CHO cell as described herein, and the majority of individual SC molecules may have a non-core fucose residue on a specific N-glycosylation site of the SC. Such "non-core fucosylation" can be characterized in a variety of ways. Reference is in each case made to a relatively high (or increased) number of the SC glycoprotein molecules of the population having non-core fucose residues on it as compared to a population of the SC glycoprotein molecules made in a cell line that lacks a modification in accordance with the invention.

A specific non core fucosylation of the Secretory Component may also be produced by enzymatic and/or chemical addition of fucose to a site showing low or no non-fucosylation before addition.

Another way to characterize a SC glycoprotein preparation according to the invention is by the ratio of non-core fucosylation to overall glycosylation in the isolated Secretory Component produced. A recombinant Secretory Component according to the invention has a ratio of non-core fucosylated N-glycosylation:overall N-glycosylation that is about 1:1 through 1:5, 1:5 through 1:10, 1:10 through 1:30, 1:30 through 1:100.

Another way to characterize an isolated recombinant Secretory Component is the relative amount of epitopes formed by non-core fucose residues (fucosylated blood group structures) to glycan component of the SC glycoprotein.

The term "native glycosylation pattern" as used herein with respect to IgA and IgM, shall refer to an N-glycosylation pattern found in the heavy chains of IgA or IgM, which essentially does not contain Lewis epitopes, but only core fucosylation, if any. Though the native glycosylation pattern of glycoproteins differs from species to species, there is a typical range of glycosylation properties within a population within a species, such as the theoretical number and positions of carbohydrate sites. Secretory immunoglobulins of animals such as cows, goats and sheep, normally have a similar glycosylation pattern within a species in terms of theoretical glycosylation sites.

Still, the percentage of actually glycosylated sites within a glycosylation pattern was found to range from 0 to 100%, mainly depending on parameters like race, age, family, feeding, lactating phase, health status, physiological status and milk processing.

The term "non-core fucosylation pattern" or "Lewis-type N-glycosylation pattern" as used herein with respect to the SC as used according to the invention, shall refer to a glycosylation pattern comprising N-linked fucose and Lewis epitopes at non-core positions, e.g. peripheral, antennary or outer arm positions. During glycosylation, either N-linked or O-linked glycoproteins are formed. N-linked glycoproteins constitute the majority of cell-surface proteins and secreted proteins. The Lewis blood group structures are formed by certain fucosylation of antennary glycans. For example, the Lewis x and Lewis a structures are (Gal-beta1-4)(Fuc-alpha1-3) GlcNac and (Gal-beta1-3) (Fuc-alpha1-4) GlcNac, respectively. These structures can be further sialylated (NeuAca2,3-) to form the corresponding sialylated structures. Other Lewis blood group structures of interest are the Lewis y and Lewis b structures which are (Fuc-alpha1-2)Gal-beta1-4 (Fuc-alpha1-3)GlcNAc and (Fuc-alpha1-2)Gal-beta-1-3 (Fuc-alpha1-4) GlcNAc, respectively. Further Lewis epitopes are from H-type I and H-type II antigens ((Fuc-alpha1-2)Gal-beta1-3GlcNac and (Fuc-alpha1-2)Gal-beta1-4GlcNac respectively) and blood antigens A and B ((GalNAc-alpha1-3)Fuc-alpha1-2Galβ1-3GlcNAc and (Gal-alpha1-3)Fuc-alpha1-2Galβ1-3GlcNAc respectively). For a description of the structures of the ABO and Lewis blood group structures and the enzymes involved in their synthesis, see Ma et al., 2006, Glycobiology vol. 16, no. 12 pp 158R-184R.

Exemplary non-core fucosylation or Lewis-type N-glycosylation pattern of the SC are described as follows:

An N-glycan (N-linked oligosaccharide, N-(Asn)-linked oligosaccharide) is a sugar chain covalently linked to an asparagine residue of a polypeptide chain, commonly involving a N-acetylglucosamine (GlcNAc) residue and the consensus peptide sequence: Asn-X-Ser/Thr. N-Glycans share a common pentasaccharide core region and can be generally divided into three main classes: oligomannose (or high-mannose) type, complex type, and hybrid type.

In vertebrate N-glycans, the main core modification is the addition of fucose in an alpha1-6 linkage to the N-acetylglucosamine adjacent to asparagine in the core (=core fucosylation).

The majority of complex and hybrid N-glycans have elongated branches that are made by the addition of a β-linked galactose residue to the initiating N-acetylglucosamine to produce the ubiquitous building block Galbeta1-4GlcNAc, referred to as a type-2N-acetyllactosamine or "LacNAc" sequence. Antennae can be further lengthened by the sequential addition of e.g. N-acetylglucosamine and galactose residues.

The most important "capping" or "decorating" motifs involve sialic acid, fucose, galactose, N-acetylgalactosamine, and sulfate on the branches. All those fucose-residues are herein referred to as non-core fucose-residues: The Lewis blood group and related antigens are a set of glycans that carry alpha1-2, alpha1-3, alpha1-4 fucose residues or a combination thereof. The A, B, and H determinants blood group determinants on type-1 and type-2 blood group antigens display fucose in alpha1-2 linkage.

The following specific structures are considered as "non-core fucosylation" on SC: glycans that carry alpha1-2, alpha1-3, alpha1-4 fucose residues or a combination thereof, Lewis a, Lewis b, Lewis x, Lewis y, the A, B, and H determinants blood group determinants on type-1 and type-2 blood group antigens and sialylated and/or sulfated forms thereof.

The maximum or theoretical number of Lewis epitopes of a glycoprotein may be equal or exceeding its number of glycosylation sites as there may be multiple Lewis epitopes per N-glycosylation site, e.g. by branching, extensions and repeats of structures. For example, a human SC has 7 gylcosylation sites, thus, a more than 7 Lewis epitopes are possible. Since a Lewis epitope may comprise one or more non-core fucose, the number of non-core fucoses may exceed the number of Lewis epitopes in a glycoprotein.

In specifically preferred cases, the amount of non-core fucose or Lewis epitopes is at least 1.1-fold, preferably at least 1.2 fold, or at least 1.3 fold, at least 1.4 fold, at least 1.5 fold, at least 1.6 fold, at least 1.7 fold, at least 1.8 fold, at least 1.9 fold, or at least 2 fold, in specific case, the amount is even higher, e.g. at least 3-fold, or at least 4-fold, or at least 5-fold, or at least 6-fold, or at least 7-fold, or at least 8-fold, or at least 9-fold, e.g. up to 10-fold the theoretical amount of N-glycosylation sites.

Lewis-type N-glycosylation may be conferred by respective fucosyltransferases, which have been used in synthetic pathways to transfer a fucose unit from guanosine-5'-diphosphofucose to a specific hydroxyl of a saccharide acceptor. Heterologous fucosyltransferases may be expressed by recombinant organisms to express fucosylated glycoproteins.

The term "immune complex" as used herein shall refer to a protein complex comprising at least one immunoglobulin molecule bound to a Secretory Component through non-covalent or covalent linkage. Non-covalent associations comprise, for example, electrostatic or hydrophobic interactions. Within an immune complex according to the invention there is provided at least one IgA and/or at least one IgM molecule, which may be covalently bound to further immunoglobulins, such that polymeric immunoglobulins are formed. In nature, such multimerization occurs either through the J-chain of polymeric antibodies or by other, non-covalent interactions.

The term "industrial scale" shall refer to the large scale production of immune complexes, from natural sources or recombinant expression systems, including cell cultures. The industrial scale expression system as described herein preferably has a proven productivity of at least 10 mg of immune complex per liter, preferably 100 mg per liter, and a preferred volume of at least 100 liters, more preferably of at least 1000 liters, e.g. through pooled sources.

The term "innate" with respect to an immune complex shall refer to an immune complex governing or stimulating the innate immune response or function in animals, including mammals, among them human subjects or patients. While an innate immune complex according to the invention may support the immune defence against pathogens in a relatively non-specific way, it may as well specifically recognise epitopes of particulate or dissolved antigenic substances.

The term "isolated" or "purified" with respect to proteins, such as the SC or the immune complex according to the invention, as used herein refers to a protein which is obtained from a complex mixture of an animal's body fluid or secretions, thus, of natural origin, or of cell cultures, like a cell culture supernatant or a tissue or cell extract. Those proteins are typically at least 50% pure, preferably at least 60% pure, more preferably at least 70% pure, even more preferably at least 80% pure, most preferably at least 90% pure, and even most preferably at least 95% pure, as determined by SDS-PAGE.

The term "Secretory Component" or "SC" as used herein shall refer to a Secretory Component that may be secreted by a mammary gland of an animal, including humans, or variants thereof, including functional variants, which SC is e.g. a glycoprotein separate from an immunoglobulin or in complex with an immunoglobulin, e.g. to form a secretory immune complex, e.g. mediated by the J-chain (or variants thereof) or other structures of immunoglobulins that bind specifically to the polyimmunglobulin receptor (pIgR). An SC may be obtained from natural sources, such a colostrum or milk, or else produced synthetically or by recombinant expression techniques.

The SC as used herein is specifically non-core fucosylated, as further described herein. In addition, the glycosylation pattern may or may not comprise sialyl epitopes.

Specifically, the SC is provided either as sialylated or asialylated protein preparation. Preferably the ratio between sialylated and asialyl-glycans as provided according to the invention is in a highly sialylated preparation preferably at least 3:1, preferably at least 4:1, or at least 5:1, or at least 6:1, or at least 7:1. The ratio in a preparation of low sialylation, including non-sialylated (asialylated) proteins, herein also understood as an asialylated preparation, is less than 1:3, preferably less than 1:4, or less than 1:5, or less than 1:6, or less than 1:7. Preferably the SC as provided in such preparation contains either only asialylated glycans or sialylated glycans.

Preferably the relative content of sialyl-Lewis x epitopes on recombinant SC is at least 0.02 mol/mol SC, more preferred at least 0.03, 0.04, 0.05, 0.06, 0.07, 0.08, 0.09, or 0.1 mol/mol SC, more preferred at least 0.2, 0.3, 0.4, or 0.5 mol/mol SC, even more preferred at least 1 mol/mol SC or even higher, e.g. at least 2 mol/mol SC, 3 mol/mol SC, 4 mol/mol SC, 5 mol/mol SC, 6 mol/mol SC, 7 mol/mol SC, 8 mol/mol SC, 9 mol/mol SC, or at least 10 mol/mol SC. A specifically preferred SC preparation comprises at least 2 mol sialyl-Lewis x epitopes per mol SC, in some cases at least 6 mol/mol.

The SC and immune complex of the present invention have the advantage of a more homogeneous glycosylation which can improve mucosal effects, e.g. the homogeneous glycosylation is due to less different glycoforms despite of having a high degree of non-core fucosylation, e.g. less than 20 different SC glycoforms, or less than 10 different SC glycoforms, or even less than 5 different SC glycoforms.

While the primary function of secretory immunoglobulin appears to be promoting exclusion of antigens and pathogens, there is evidence that a fraction of secreted antibody is actually transported "retrograde," back into the mucosa.

There is evidence that SIgA is endocytosed following association with DC-SIGN on the cell surface of dendritic cells (DCs). Based on these results it was proposed that DC-SIGN may serve as the receptor on mucosal DCs involved in the recognition and internalization of SIgA, and possibly SIgA-antigen complexes.

It is well known that binding of secretory immunoglobulin to DC-SIGN is mediated by the glycans of the Secretory Component. DC-SIGN recognizes a range of oligosaccharide ligands, including mannan, complex high mannose-containing glycoconjugates, and asialyated Lewis blood group antigens.

In order to enhance the binding of an immune complex to dendritic cells via DC-SIGN, it is advantageous to use SC with a low sialylation grade but with high non-core fucosylation for the secretory immunoglobulin preparation. Such a minimally sialylated or even asialylated SC may be utilized to produce monoclonal or polyclonal polymeric immunoglobulin preparations which bind to antigens that the organism should be tolerized to (e.g. dietary antigens, allergens).

On the other hand, it may be advantageous to provide a secretory immunoglobulin preparation that does not bind to dendritic cells via DC-SIGN, or which has a lower efficacy in binding to DC-SIGN. This may be accomplished by utilizing a highly sialylated non-core fucosylated SC for the preparation of the innate immune complex of the invention. Such a preparation may be utilized to enhance the decoy effect of secretory immunoglobulin with regards to certain viruses, toxins and other pathogen structures.

Sialyl Lewis x is determinant constitutively expressed on granulocytes and monocytes and mediates inflammatory extravasation of these cells.

The presence or absence of sialyl Lewis x on the immune complex of the invention may increase the efficacy or decrease side effects of treatments with an immune complex of the invention by to interfering or avoidance of interference with an inflammatory situation.

The degree of sialylation in a preparation may be increased or decreased by selection for SC with a high or low molar sialylation (per mol of SC) respectively. This can be done at the level of selection of a production host (such as a cell line, a microbial clone or an organism), it can be done on the level of individual donors which are selected to provide secretions containing SC with a high or low molar sialylation respectively for subsequent pooling of these samples. The sialylation can be increased or decreased by enzymatic or chemical sialylation and desialylation respectively of a preparation of SC or an innate immune complex of the invention.

For the absolute quantification of sialic acids of a glycoprotein sample (mol sialic acids/mol glycoprotein) a glyco-analysis procedure based on mass spectroscopy may be applied. Alternatively, a colorimetric method as described in the monograph 1316 of the European Pharmacopoeia for erythropoietin may be used. This method is based on Svennerholm, 1957, Biochim Biophys Acta. Vol 24, pp 604-11.

Accordingly, a pure preparation of a defined amount of SC is treated with resorcinol and hydrochloric acid at 100° C., the blue complex formed is separated with butyl alcohol/butyl acetate, followed by photometric measurement at 580 nm. The photometric readings are converted into a mass by a calibration curve produced with sialic acid.

The term "secretory immunoglobulin" as used herein shall refer to an immunoglobulin that may be secreted by a mammary gland of an animal including humans, e.g. mediated by the pIgR or variants thereof, including functional variants. A secretory immunoglobulin may be obtained from natural sources, such as colostrum or milk, in particular as an SIgA and/or SIgM, or else produced synthetically or by recombinant expression techniques or by a combination of polymeric immunoglobulin from natural sources such as blood plasma and a recombinant SC or by a combination of polymeric immunoglobulin produced by recombinant expression techniques and a SC from natural sources such as milk or other body fluids.

The term "recombinant" as used herein refers to proteins (including polypeptides) produced by genetic engineering or gene recombination techniques employing a recombinant expression system, like host organisms, such as prokaryotes or eukaryotes, in a contained reactor system such as microbial fermentation or cell culture, e.g. employing a production host cell line or strain like a yeast, fungi, bacteria or archaea, a cell line, from mammalian cells, insect cells, plant cells or respective tissues.

The term "expression system" or "production system" as used herein shall refer to organisms like cell cultures or higher eukaryotic organisms, like selected lactating animals, however, not including human beings, capable to produce proteins and immune complexes of the desired quality and quantity. Preferred systems employ expression vectors for use in a eukaryotic host.

"Expression vectors" or "vectors" as used herein are defined as DNA sequences that are required for the transcription of cloned recombinant nucleotide sequences, i.e. of recombinant genes and the translation of their mRNA in a suitable host organism. Such expression vectors may comprise an origin for autonomous replication in the host cells, selectable markers (e.g. an essential amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together.

The term "eukaryotic host" shall mean any eukaryotic cell, tissue or organism, which may be cultivated to express a protein. Specifically, the eukaryotic host is a eukaryotic host cell line. It is well understood that the term does not include human beings. Preferred hosts to express the SC according to the invention are eukaryotic hosts.

The term "host cell" or "host cell line" refers to a microorganism or a cell line, used for expression of a recombinant gene to produce the recombinant proteins as used according to the invention. Preferred host cells are selected from the group consisting of mammalian, avian, insect or plant cells, yeasts, filamentous fungi or bacteria. For producing the Secretory Component of the invention host cells capable of producing glycoproteins with non-core fucosylation or Lewis-type N-glycosylation are preferably used. A host cell clone of cultivated host cells that have proliferated is commonly understood to be a host cell line. A production host cell line is commonly understood to be a cell line ready-to-use for cultivation in a bioreactor to obtain the product in an industrial scale.

The term "polymeric immunoglobulin" as used herein shall refer to an association of at least 2, 3, 4, 5 or even a higher number up to 10 immunoglobulin molecules. The polymeric immunoglobulin is thus, considered an at least dimeric immunoglobulin, e.g. dimeric IgA, trimeric, quatromeric, pentameric, such as SIgM, hexameric immunoglobulin or even higher polymers or aggregates. Polymeric immunoglobulins may comprise the immunoglobulin molecules associated with each other by covalent bonding, or other interactions, like electrostatic, hydrophobic, ionic interactions or affinity binding with or without J-chain.

The term "polyreactive immunoglobulin" as used herein shall refer to an immunoglobulin with at least two specificities, meaning that it recognises at least two different epitopes, also known as cross-reactivity. Typically, polyreactive immunoglobulins of an innate immune system would have at least 3, 4, 5 or more relevant (e.g. with regard to physiologically relevant or pharmacologically active) specificities to bind epitopes and antigens, most commonly with low or medium affinities.

The term "food" or "food product" shall comprise any compound, preparation, mixture, or composition suitable for, or intended for intake by an animal. This includes any compound that is a nutritional, nutraceutical or food supplement, dietary food or supplement or medical food which is understood as nutritional or functional supplement to a food product, possibly used as a diet. Typically, functional food products aid in the prevention or prophylaxis and/or treatment of disease conditions associated with pathogens, including toxins or the treatment of physiological imbalances of the body. The term shall also comprise feed or feed products, possibly used as a diet for feeding non-human animals. Food may be of organic or synthetic sources, formulated in natural or natural-like compositions including dairy products or synthetic compositions based on artificial mixtures of substances, which have been suitably purified before mixing. The food product according to the invention typically is provided in food grade quality. The grade quality is the quality characteristics of food that is acceptable to animals. This includes external factors as appearance (size, shape, colour, gloss, and consistency), texture and flavor. Quality standards also provide for an acceptable maximum amount of contaminating substances. Besides ingredient quality, there are also sanitation requirements to inactivate or deplete pathogens. It is important to ensure that the food processing environment is as clean as possible in order to produce the safest possible food for the consumer.

The term "variant" or "functionally active variant" of a protein like the Secretory Component or an immunoglobulin, as used herein means a sequence resulting from modification of the parent sequence by insertion, deletion or substitution of one or more amino acids or nucleotides within the sequence or at either or both of the distal ends of the sequence, and which modification does not affect (in particular impair) the activity of this sequence. In a preferred embodiment the variant is a functionally active variant, which a) is a biologically active fragment of the amino acid or the nucleotide sequence, the functionally active fragment comprising at least 50% of the sequence of the amino acid or the nucleotide sequence, preferably at least 60%, preferably at least 70%, more preferably at least 80%, still more preferably at least 90%, even more preferably at least 95% and most preferably at least 97%, 98% or 99%; b) is derived from the amino acid or the nucleotide sequence by at least one amino acid substitution, addition and/or deletion, wherein the functionally active variant has a sequence identity to the amino acid or the nucleotide sequence or to the functionally active fragment as defined in a) of at least 50%, preferably at least 60%, preferably at least 70%, preferably at least 80%, still more preferably at least 90%, even more preferably at least 95% and most preferably at least 97%, 98% or 99%; and/or c) consists of the amino acid or the nucleotide sequence and additionally at least one amino acid or nucleotide heterologous to the amino acid or the nucleotide sequence, preferably wherein the functionally active variant is derived from or identical to any of the naturally occurring variants of any of the sequences found in various gene and protein databases. Such functionally active variants are specifically preferred that comprise a preferred glycosylation pattern as described herein, specifically the Lewis-type N-glycosylation pattern and the non-core fucosylation of the SC. Further preferred functionally active variants are characterized by their ability able to bind to polymeric immunoglobulin, e.g. IgA dimers or IgM pentamers, to form a secretory immune complex.

Most SC sequences are described as complete polyimmunoglobulin receptors (pIg R), for the purpose of the invention only the extracellular part of these sequences are relevant, e.g.: the sequence of human SC as provided in SEQ ID 1, or sequences comprised in or essentially identical to the following:

UniProtKB: locus PIGR_BOVIN, accession P81265 (bovine pIgR)

UniProtKB: locus PIGR_HUMAN, accession P01833 (human pIgR)

UniProtKB: locus PIGR_RAT, accession P15083 (rat pIgR)

UniProtKB: locus PIGR_MOUSE, accession 070570 (mouse pIgR)

UniProtKB: locus PIGR_RABIT, accession P01832 (rabbit pIgR)

NCBI REFSEQ: accession NM_174143.1 (bovine pIgR)
embl accession X81371.1 (bovine pIgR)
GenBank GenBank: DAA21480.1 (bovine pIgR)
GenBank: AAI49033.1 (bovine pIgR)
NCBI REFSEQ: accession XM_537133.2 (bovine pIgR)
NCBI Reference Sequence: NP_002635.2 (human pIgR)
NCBI Reference Sequence: NP_035212.2 (mouse pIgR)
NCBI Reference Sequence: NP_036855.1 (rat pIgR)
GenBank: AAK69593.1 (wallaby pIgR)
NCBI Reference Sequence: NP_001125098.1 (orangutan pIgR)
GenBank: EAW93516.1 (human pIgR)
GenBank: EAW93515.1 (human pIgR)
NCBI Reference Sequence: NP_999324.1 (pig pIgR)
GenBank: BAJ20784.1 (human pIgR)
NCBI Reference Sequence: XP_001083307.2 (macacca pIgR)
NCBI Reference Sequence: XP_002760783.1 (Callithrix pIgR)
GenBank: AAD41688.1 (possum pIgR)
GenBank: EDM09843.1 (rat pIgR)
GenBank: AAI10495.1 (human pIgR)
GenBank: AAI10496.1 (human pIgR)
NCBI Reference Sequence: XP_514153.2 (Chimpanzee pIgR)
GenBank: AAC53585.1 (mouse pIgR)
GenBank: AAQ14493.1 (chicken pIgR)

NCBI Reference Sequence: NP_001038109.1 (chicken pIgR)
  GenBank: AAP69598.1 (chicken pIgR)
  GenBank: AAW71994.1 (chicken pIgR)
  GenBank: AAH13556.1 (mouse pIgR)
  GenBank: EDL39729.1 (mouse pIgR)
  GenBank: CAA76272.1 (mouse pIgR)
  GenBank: BAA24431.1 (mouse pIgR)
NCBI Reference Sequence: NP_001164516.1 (rabbit pIgR)
NCBI Reference Sequence: XP_001492348.2 (horse pIgR)
  GenBank: AAC41620.1 (bovine pIgR)
  GenBank: AAB23176.1 (human pIgR)
  GenBank: AAB20203.1 (human pIgR)
  GenBank: ABK62772.1 (*xenopus* pIgR)

"Percent (%) amino acid sequence identity" with respect to the polypeptide sequences identified herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithm as needed to achieve maximal alignment over the full length of the sequences being compared.

The functionally active variant may be obtained by sequence alterations in the amino acid or the nucleotide sequence, wherein the sequence alterations retain a function of the unaltered amino acid or the nucleotide sequence, when used in combination of the invention. Such sequence alterations can include, but are not limited to, (conservative) substitutions, additions, deletions, mutations and insertions.

A functionally active SC variant may be obtained by exchange of domains between SC from different species, or by deletion or addition of domains. Changing of the natural order of the domains (e.g. 1-2-3-4-5 for mammalian SC) may also result in a functionally active variant (e.g. 1-4-3-2-5).

In a specific embodiment of the invention the polypeptide or the nucleotide sequence as defined above may be modified by a variety of chemical techniques to produce derivatives having essentially the same activity (as defined above for fragments and variants) as the modified polypeptide or the nucleotide sequence, and optionally having other desirable properties, like reactivity, N-glycosylation sites and stability (in vivo or in vitro stability). Desirable properties are, for example, the increase in thermostability and/or gastrointestinal stability, as measured by the pH stability and/or protease (e.g. pancreatic) stability of the protein. The glycosylation pattern of the immunoglobulin can affect numerous aspects of the SC therapeutic efficacy such as solubility, resistance to proteolytic attack and thermal inactivation, immunogenicity, half-life, bioactivity and stability, or ability to bind to polymeric immunoglobulin.

Variants of the SC of the invention may have altered amino acid sequences to introduce additional glycosylation sites. A preferred embodiment of the invention is the addition of N-glycosylation sites. This can be achieved by genetic engineering techniques as well as chemical and enzymatic means. Introduction of the sequence motif Asn-Xaa-Thr-Xaa (Seq. ID No. 15) or Asn-Xaa-Ser-Xaa (Seq. ID. No. 16) (in which Xaa is any amino acid but Proline) into various sites of SC may allow for selection of functionally active variants with improved characteristics (e.g. stability, binding to pathogen structures, binding to pIg). It may allow for a human-derived SC to have more than 7 glycosylation sites.

The variant of the polypeptide or the nucleotide sequence is functionally active in the context of the present invention, if the activity of the composition of the invention including the variant (but not the original) amounts to at least 50%, preferably at least 60%, more preferred at least 70%, still more preferably at least 80%, especially at least 90%, particularly at least 95%, most preferably at least 99% of the activity of the immunoglobulin or SC as used according to the invention including the amino acid or the nucleotide sequence without sequence alteration (i.e. the original polypeptide or the nucleotide sequence).

Functionally active variants may be obtained by changing the sequence as defined above and are characterized by having a biological activity similar to that displayed by the respective sequence from which the variant is derived or similar to human SC, including the ability of modifying the immune response to pathogens, the binding to pathogen structures and other molecules.

Still, the term "functionally active variant" includes naturally occurring allelic variants, as well as mutants or any other non-naturally occurring variants. As is known in the art, an allelic variant is an alternate form of a (poly)peptide that is characterized as having a substitution, deletion, or addition of one or more amino acids that does essentially not alter the biological function of the polypeptide.

In a preferred embodiment, the functionally active variant derived from the amino acid or the nucleotide sequence as defined above by amino acid exchanges, deletions or insertions may also conserve, or more preferably improve, the activity.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

The term "mucosal immunoglobulin deficiency" shall mean a concentration of immunoglobulins present in mucosal samples below the normal or reference range. This specifically refers to the content of either SIgA or SIgM or a combination of both SIgA and SIgM.

The term "secretory IgA deficiency" or "SIgA deficiency" is a deficiency in secretory IgA. The term "secretory IgM deficiency" or "SIgM deficiency" is a deficiency in secretory IgM.

These secretory immunoglobulin deficiencies may be caused by genetic disposition, chemicals, or by local disturbance of SIg production in the mucosa-associated lymphoid tissue (MALT) e.g. by stress, malnutrition, injury or surgery.

MALT is understood in man as e.g.
  GALT (gut-associated lymphoid tissue. Peyer's patches are a component of GALT found in the lining of the small intestines.)
  BALT (bronchus-associated lymphoid tissue)
  NALT (nose-associated lymphoid tissue)
  LALT (larynx-associated lymphoid tissue)
  SALT (skin-associated lymphoid tissue)
  VALT (vascular-associated lymphoid tissue)
  EALT (eye-associated lymphoid tissue made up of Conjunctiva [CALT] and Lacrimal Duct [LDALT] associated lymphoid tissues)

SIgA deficiency may be associated with SIgM deficiency.

Detection of secretory IgA and/or secretory IgM deficiency is done by measurement of SIgA and/or SIgM in secretions such as saliva, cervical mucus, nasal mucus, gastric juice, sweat, urine or stool by standard immunoassay techniques or by molecular biology techniques. Immunological detection of SIgA and/or SIgM in secretions can be performed by ELISA, RIA, by fluorescence based immune assays, time-resolved fluorometry, precipitation assays, nephelometric assays, surface plasmon resonance based assays and similar setups with and without labels. An important requirement is the detection of the Secretory Component bound to the immunoglobulin molecules in order to be able to discriminate SIgA and/or SIgM from IgA and/or IgM.

Molecular biological detection of SIg deficiency can be performed by assaying for the expression of J-chain and/or pIgR in respective tissues and cells, either at the protein level with antibodies, specific for those molecules or on the genetic level with probes specific for the genes of those molecules. Both RNA and DNA may be investigated. Methods for detection can be assays based on hybridization with or without template amplification (such as PCR) or signal amplification.

A mucosal SIgA deficiency may be a strong indicator of general secretory IgA deficiency. A mucosal SIgM deficiency may be a strong indicator of general secretory IgM deficiency. A combined mucosal SIgA/SIgM deficiency is a strong indicator of a combined general secretory IgA and IgM deficiency.

An SIg deficiency is particularly indicated if the level of mucosal SIg is less than 50% as compared to a reference value, which is either a normal value or a value of healthy subjects of the same type, specifically less than 40%, 30%, 20% or 10%.

There is considerable variation in the levels of secretory immunoglobulins in different individuals. An exact measurement of the immunostatus of an individual may first establish the baseline of usual SIgA and/or SIgM values for the individual over a period of days to weeks during a period of good health and low to moderate physical activity. The baseline may also vary with the age of the individual. However this method is not feasible for individuals with chronic secretory immunodeficiency. Therefore, reference values for normal populations may be considered as well.

For humans, the normal salivary SIgA level is 11-65 mg/dL, normal salivary SIgM level is 1 mg/dL. Normal SIg values are typically determined in samples of healthy subjects. Decreased salivary immunoglobulin may be present in children with recurrent upper respiratory infection, selective IgA and/or IgM deficiency and occasionally in individuals with food allergies.

SIgA deficiency in human saliva samples as determined by immunoassays is typically indicated if the SIgA concentration is less than 100 milligram SIgA per liter or a salivary SIgA flow rate of less than 50 micrograms SIgA per minute or an SIgA to albumin ratio of less than 4 (as proposed by Dwyer et al. in Aviation, Space, and Environmental Medicine, 2010, volume 81, pages 582 ff). SIgA-deficiency in human faeces as determined by immunoassays is typically indicated if the SIgA concentration is less than 10 milligram per 100 g of faeces.

SIgA deficiency in human tears as determined by immunoassays is typically indicated if the SIgA concentration is below 50 mg SIgA per milliliter.

SIgM deficiency in human nasal secretions or saliva as determined by immunoassays is typically indicated if the SIgM concentration is less than 50 mg per liter in nasal secretions and/or an SIgM concentration is less than 1 mg/dL in saliva.

The decreased level of SIg needs to be found in only at least one compartment of the mucosa-associated lymphoid tissue in order to qualify for SIg deficiency.

SIgA deficiency occasionally may be determined in a sample wherein a SIgM deficiency was also determined. Thus, the preparation of the present invention comprising both SIgA and SIgM is preferably used in a subject at risk of SIgA and SIgM deficiency.

The term "mucosal" with respect to an immunoglobulin deficiency refers to the level of the immunoglobulin as determined in mucosal samples, such as samples taken from a subject's saliva, gastric juice, cervical mucus, nasal mucus, gut lavage, gastric juice, bronchial lavage, urine, tears and faeces.

The term "mucosal" with respect to administration or application or else mucosal use of a preparation for treating a subject or a respective formulation, refers to administration via the mucosal route, including systemic or local administration, wherein an active ingredient is taken up by contact with mucosal surfaces. This includes oral, nasal, vaginal, rectal bronchial administration and formulations, e.g. liquid, syrup, lozenge, tablet, such as an effervescent tablet, a spray, inhalator formulation, powder, instant powder, granules, suppository, capsules, cream, paste, gel, drops, suspension, emulsion, or food product, including dairy products and chewing gum.

The term "subject" as used herein refers to any animal, which herein preferably includes mammals and particularly human, for whom diagnosis, screening, monitoring or treatment is contemplated. A subject may be at risk of a certain disease condition, e.g. a patient afflicted with a disease condition or for which a disease condition is to be determined or risk of a disease condition is to be determined. The term "patient" as used herein always includes healthy subjects. In some embodiments, the methods disclosed herein may include selecting a subject in need of an SIg supplemental therapy, such as a subject with proven SIg deficiency, and further treating said subject according to the invention.

The term "at risk of" a certain disease conditions, such as SIg deficiency or mucosal immunoglobulin deficiency refers to a subject that potentially develops such a disease condition, e.g. by a certain predisposition, or already suffers from such a disease condition at various stages, including the congenital or acquired state, including transient disease, particularly associated with other causative disease conditions or else conditions or complications following as a consequence of such immunoglobulin deficiency.

The risk determination and diagnosing a mucosal Ig deficiency is particularly important in a subject, where the Ig deficiency has not yet been diagnosed. This risk determination therefore includes early diagnosis to enable prophylactic therapy.

Specifically the preparation of the invention is used in patients with a high risk, e.g. a high probability of a mucosal Ig deficiency without symptoms (e.g. children below 4 years, persons shortly before and after surgery, before and after extensive physical stress such as high performance sports or work, or when traveling with an increased risk of infection with pathogens).

The risk assessment and in particular the treatment of mucosal Ig deficiency according to the invention is particularly indicated with infectious diseases of the mouth, throat, nose and ears, the eyes and esophagus, the gastric and colon tract.

A further preferred use is the prevention of a disease condition caused by a pathogen, including microbial substances or organism, antigens or disease-causing agents, such as toxins. For example, hospitalised patients may need to supplement their immune system to reduce the risk of a hospital-acquired infection. Neonatal humans or animals receiving a food supplement according to the invention may have a higher chance of survival in case that they cannot obtain sufficient breast milk from mothers or respective wet nurses. Furthermore, the risk of enteropathogenic disease in animals and humans may be reduced by a food product according to the invention. Specifically, where a subject is suffering from SIg deficiency, pathogens may induce a hypertoxic effect, i.e. a disease condition upon challenging with a dose of a disease causing agent, which would otherwise not cause such disease condition. The preparation according to the invention is, thus, specifically provided to prevent such hypertoxic effect in subjects at risk of or suffering from SIg deficiency.

Therefore, the present invention refers to a new method of producing an immune complex preparation as described above, which has the great advantage of providing a stable, high quality preparation in sufficient quantities through the industrial scale production. New preparations of recombinant SC and immune complexes are provided with improved quality.

Thereby an innate immune complex may be provided, which is specifically useful as a food product, a wellness product to restore and maintain a balanced physiology or for medical purposes, including therapeutic and prophylactic uses.

It turned out that non-core fucose, specifically Lewis glycans, play an important role also as part of the innate immunity of organisms. The elucidation of the interactions between pathogen structures such as surface antigens, toxins or receptors and glycan structures of the host is studied in detail.

In particular, Lewis glycosylation may interact with *Helicobacter pylori* attachment to host cells. More than 80% of *H. pylori* strains express Type II Lewis antigens (LeX and/or LeY), and half of them express both. A smaller proportion of *H. pylori* strains express Type I Lewis blood group antigens (LeA and/or LeB) and a very small number express sialyl-LeX.

Similarly, sialyl-LeX is expressed on the cell surface of some oral bacteria that are associated with infected endocarditis, such as *Streptoccocus pyogenes, Porphyromonas gingivalis, Actinobacillus actinomycetemcomitans* and *Eikenella corrodens*.

Noroviruses are causative agents of e.g. acute gastroenteritis. They bind to histo-blood group antigens (HBGAs) on host cells, namely, ABH antigens and Lewis antigens, in which type 1 and type 2 carbohydrate core structures constitute antigenically distinct variants. Human noroviruses recognize sialyl Lewis x neoglycoprotein.

*Clostridium difficile* toxin A and intimin of enteropathogenic *E. coli* are binding to galactosyl and/or sialic acid residues of SC. It has been shown that DC-SIGN on mucosal dendritic cells acts as a putative receptor for SIgA, and that dendritic cells could thus collaborate with M cells in immune surveillance at mucosal surfaces.

This invention is predicated on the discovery that a human-like glycosylation of an SC can be found in selected individuals of non-human species, and that such human-like SC is preferentially used in combination with a native immunoglobulin which has the native glycosylation pattern that is useful to stabilize the human-like SC and preserve the natural functions of a secretory immunoglobulin. It turned out that the glycosylation pattern of SC within the same species varies in a broad range, thus, large pools of donations that are typically used for preparing milk products would not contain a significant level of N-glycosylation with Lewis-epitopes on the isolated SC. Such common large scale pools would not be useful as source material for the purpose of the invention. In some individuals, however, the SC can have human-like, high level of Lewis epitopes. Those individuals would qualify to prepare large production pools that can be used as a source material for manufacturing the immune complex according to the invention in the large scale. Alternatively the respective human-like SC may be produced by recombinant production methods. The SC obtained from the source material is then combined with IgA or IgM, specifically including polymeric immunoglobulin molecules having a native glycosylation pattern, in particular those comprising immunoglobulin chains that are non-core fucosylated. The polymeric immunoglobulins can be derived from natural sources such as milk or blood plasma or be produced recombinantly. Alternatively, immune complexes of the invention comprising the SC and the immunoglobulin can be directly isolated and purified from large production pools, e.g. selected for their content of non-core fucose or Lewis epitopes. Thus, the immune complex preparation may be prepared, which comprises the stabilized SC to the extent that it provides for the storage-stable product or immune complex preparation with an increased stability in vivo, resulting in an increased recovery in the mucosa and/or half-life.

Glycosylation variations may occur at a different physiological state of the cell or organism producing the SC, e.g. infections, presence of inflammatory factors, food and nutrition supply, stress etc. A further source of variation of glycosylation in a mixture may be a different genetic background and makeup of the individual organisms or cells producing SC (such as species, race, blood groups, pIgR genotype and haplotype, etc.). Suitable analytical methods to determine the glycosylation pattern are e.g. described by Deshpande et al. (J. Proteome Res. 2010, 9, 1063-1075).

Human milk contains Lewis epitopes, also milk from pig, horse and other species is reported to contain glycoproteins with Lewis-antigens. Mammalian α1,2- and α1,3/4-fucosyl-transferases are involved in the last steps of synthesis of A, B, and H Lewis blood group antigens and Lewis-blood group-related carbohydrate antigens (i.e., LeX, LeY, LeA, LeB, sialyl-LeX, and sialyl-LeA). Still, it was not possible to provide for the non-core fucosylated or Lewis glycosylated SC or SC immune complex with immunoglobulins on an industrial scale.

It is surprisingly possible to identify individual expression systems, such as cell clones or animals, recombinant organisms or microorganisms which produce significantly more of the non-core, Lewis-fucosylated SC versus core-fucosylated SC than the average in the heterogeneous mixture of SC glycoforms (free or bound to immunoglobulins). The difference between individual clones or animals can be unexpectedly high.

It is a surprising finding that non-core fucosylation plays a role in binding of recombinant SC to *Clostridium difficile* Toxin A. This is in contrast to Perrier et al. 2006 J Biol. Chem. vol. 281(20), pp. 14280-14287 who concluded that fucose residues are not involved in the association.

Another surprising finding is that the level of certain glycosylation motifs may correlate with the potency of SC to neutralize certain pathogen antigens.

A further surprising finding is that the level of binding to the receptor DC-SIGN varies strongly between individual milk samples and that the binding of SC to DC-SIGN is influenced by Lewis glycans despite the presence of complex high mannose-containing glycans.

In order to provide for the human-like SC, non-human milk may be used as a source of improved SC. SC or an immune complex isolated from milk samples of individual animals is analyzed for its molar content of non-core fucose or Lewis-eitopes. The animals may or may not have been immunized against certain human or veterinary pathogens to provide hyperimmune milk.

The animal may be prescreened for the likelihood to produce more of SIgA or more of a certain glycosylation by genetic means, e.g. by assays for expression of pIg-receptor, assays for pIgR haplotypes, and/or certain fucosytransferase genes, e.g. FUT3, 4, 5, 6, 7, 9, 10, 11 and/or other glycosyltransferases (e.g. beta-3-galactosyltransferase or beta-4-galactosyltransferase) and a population may be bred for such purposes.

Such animals are then identified and selected for the suitable expression products.

The expression product comprising the non-core fucosylated or Lewis-fucosylated SC as described above is then preferably pooled and used as a source for the preparation of the immune complex according to the invention.

Actually the human-like SC as used according to the invention, which is from sources other than human breast milk, has similar or even improved properties as compared to the human natural SC with a broad spectrum neutralization activity towards many pathogens. As used herein the term "pathogen" always includes microbial organisms and toxins, also including bacterial, fungal, viral and protozoan cells and products, in particular human or veterinarian pathogens.

It is preferred that the preparation according to the invention comprises a high titre of a relevant mix of immunoglobulins maintaining their native function including the mucosal passage after oral ingestion.

The immune complex preparation according to the invention has the advantage of high potency due to the standardized high amount of non-core fucose or Lewis epitopes in the N-glycosylation pattern of the SC. Thereby the anti-pathogenic effect, including anti-microbial or antitoxin effect, of the immune complex preparation can be significantly increased.

The main selection criteria relate to the type and quantity of the Lewis epitopes that have proven to confer the desired immunity. Preferred Lewis epitopes are LeB epitopes, which are significantly increased over the average prevalence in natural sources. Also preferred is the occurrence of Lewis x and sialylated Lewis x epitopes on SC. The preferred relative increase in a milk derived product is at least an increase in ELISA signal that exceeds the signal of a pooled source from unselected individuals, which pool size derives from at least 100 individuals by a factor of 2 times the standard deviation of non-selected samples. Typically a pool of mammary gland products derived from at least 100 individuals, in particular of ruminants, such as cow, sheet or goat, has an average of significantly below 0.01 mol non-core fucose or Lewis epitopes/mol SC, usually below 0.005 mol/mol, in most cases even undetectable Lewis-antigens as determined by standard ELISA techniques.

The present invention, however, provides for the preferred selection of individuals, individual samples or pools of mammary gland secretions, culture supernatants or cell extracts according to their quality with respect to the non-core fucose or Lewis epitopes, which are at least 0.01 mol/mol SC, and specifically at least 1%, preferably at least 5% or at least 10% non-core fucose or Lewis epitopes of the theoretical value. The even more preferred selection is performed according to higher non-core fucose or Lewis glycosylation levels, for instance, at least 0.01 mol/mol SC, preferably at least 0.02 mol/mol SC, more preferred at least 0.03, 0.04, 0.05, 0.06, 0.07, 0.08, 0.09, or 0.1 mol/mol SC, more preferred at least 0.2, 0.3, 0.4, or 0.5 mol/mol SC, even more preferred at least 1 mol/mol SC or even higher, e.g. at least 2 mol/mol SC, at least 3 mol/mol SC, 4 at least mol/mol SC, or at least 5 mol/mol SC, at least 6 mol/mol SC, at least 7 mol/mol SC, at least 8 mol/mol SC, at least 9 mol/mol SC, or at least 10 mol/mol SC. In specific cases the theoretical number of N-glycosylation sites amounts to 2 (natural bovine SC), 3 (natural equine SC) and 7 (natural human SC) mol/mol. According to the invention it is specifically preferred that the selection is performed according to the amount of Lewis epitopes which are at least 1%, preferably at least 2, 3, 4, 5, 6, 7, 8, 9 or 10% of the theoretical number of glycosylation sites, more preferred at least 20%, 30%, 40%, 50%, 60%, 70%, 80% or 90% up to the theoretical number of glycosylation sites.

The amount of non-core fucose may exceed the theoretical amount of N-glycosylation sites, e.g. through multiple fucosylation per N-glycosylation site, thereby obtaining more Lewis epitopes than the number of N-glycosylation sites on a molar basis, e.g. at least 1.1-fold, preferably at least 1.2 fold, or at least 1.3 fold, at least 1.4 fold, at least 1.5 fold, at least 1.6 fold, at least 1.7 fold, at least 1.8 fold, at least 1.9 fold, or at least 2 fold, in specific case, the amount is even higher, e.g. at least 3-fold, or at least 4-fold, or at least 5-fold, or at least 6-fold, or at least 7-fold, or at least 8-fold, or at least 9-fold, e.g. up to 10-fold the theoretical amount of N-glycosylation sites.

Selections may be performed on the basis of the determination of samples from individuals or from selection pools, i.e. pooled samples, wherein the pool is derived from 10 or more individuals. Material which has proven to be non-core fucose or Lewis-positive according to the selection criteria may then be pooled to provide a production pool as a source material to be used for the industrial scale production of the immune complex preparation according to the invention. The production pools having a proven high quality glycosylation profile, have a preferred size of at least 10, more preferred at least 50, 100, 500, 1.000 or 2.000 donations, or preferably at least 10, 50, 100, 500, 1000, 2000, 10,000 or 20,000 Liters. As a quality control measure usually the presence of the relevant glycosylation is confirmed by in-process controls and/or end product controls. The end product typically is standardized according to the desired glycosylation pattern.

Exemplary test systems for determining non-core fucose on SC and/or SIgA or SIgM are described in the examples section below. A highly sensitive determination method refers to glycan analysis by standard RP-ESI-MSMS (also termed RP-HPLC-ESI-MSMS, reverse phase—high performance liquid chromatography—electrospray ionization—tandem mass spectroscopy). The level or degree of non-core fucose or Lewis-type fucosylation may be tested based on the following principle:

The glycan profile and hence the amount of a certain composition of the oligosaccharides attached to a given glycosylation site may be determined by mass spectrometry of glycopeptides derived from the SC (Stadlmann 2008, Proteomics 8, 2858-2871; Wuhrer 2007, Proteomics 7, 4070-4081). In the particular case of fucose-residues attached to the antennae of glycans (Lewis glycosylation) on SC with several potential glycosylation sites, the following strategy can be applied.

The SIgA-preparation is separated on a SDS-PAGE and the SC-band is eluted. The SC is S-alkylated and digested with trypsin or another suitable protease. The sample is additionally subjected to treatment with a fucosidase capable of specifically removing fucose residues in alpha-1,6-linkage to the innermost GlcNAc residue (core-fucosylation). An example of such an enzyme is the fucosidase from bovine kidneys.

The resulting mixture of peptides and glycopeptides is then analyzed by mass spectrometry, preferably after chromatographic separation by, e.g. reversed-phase chromatography. With proper choice of the protease, the chromatography column and the solvent gradient, each glycosylation site is then represented by a peak. The potential sites of Asn-linked glycosylation can be deduced from the amino acid sequence of the protein.

As the retention on most reversed-phase columns, e.g. on a Waters BioBasic C18 column, relies solely on the peptide moiety, this peak covers all glycoforms of a given peptide and hence glycosylation site.

The glycopeptides of a given site can be identified by several means:

1.) Due to the usually observed heterogeneity, they form a series of peaks differing by the mass of e.g. a hexose (162.05 Da) a sialic acid (291.09 Da), an N-acetyl-hexosamine (203.08 Da) or a fucose residue (146.06 Da).

2.) MSMS fragmentation by ESI- or MALDI-MS can reveal the sequence of the glycans and the mass of the underlying peptide 3.) Enzymatic removal by peptide: N-glycosidase (either F or A) will generate the deglycosylated peptide containing a Glu (glutamic acid) instead of a Gln (glutamine) residue, which results in a mass difference of 1 Da. The mass of this deglycosylated peptide must match the assumptions obtained or used in points 1.) and 2.).

Once the glycopeptide peaks are identified, the peak "volume", i.e. the area under the peaks corresponding to a particular glycopeptide species is measured by a suitable method, which can take into account that one analyte often occurs in two or more charge states. The peak volume can be translated directly into molar proportions of glycoforms as the ionization and hence detection of the glycopeptides is dominated by the peptide portion (Stadlmann, 2008, Proteomics 8, 2858-2871).

From the list of glycoforms occurring on a particular site, the molar fraction of fucosylated glycans is calculated. The results for the different sites are added to arrive at the molar proportion in which a particular structural feature occurs on the particular SC sample. The completeness of the core-fucose removal can be verified e.g. by analysis of the released N-glycans by chromatography on porous graphitic carbon with MS detection (Pabst 2007, Anal. Chem. 79, 5051-5057).

For screening a large number of individual sources or preparations, a simple and rapid assay, such as a lateral flow assay may be used. In addition or alternatively, an ELISA assay is used employing a Lewis-type glycosylation specific ligand, such as antibodies or alternative scaffold binders against various Lewis epitopes (e.g. anti-Lewis a, anti-Lewis b, anti-Lewis x, anti-Lewis y, anti-sialyl Lewis x), the human lectin DC-SIGN, the Dendritic Cell-Specific Intercellular adhesion molecule-3-Grabbing Non-integrin, also known as CD209 (Cluster of Differentiation 209). Examples of other lectins binding to Lewis epitopes possibly used are isolectin A, *Aleuria aurantia* agglutinin, thrombomodulin, langerin, scavenger receptor C-type lectin, E-selectin, siglecs, SIGN-receptors and virusprotein 8 (VP8) of human rotaviruses.

As positive control typically human material is used. As negative control, either non-fucosylated proteins, such as BSA or any secretory immunoglobulin preparation from a pooled commercial (i.e. non-selected, non-human) source is used, which source comprises an average of less than 0.01 mol non-core fucose per mol SC in any case. The results of determining the non-core fucose or Lewis epitopes in the SC and/or secretory immunoglobulin preparation are typically compared to a reference with a predetermined amount of non-core fucose per mol SC or SIgA or SIgM, such as 0.01 mol/mol (+/−20%). Thus, the results may be semi-quantitative and refer to "higher than" or "less than" the reference amount. Alternatively the quantitative determination will be possible, e.g. by suitable calibration with a series of references comprising different levels of non-core fucosylation or Lewis epitopes. Standard potency testing refers to the neutralisation activity or binding assays of at least one of *Clostridium difficile* toxin A, *Helicobacter, E. coli* toxins, *Campylobacter, Shigella*, Rotaviruses, Norovirus or competition, binding inhibition or other interactions with lipopolysaccharides, lipoteichoic acid, peptidoglycan, keyhole limpet hemocyanin, DC-SIGN, isolectin A, Aleuria *aurantia* agglutinin, thrombomodulin, langerin, scavenger receptor C-type lectin, E-selectin, siglecs, SIGN-receptors.

Preferably the donor expression system is comprised of non-human, female individuals in the lactating phase to obtain the Secretory Component and optionally the immune complex preparation from the donors' milk or milk fractions. Exemplary source materials are e.g. whey, or dried whey, which contain free Secretory Component, polymeric immunoglobulins and immune complex, respectively, in the enriched form. Preferred source material may be at least 2 fold, 3 fold, 4 fold or 5 fold enriched in immunoglobulins.

The SC or immune complex may then be obtained from such source material in the purified form to prepare the immune complex product according to the invention.

Expression systems alternatively used for producing the immune complex according to the invention may also be recombinant expression systems, among them recombinant host cells of all species and taxa, e.g. recombinant eukaryotic hosts.

Therefore, an amino acid sequence, such as SEQ ID 1 or any functionally active variant sequence thereof, or a nucleotide sequence coding for an SC may be employed to prepare a recombinant host. The sequences preferably encode a SC of mammalian origin, such as human, cow, goat, sheep or humanized versions of non-human SC sequences, or chimerics, always including functional variants. Respective sequence information is provided in the Figures or may be derived from public databases, as appropriate.

Recombinant SC to date has been produced in hosts that are unable to add Lewis-type fucosoylation to the glycans of the Secretory Component. Hosts for purified recombinant SC that were commonly used were CHO cells, BHK cells, mouse J558L cells, insect cells and tobacco plants.

Recombinant SC can be produced by introduction of either the complete gene of pIgR, e.g. human pIgR, into a host cells, subsequent expression of the transmembrane protein pIgR followed by a cleavage and release of the extracellular part, the SC, into the culture supernatant. An alternative expression is the transcription of the nucleotide sequence of the SC, i.e. only the extracellular domains, such as encoding the amino acid sequence of SEQ ID 1. In all cases, the expression of recombinant SC allows for exact selection of production conditions that guarantee a homogeneous C-terminus of the final product.

It also allows choosing the translation termination site according to the needs. Preferably the stop codon on the SC gene to be expressed is located between coding for the last extracellular immunoglobulin-like domain (i.e. domain 5 in human SC) and the transmembrane region. However, the recombinant SC of the invention may be even shorter, e.g. comprising less than 5 full domains, or less than 4 domains, or less than 3 domains, or less than 2 domains, e.g. at least the first domain, as long as it is able to bind and contain the required level of non-core fucose.

The first 18 amino acids in SEQ ID 1 comprise the signal peptide which may be replaced by a different signal peptide depending on the host cells or organisms used and the secretion efficiency required. For production by chemical synthesis or intracellular production of SC the signal peptide is not required (e.g. for production of the non-glycosylated form in E. coli inclusion bodies). The protein may also be modified to contain additional amino acids at the C-terminus of SEQ ID 1.

The protein may be terminated by a stop codon at the required position in the nucleic acid respectively after amino acid G545, preferably at any amino acid site between K566 and E607 (including these sites), more preferred between R603 and E607 (including these sites), or after E607. Most preferably, the SC is terminated after R603. Numbering refers to SEQ ID 1.

Preferably, the SC preparation of the invention is homogeneous, wherein at least 80%, or at least 90%, or at least 95%, up to 100% of the SC molecules have the same C-terminus.

The glycan pattern of the recombinant SC is dependent on the host species, the host organism, the tissue of origin and the physiological state of the genetically engineered cell.

Preferably the host cell is selected from the group consisting of human cells such as PerC.6, Chinese Hamster Ovary cells, Baby Hamster Kidney cells, murine cells, avian cells lines, bacterial, yeast fungal, plant and insect cells. Thereby a recombinant SC may be obtained with the desired non-core fucosylation or Lewis-type N-glycosylation.

The degree of non-core fucosylation in a preparation of the invention may be increased by selection for SC with a high non-core fucosylation (per mol of SC). This can be done at the level of selection of a production host (such screening for a cell line, a microbial clone or an organism), it can also be done on the level of individual donors which are selected to provide secretions containing SC with a high molar non-core fucosylation for subsequent pooling of these samples. The fucosylation can be increased by enzymatic or chemical fucosylation of a preparation of SC or an innate immune complex of the invention.

Normal tissue shows expression of Lewis epitopes at certain sites (e.g. colon, testis) and during certain development stages (fetal antigens). Consequently, certain cell lines from certain sites, e.g. colon carcinoma cell lines express Lewis antigens. Caco-2 cells only express H type 1 blood group antigen and a small amount of LeB during differentiation. Various cell lines (HT-29, AGS, Kato III, HuTu-80, and HEp-2), as well as primary gastric cells, have been explored for Lewis antigen expression. However, many of them are difficult to culture and would not suit as a production host to produce the respective Lewis-type N-glucosylation because of their inherent genetic instability.

Plant N-glycans are in the forms of oligomannosidic (Man>5GlcNAc2), paucimannosidic and complex types. The LeA moiety, localized at the antennae of N-glycans, has been detected not only in Monocotyledons and Dicotyledons, but also in *Physcomitrella patens* (a monoecious moss) and various bryophyte species. LeA is expressed in all plant tissues (flowers, leaves, roots, and seedlings), the responsible α1,4-FucT activity is predominant in young tissues (leaves and roots). However, SIgA expressed in plants so far did not show any Lewis-type glycosylation.

Coexpression of polymeric immunoglobulin (such as dimeric IgA or pentameric IgM) and SC in the same host able to produce N-glycosylated proteins with Lewis epitopes leads to Lewis glycosylated heavy chains which are non-native and therefore not preferred.

It is, thus, specifically preferred that expression systems are used which are able to glycosylate glycoproteins in the desired way, per se, i.e. in the hereditary way, or else by the acquired or transient capability through respective genetic modifications, e.g. through recombination techniques to provide for the respective glycosylation pattern. Exemplary expression systems have an enhanced capability to produce Lewis-fucosylated N-glycoproteins, e.g. through the concomitant expression of fucosyltransferase 2 and 3 and beta 1,3-galactosyltransferase I, II and V.

Hosts that are engineered to produce non-core fucosylated or Lewis-glycosylated oligosacharides and glycoconjugates are, for instance, production cell lines to express various glycosyltransferases such as fucosyltransferases in order to produce oligosaccharides, glycoproteins or glycolipids with blood group related antigens.

Transgenic animals have been described to generate blood group related glycosylations (e.g. WO1995024495A1 or Xu et al. see above). The transgenic organisms of the prior art, however, would provide for the concomitantly Lewis-fucosylated IgA or IgM, which would have excessive non-core fucosylation and a non-native glycosylation pattern. Thus, the immune complex preparation is specifically not derived from milk of such transgenic animals.

Engineered CHO cells have been described to generate Lewis type fucosylation (Löfling et al. 2008, Glycobiology vol. 18 no. 7 pp. 494-501). Also, gain-of-function mutants of CHO cells with the capability to generate Lewis type fucosylated N-glycans have been described (North et al. 2010, J Biol Chem. vol 285 pp. 5759-5775). However, expression of complete SIgA in such host cells would lead to Lewis-fucosylated alpha-immunoglobulin chains with non-native glycosylation. Such cells may therefore be used only to produce human-like SC, after selection of appropriate glycosylation according to the invention. Selection of appropriate recombinant host cell clones is performed as described for the screening of milk samples as described above. It is preferred to engineer, screen and select for more different Lewis-type glycosylations and more genetically stable mutants than described by Löfling et al. and North et al. Recombinant SC derived from such host cells is then being used to prepare immune complexes according to the invention with non-Lewis-fucosylated (i.e. native glycosylation) immunoglobulin from any source.

Specifically it is preferred to cultivate a recombinant host cell line in a bioreactor on a pilot or industrial scale employing conditions to express Lewis-glycosylated SC with yields of at least 1 mg/L culture medium, preferably at least 10 mg/L, preferably at least 100 mg/L, most preferred at least 1 g/L.

The host cell according to the invention is preferably tested for its expression capacity or yield by the following test: ELISA, activity assay, HPLC, or other suitable tests which show the amount and quality of SC or immune complex according to the invention. The host cell is selected not only for expression levels but also for the glycosylation pattern of SC it is able to provide: e.g. at least one of Lewis a, Lewis b, Lewis x and Lewis y or its sialylated forms are to be found on the recombinant SC. Preferably, Lewis x and/or sialyl-Lewis x is present in a sample. More preferable, more than one type of Lewis-antigens on SC is present in a sample.

Preferred fermentation techniques are batch, fed batch or continuous cultivation such as perfusion culture.

Preferably the production cell line is cultivated in a mineral medium with a suitable carbon source, thereby further simplifying the isolation process significantly. An example of a preferred mineral medium is one containing an utilizable carbon source (e.g. glucose, glycerol or methanol), salts containing the macro elements (potassium, magnesium, calcium, ammonium, chloride, sulphate, phosphate) and trace elements (copper, iodide, manganese, molybdate, cobalt, zinc, and iron salts, and boric acid), and optionally vitamins or amino acids, e.g. to complement auxotrophies.

The transformed cells are cultivated under conditions that are suitable to effect expression of the SC which can be purified from the cells or culture medium, depending on the nature of the expression system. As will be understood by the skilled person, cultivation conditions will vary according to factors that include the type of host cell and particular expression vector employed.

If the SC is secreted from the cells, it can be isolated and purified from the culture medium using state of the art techniques. Secretion of the recombinant expression products is generally advantageous for reasons that include facilitating the purification process, since the products are typically recovered from the culture supernatant rather than from the complex mixture of proteins that results when cells are disrupted to release intracellular proteins.

The cultured transformant cells may also be ruptured sonically or mechanically, enzymatically or chemically to obtain a cell extract containing the desired SC, from which the SC is isolated and purified.

Besides genetic engineering techniques it is also possible to provide for the human-like SC by chemical conjugation of Lewis-glycosylated oligosaccharides to SC, enzymatic addition of fucose to generate Lewis antigens on SC in vitro, or enrichment of SC or secretory immunoglobulins from pooled sources by means of Lewis-glycosylation specific ligand binding (e.g. antibodies or alternative scaffolds binding specifically to Lewis antigens, specific lectins such as DC-SIGN, thrombomodulin, isolectin A from *Lotus tetragonolobus* and *Aleuria aurantia* agglutinin, certain siglecs, selectins).

Isolation and purification methods used for obtaining an SC or immune complex according to the invention may utilize differences in solubility, such as salting out and solvent precipitation, differences in molecular weight, such as ultrafiltration and gel electrophoresis, differences in electric charge, such as ion-exchange chromatography, or may utilize specific affinities, such as affinity chromatography, or may utilize differences in hydrophobicity, such as reverse phase high performance liquid chromatography, or utilize differences in isoelectric point, such as isoelectric focusing. Specific purification steps are preferably employed to separate any SC polypeptide alone or in complex with immunoglobulins are ultrafiltration techniques with molecular cutoffs between 100 kDa and 500 kDa and precipitation techniques such as precipitation with salts such as ammonium sulfate or organic solvents.

The isolated and purified SC can be identified and analysed by conventional methods such as Western blotting or assay of its activity, e.g. by its ability to bind to dimeric IgA or the J-chain or by detection with specific antisera against the SC.

The structure of the purified compound can be defined by amino acid analysis, amino-terminal analysis, primary structure analysis, glycoanalysis and the like. It is preferred that the SC compound is obtainable in large amounts and in specific cases with a high purity, thus meeting the necessary requirements for being used as part of an immune complex according to the invention to be used as an active ingredient in pharmaceutical compositions.

The immune complex preparation according to the invention preferably is used as a food product, e.g. to provide a specific diet to subjects in need thereof, which are e.g. at risk of or suffering from a disease condition caused by a pathogen.

A further preferred use is the prevention of a disease or disorder caused by a pathogen, including microbial substances or organism, antigens or disease causing agents, such as toxins. For example, hospitalised patients may need to supplement their immune system to reduce the risk of a hospital-acquired infection. Neonatal humans or animals receiving the food supplement according to the invention may have a higher chance of survival in case that they cannot obtain sufficient colostrum from mothers or respective wet nurses. Furthermore, the risk of enteropathogenic disease in animals and humans may be reduced by such food product.

The preparation according to the invention may be used to treat infectious diseases of the mouth, throat, nose and ears, the eyes and esophagus, the gastric and colon tract.

Suitably the preparation according to the invention may be provided in a formulation, which optionally provides for further nutrients such as proteins, carbohydrates, lipids, and other physiologically active substances.

Exemplary preparations produced according to the invention include dairy milk and whey powders which are a by-product of either dairy production. Whey based products according to the invention additionally comprise, for instance, serum albumins, lactalbumin, lactoglobulin, lactoferrin, lactoperoxidase, oligosaccharides, peptides, lactose and minerals. In some cases it is preferred to obtain a product from milk or whey from hyperimmunised adults so that the preparation according to the invention contains some increased level of immunoglobulins reactive with a specific group of disease organisms, pathogens or disease related antigens.

The present invention specifically encompasses the stabilisation of the Lewis-glycosylated functional human-like SC by IgA or IgM molecules having a native glycosylation pattern, i.e. without Lewis-epitopes on N-glycans.

The stabilised immune complex may have an increased thermostability and/or gastrointestinal stability, as measured by pH stability and/or protease stability of the protein, resulting in an increased recovery or prolonged in vivo half-life. The stabilising effect is particularly important for the mucosal recovery. Upon administration of the preparation according to the invention, the immunoactivity of the immune complex may be determined in the mucosa by immunological techniques such as ELISA. An increased level of immunoglobulins in the mucosa indicates an increased recovery.

The preparation according to the invention may further comprise free, unbound SC as well as SC complexed with immunoglobulin, which could even enhance its functional properties.

A preferred embodiment of the invention is an SC molecule according to the invention attached to a natural antibody in order to provide a proteolytically stable, multivalent and polyspecific molecule that is able to neutralize various pathogen antigens.

It is further preferred that the immune complex preparation according to the invention contains from 5 to 100% w/w secretory immunoglobulins (i.e. polyimmunglobulin in complex with the SC). More particularly, the preparation may contain from 20 to 70% w/w secretory immunoglobulins.

The preparation according to the invention may also preferably contain other components such as carbohydrates. The carbohydrates are preferably sourced from whey protein concentrate and are present in the preparation in a concentration between 0 and 95% w/w. More preferably, carbohydrates are present between 30 and 90% w/w. The carbohydrates provide a readily available energy source.

Dextrose is also preferably used as a carbohydrate additive, which may be included in the preparation to assist in preventing agglomeration of the powder and to provide a further form of carbohydrate.

Further preferred additives are whey proteins, which may further stabilise the immunoglobulin preparation, amino acids for nutritional purposes, oligosaccharides, and substances that enhance the physiological value of the preparation.

It may also be preferred to include antimicrobial substances in the formulation according to the invention, such as antibiotics, antivirals, antifungals, antiparasitics, or microbicidal substances, including organic acids, plant essential oils, cations, colloidal silver or quaternary ammonium salts.

It is particularly preferred that the formulation according to the invention is provided as a liquid, emulsion, suspension, slurry or in a dried form such as powder or granulate. Specifically preferred formulations are manufactured as a powder or granulate which can be formulated into a liquid instantly before use.

Further preferred administration forms are tablets, lozenges, capsules, pastes, granules, creams, etc. which may be produced by standard methods. Tablets preferably contain auxiliary additives such as fillers, binders, disintegrants, lubricants, flavors or the like). Granules may be produced using isomaltose. A daily dose of 1 mg to 10 g immune complex may be provided in a formulation according to the invention for use in humans.

It is furthermore preferred to provide for a preparation formulated to act at the site of the mucosa, e.g. at mucosal sites (nose, mouth, eyes, esophagus, throat, lung, ears, gastric tract, intestine and colon), e.g. locally without systemic action. The preparation according to the invention typically is provided for oral or mucosal use, including oral, nasal, bronchial, vaginal, rectal use, e.g. to inhibit adherence to pharyngeal, intestinal, genitourinary tract and gingival epithelia. The preparation may be provided for certain medical indications in a form suitable for topical application, such as in a cream, spray or droplets.

The immune complex preparation according to the invention may be specifically used for treating and/or preventing infections and/or inflammation and/or allergic symptoms and/or symptoms of autoimmune disease and/or immunoglobulin deficiency of the mucosal surfaces, e.g. the gastrointestinal tract, urogenital tract, respiratory tract, nasal cavity, the eyes or oral cavity, especially after surgery or during hospitalization.

The foregoing description will be more fully understood with reference to the following examples. Such examples are, however, merely representative of methods of practicing one or more embodiments of the present invention and should not be read as limiting the scope of invention.

EXAMPLES

Example 1

Screening of Milk and Whey Samples for Lewis-Glycosylated SIgA

Sample Preparation (Milk, Whey)

10 ml Milk from goat, sheep and cow is sampled freshly and centrifuged at 40,000×g for 30 min at 4° C. The fat layer is removed with a spatula; the remaining liquid is transferred into a new centrifuge tube and centrifuged again at 40,000×g for 30 min.

The liquid layer (milk serum) is aliquoted and stored at −20° C. or used for screening directly.

Positive Control Sample

As a positive sample, human milk is prepared as described above.

Negative Control Samples

As negative control for cow milk (Vollmilch, 3.5% fat, Niederösterreichische Molkerei, Austria) is used.

Negative control for goat milk "Ja Natürlich" Ziegenmilch, Sennerei Zillertal, Austria, is used.

Screening ELISA

Screening is performed in a standard ELISA format: For screening of goat milk samples ELISA plates (Nunc MaxiSorp Immuno Plate) are coated with polyclonal rabbit anti-goat IgA (AbD Serotec no. AAI44) at a concentration of 1 microgram per ml coating buffer (3.03 g $Na_2CO_3$, 6.0 g $NaHCO_3$ in 1000 ml distilled water, pH 9.6) at 100 microliters per well. For screening of bovine milk samples or sheep milk samples anti-bovine IgA (Genataur no. RA-10A, Belgium) or anti-sheep IgA (LSBio no. LS-C57110, USA) respectively is coated to the plates. For the positive control samples anti-human-IgA antibodies are coated to the respective wells (Bethyl Laboratories no. A80-103A, USA). The plates are closed with a lid and incubated overnight at 4° C.

Before the next step the coating solution is removed and the plates are washed three times by filling the wells with 200 μl TPBS (1.16 g $Na_2HPO_4$, 0.1 g KCl, 0.1 g $K_3PO_4$, 4.0 g NaCl in 500 ml distilled water, 0.05% (v/v) Tween20, pH 7.4). The solutions or washes are removed by flicking the plate over a sink. The remaining drops are removed by patting the plate on a paper towel. Alternatively, washing can be performed with an ELISA washer.

Plates are filled with Superblock blocking buffer (Thermo no 37515) 150 microliters/well and incubated at room temperature for 2 hours.

Again, the plates are washed as described above.

The milk serum samples are diluted in sample TPBS (1:2 and 1:10). 16 negative controls for each dilution (1:2 and 1:10) are added to each plate. 4 positive control samples for each dilution are added to the plate. 100 microliters of the respective dilutions are added into wells of the washed plate and incubated at room temperature for 2 hours.

After washing, 100 microliters of a mixture of anti-Lewis x-antibody (LSBio no. LS-C75829), anti-sialyl-Lewis a-antibody (LSBio no. LS-C33820), anti-Lewis a-antibody (LS- Bio no. LS-050512), anti-sialyl-Lewis b-antibody (GeneTex no. GTX72378, USA 1:300), anti-Lewis b antibody (LSBio no. LS-C46049) and anti-Lewis y-antibody (LSBio no. LS-C71674, USA, 1:50) dilutions in TPBS are added to the respective sample wells and to the negative and positive control sample wells.

The plate is again incubated for 2 hours at room temperature and subsequently washed.

Then, 100 microliters per well of a chicken anti-mouse-IgG-HRP (Thermo, no. SA1-72029, 1:500 in TPBS) is added and incubated for 2 hours at room temperature. Subsequently, the plates are washed three times with TPBS.

A further washing step is then performed with substrate buffer (TMB Substrate kit; Vector Laboratories no SK-4400, USA). Thereafter, chromogenic substrate is added (Vector Laboratories SK-4400). After short incubation (measurement of positive control at OD 650>1.0, negative control OD<0.2) 50 microliters of 1 N sulfuric acid are added and the plate is read in the microplate reader at OD450, compensated by OD600 as in standard ELSA techniques utilizing TMB as substrate.

Evaluation:

The OD values of the 16 Negative Controls for each dilution are used for calculation of mean and standard deviation of negative signals.

A milk serum sample is regarded as positive in this screening assay if it shows with at least one dilution a higher absorbancy than the mean absorbancy plus 2 times the standard deviation of the negative controls at the same dilution.

Positive milk serum samples are used for further analysis.

The example demonstrates that it is possible to select and screen animal species, individuals and races in order to produce milk with a substantially higher content of Lewis-glycosylated SIgA than currently commercially available milk.

Example 2

Expression of Lewis-Fucosylated Recombinant Human Secretory Component in Mammalian Cells This example describes the establishment of mammalian cells expressing Secretory Component modified by various glycosyltransferases and subsequent screening for clones producing Lewis-fucosylated Secretory Component.

The Secretory Component Protein sequence (the extracellular part of pIgR) is shown in FIG. 1.

The protein Sequence is reverse translated into DNA (optimized for mammalian cell expression) and synthesized de novo (Geneart, Germany). For cloning purposes the DNA is provided with HindIII and XbaI recognition and cleavage sites (italic and underlined). See FIG. 2.

The gene is inserted at the HindIII and XbaI sites in the vector pCDNA3.1+(invitrogen, USA).

To generate stable transfectants, plasmids are linearized with PvuI and subsequently transfected into CHO-K1 cells (CHO DUK-; ATCC CRL 9096) using Lipofectamine 2000 according to the manufacturer (Invitrogen). Twenty-four hours following transfection, cells in each T-flask are split into five 100-mm petri dishes and incubated in the selection medium. The concentration of G418 is 200-400 microgram/mL. The selection medium is changed every third day. Drug resistant clones can be seen after approximately 2 weeks, identified under the microscope, and handpicked using a pipetman. Selected colonies are cultured in 96-well plates in the presence of G418 for 2 weeks. Growing cells are split into duplicate wells and supernatants are tested for expression of Secretory Component in a standard ELISA. In short, goat anti-Secretory Component antibody (Acris Antibodies AP21476FC-N) is coated to the plates, after incubation and washing, supernatants of the cells are added (1:2 and 1:10 diluted). After incubation and washing, mouse anti-human-SC is added (Sigma 16635) and subsequently detected with anti-mouse-IgG-HRP. Selected positive clones are used for purification of Secretory Component and for further transfection with glycosyltransferases.

Transfection with various glycosyltransferases: Stable positive clones expressing Secretory Component are selected and transfected with 2 plasmids, one coding for fucosyltransferase 2 and fucosyltransferase 3, the other for a beta 1,3-galactosyltransferase.

The protein sequence of alpha 1,2-fucosyltransferase (FUT2) is shown in FIG. 3.

Back translated sequence of FUT2 including NheI and EcoRI recognition and cleavage sites at the 5' and 3' end. The gene is synthesized de novo (Geneart, Germany), see FIG. 4. The gene is cloned with NheI and EcoRI into the multiple cloning site A of vector pIRES (Clontech, no 631605), resulting in pIRESF2.

The protein sequence of fucosyltransferase 3 is shown in FIG. 5.

The sequence is back translated into optimized codon usage sequence and provided with XbaI and NotI recognition sites at the very end, see FIG. 6.

The DNA is synthesized de novo and cloned into XbaI and NotI sites of the multiple cloning site B of the pIRESF2 vector containing the FUT 2 gene as described above, resulting in plasmid pIRESF23.

For transfection the pIRESF23 vector containing the FUT2 and FUT3 genes is linearized with BpmI.

A number of expression plasmids containing various beta 1,3-galactosyltransferases are prepared. Therefore, the protein sequences for the galactosyltransferases are back translated into DNA sequences (optimized for expression in mammalian cells) and provided with unique restriction sites at the very ends (NheI and NotI). The DNA is synthesized and cloned into the NheI and NotI site of pEF1alpha1 RES (Clontech631970). The respective plasmid is linearized with AatII before cotransfection with pIRESF23 containing FUT2 and FUT3 into CHO cells expressing recombinant human Secretory Component.

The protein sequence of beta 1,3-galactosyltransferase 1 is shown in FIG. 7.

The gene for beta 1,3-galactosyltransferase 1 is shown in FIG. 8

The protein sequence of beta 1,3-galactosyltransferase V is shown in FIG. 9, the respective gene ready for cloning is shown in FIG. 10.

The protein sequence of beta 1,3-galactosyltransferase II is shown in FIG. 11, the respective gene with cloning sites is shown in FIG. 12.

Transfection and Selection Procedure

CHO cell clones expressing human Secretory Component are being transfected in a standard transfection procedure with mixtures of plasmids: Linearized pIRESF23 is combined with linearized plasmids encoding for beta-1,3-galactosyltransferase I, beta-1,3-galactosyltransferase II and beta-1,3-galactosyltransferase V, respectively. The transfection is followed by a standard selection procedure to yield stable clones (G418 concentration may be increased to 1000 micrograms per ml selection medium).

Screening for Clones Expressing Lewis-Glycosylated Secretory Component:

Supernatants of CHO clones are tested in ELISA specific for Secretory Component and Lewis glycosylation:

Screening is performed in a standard ELISA format: For screening cell culture supernatants ELISA plates (Nunc Maxi-Sorp Immuno Plate) are coated with anti-human-secretory component antibodies (Ray Biotech no. DS-PB-03010, USA) at a concentration of 1 microgram per ml coating buffer (3.03 g $Na_2CO_3$, 6.0 g $NaHCO_3$ in 1000 ml distilled water, pH 9.6) at 100 microliters per well.

The plates are closed with a lid and incubated overnight at 4° C.

Before the next step the coating solution is removed and the plates are washed three times by filling the wells with 200 μl TPBS (1.16 g $Na_2HPO_4$, 0.1 g KCl, 0.1 g $K_3PO_4$, 4.0 g NaCl in 500 ml distilled water, 0.05% (v/v) Tween20, pH 7.4). The solutions or washes are removed by flicking the plate over a sink. The remaining drops are removed by patting the plate on a paper towel. Alternatively, washing can be performed with an ELISA washer.

Plates are filled with Superblock blocking buffer (Thermo no 37515) 150 microliters/well and incubated at room temperature for 2 hours.

Again, the plates are washed as described above.

The cell culture supernatants are diluted in sample TPBS (1:2 and 1:10). 16 negative controls for each dilution (1:2 and 1:10) are added to each plate. 4 positive control samples for each dilution are added to the plate. 100 microliters of the respective dilutions are added into wells of the washed plate and incubated at room temperature for 2 hours.

After washing, 100 microliters of a mixture of anti-Lewis x-antibody (LSBio no. LS-C75829), anti-sialyl-Lewis a-antibody (LSBio no. LS-C33820), anti-Lewis a-antibody (LSBio no. LS-050512), anti-sialyl-Lewis b-antibody (GeneTex no. GTX72378, USA 1:300), anti-Lewis b antibody (LSBio no. LS-C46049) and anti-Lewis y-antibody (LSBio no. LS-C71674, USA, 1:50) dilutions in TPBS are added to the respective sample wells and to the negative and positive control sample wells.

The plate is again incubated for 2 hours at room temperature and subsequently washed.

Then, 100 microliters per well of a chicken anti-mouse-IgG-HRP (Thermo, no. SA1-72029, 1:500 in TPBS) is added and incubated for 2 hours at room temperature. Subsequently, the plates are washed three times with TPBS.

A further washing step is then performed with substrate buffer (TMB Substrate kit; Vector Laboratories no SK-4400, USA). Thereafter, chromogenic substrate is added (Vector Laboratories SK-4400). After short incubation (measurement of positive control at OD 650>1.0, negative control OD<0.2) 50 microliters of 1 N sulfuric acid are added and the plate is read in the microplate reader at OD450, compensated by OD600 as in standard ELSA techniques utilizing TMB as substrate.

Evaluation:

16 Negative controls for each dilution are used for calculation of mean and standard deviation of negative signals.

A sample is regarded as positive in this screening assay if it shows with at least one dilution a higher absorbancy than the mean absorbancy plus 2 times the standard deviation of the negative controls at the same dilution.

Positive samples are used for protein purification and further analysis.

This example demonstrates that it is possible to generate Secretory Component which is not derived from human milk with a high molar proportion of Lewis-epitopes.

Example 3

Quantitative Evaluation of the Presence of Lewis-Epitopes on Secretory Component Purification of recombinant Secretory Component from supernatant of animal cells and secretory IgA is performed by affinity chromatography with rabbit-anti-human Secretory Component coupled to Sepharose according to standard protocols.

Sample Preparation for Glycan-Analysis:

The purified secretory IgA is separated into SC, J chain, H chain, and light chain by reducing SDS-PAGE (80×80×1 mm, 10% BisTris NuPAGE gel, MES SDS running buffer (Invitrogen)). The protein bands are visualized by Coomassie staining. Molecular mass standards are used.

The ~80 kDa Coomassie stained bands are excised and in-gel digested with trypsin and alkylated (In-Gel Tryptic Digestion Kit, Thermo Scientific product no. 89871).

The purified, reduced and alkylated peptides of the Secretory Component are defucosylated at the innermost GlcNAc residue by overnight treatment in 10 mM NH4Ac (pH 5.0) at 37° C. with alpha-1-6-fucosidase from bovine kidney (ProZyme, no GKX-5006, USA). The completeness of the core-fucose removal can be verified, if necessary, by analysis of the released N-glycans by chromatography on porous graphitic carbon with MS detection.

Analysis of peptides and glycopeptides is performed on a capillary LC-ESI-MS system consisting of an Aquasil C-18 precolumn (30 mm×0.32 mm, 5 micrometer, Thermo Scientific), a BioBasic C18 analytical column (150 mm×0.18 mm, 5 micrometer, Thermo Scientific), a Waters CapLC, a Rheodyne 10-port valve and a Waters Q-TOF Ultima with standard ESI-source.

Solvent A consists of 65 mM ammonium formate of pH 3.0 and solvent B is

80% acetonitrile (ACN) in solvent A. The precolumn is equilibrated and loaded in the absence of ACN. Thereafter, a gradient from 6.3 to 62.5% solvent B is developed over 45 min. Positive ions in the range from m/z 150 to 1800 are measured. Capillary voltage is 3.2 kV and cone voltage 35 V, source temperature is 100° C., desolvation temperature 120° C.

Data are evaluated using MassLynx 4.0 software including MaxEnt3 deconvolution/deisotoping feature (Waters).

The glycosylated peptides are identified by deglycosylation with PNGnase F (Roche) and further separation in reverse phase HPLC followed by mass spectroscopy. The deglycosylated peptide contains a glutamic acid instead of a glutamine residue, which results in a mass difference of 1 Da.

Different glycan structures on the same peptide backbone divide the possible glycopeptide signal into several molecular species of different mass. The presence of glycopeptides can also be indicated in a total mass spectrum as a ladder of masses with steps based on specific monosaccharide differences (e.g., m/z 146 [Fucose], 162 [Hexose], 203 [N-acetylhexosamine], 291 [N-acetyl neuraminic acid]) between the different glycoforms.

Once the glycopeptide peaks are identified, the peak "volume", i.e. the area under the peaks corresponding to a particular glycopeptide is measured. The peak volume can be translated directly into molar proportions of glycoforms as the ionization and hence detection of the glycopeptides is dominated by the peptide portion.

The mass spectra are acquired over the elution time of an identified or potential glycopeptide and are summed, smoothed and centroided before the m/z vs intensity spectrum is submitted to the software for analysis.

To increase signal-to-noise ratio for low intensity glycoforms, it is recommended to sum the MS-spectra only over the respective elution peak rather than over a wider chromatographic time frame.

From the list of glycoforms occurring on a particular glycosylation site, the molar fraction of fucosylated glycans is calculated. The results for the different sites are added to arrive at the molar proportion fucosylated glycans occurring in the Secretory Component.

Exemplary results and calculations are shown with a sample of human Secretory Component:

Relative amount of each peptide glycoform:
Peptide 82-109
2.6% $Hex_9HexNAc_7Fuc_3NeuAc_0$
5.2% $Hex_{10}HexNAc_8Fuc_0NeuAc_0$
15.6% $Hex_{10}HexNAc_8Fuc_2NeuAc_0$
4.2% $Hex_{10}HexNAc_7Fuc_4NeuAc_0$
21.8% $Hex_{10}HexNAc_8Fuc_3NeuAc_0$
21.3% $Hex_{10}HexNAc_8Fuc_4NeuAc_0$
15.9% $Hex_{10}HexNAc_8Fuc_3NeuAc_1$
8.1% $Hex_{10}HexNAc_8Fuc_4NeuAc_1$
3.3% $Hex_{10}HexNAc_8Fuc_5NeuAc_1$
2.0% $Hex_{10}HexNAc_8Fuc_4NeuAc_2$ At glycosylation sites Asn83 and Asn90, 95% of glycoforms bear a non-core fucose-residues peptide 168-190
3.3% $Hex_5HexNAc_4Fuc_0NeuAc_0$
55.1% $Hex_5HexNAc_4Fuc_2NeuAc_0$
35.4% $Hex_5HexNAc_4Fuc_3NeuAc_0$
6.1% $Hex_5HexNAc_4Fuc_2NeuAc_1$ At glycosylation sites Asn186 97% of glycoforms bear a non-core fucose-residues peptide 413-434
24.2% $Hex_5HexNAc_4Fuc_2NeuAc_0$
37.7% $Hex_5HexNAc_4Fuc_3NeuAc_0$
38.2% $Hex_5HexNAc_4Fuc_2NeuAc_1$ At glycosylation sites Asn421 100% of glycoforms bear a non-core fucose-residues peptide 457-479
11.0% $Hex_5HexNAc_4Fuc_0NeuAc_0$
46.9% $Hex_5HexNAc_4Fuc_2NeuAc_0$
42.1% $Hex_5HexNAc_4Fuc_3NeuAc_0$ At glycosylation site Asn469, 89% of glycoforms bear a non-core fucose-residues.

peptide 498-515
6.1% $Hex_4HexNAc_3Fuc_0NeuAc_0$
7.7% $Hex_5HexNAc_3Fuc_0NeuAc_0$
3.6% $Hex_5HexNAc_4Fuc_0NeuAc_0$
18.9% $Hex_5HexNAc_3Fuc_0NeuAc_0$
23.2% $Hex_5HexNAc_4Fuc_1NeuAc_0$
7.8% $Hex_5HexNAc_3Fuc_2NeuAc_0$
25.8% $Hex_5HexNAc_4Fuc_2NeuAc_0$
5.1% $Hex_5HexNAc_4Fuc_3NeuAc_0$
1.8% $Hex_5HexNAc_4Fuc_2NeuAc_1$ At glycosylation site Asn499, 64% of glycoforms bear a non-core fucose-residues.

Non-core (Lewis) fucosylation of the sample=0.95 mol+ 0.97 mol+1 mol+0.89 mol+0.64 mol=4.45 mol/mol Secretory Component Example 4

Expression of Dimeric IciA in Mammalian Cells and Reconstitution of a SIgA Molecule with Recombinant Lewis-Glycosylated Secretory Component Murine J558L cells are used as host for expression of a germline antibody binding to the hapten nitrophenyl. For this purpose the chimeric heavy chain (murine VH/human IgA2 constant region) is cloned in mammalian expression vector pCDNA3.1, the plasmid is transfected into J558L cells and clones, stably expressing dIgA are selected and screened. Parallel to the IgA2 heavy chain, a construct with IgA1 heavy chain is prepared and used.

Dimeric IgA is purified and reconstituted with recombinant Secretory Component from CHO cells (see example 2).

The Protein Sequence of chimeric anti-nitrophenyl IgA heavy chain (small letters=leader peptide, underlined=murine VH) is shown in FIG. 13, the DNA sequence of the heavy chain construct, including HindIII and XbaI restriction sites is shown in FIG. 14.

The gene is fully synthesized with HindIII and XbaI sites (Geneart, Germany) and cloned into the respective sites in pCDNA3.1+(Invitrogen, USA). Before transfection, the recombinant plasmid is linearized with PvuI.

Murine J558L cells (Health Protection Agency Culture Collections no. 88032902), which show constitutive synthesis of the J chain and a lambda light chain specific for NIP, are grown in RPMI medium with penicillin (100 IU/ml) and streptomycin (100 microg/ml; Bio Whittaker, Walkersville, Md.) and 10% fetal calf serum (Invitrogen) at 37° C. in an atmosphere with 5% CO2. Stable transfection of J558L is achieved by electroporation, and clones are selected in medium containing 500 microg/ml G418 (Sigma). The cells are incubated for 2-3 weeks before the supernatant fluids are harvested and screened for immunoglobulin production by enzyme-linked immunosorbent assay (ELISA).

For ELISA, microplates are coated with anti-j chain antibody (goat anti-J chain, Santa Cruz, sc-34654). After washing, cell culture supernatants (diluted 1:2 and 1:10) are added. Subsequently to incubation and washing, anti-human-IgA alpha chain-HRP conjugate is used for detection of cell lines expressing IgA.

Purification of recombinant dIgA from culture supernatant of selected clones is performed by affinity chromatography utilizing an anti-human-IgA coupled sepharose (Sigma A2691) according to the manufacturer and standard affinity chromatography procedures.

Reconstitution of SIgA from IgA and Recombinant Secretory Component

Reconstitution of dIgA-Secretory Component Complexes was performed in vitro by mixing equimolarily purified dIgA and purified Secretory Component (fucosylated and non-fucosylated respectively) overnight in PBS buffer at a concentration of 10 micrograms per 100 microliters.

Reconstituted complexes are loaded onto a non-reducing and a reducing 6% SDS-polyacrylamide gel respectively, blotted to polyvinylidine difluoride membrane, and detected with antiserum against Secretory Component.

Covalent reconstitution takes place as indicated by the shift of the Secretory Component to the position of dIgA and pIgA molecules. Under reducing conditions, only free Secretory Component can be detected to a similar extent in every lane, indicating that Secretory Component and IgA are linked by disulfide bridges.

The complexes are further purified by HPLC. Such purified SIgA (Lewis glycosylated and non-fucosylated) in PBS is quantified and used in antigen binding and stability experiments.

Example 5

Stability Testing of Recombinant Lewis-Glycosylated SIgA

The various assays are performed to show the biophysical, biochemical and biological stability of the molecules of the invention.

For biophysical stability, the samples are analyzed by Differential Scanning calorimetry:

The immune complexes and antibodies are dialyzed against a 20 mM sodium citrate, 150 mM NaCl buffer at pH 6.0. Antibody concentrations are measured by UV absorbance. The antibodies are diluted to 1 mg/mL using dialysate. Scans are performed using an automated capillary DSC (MicroCal, LLC). Two scans with dialysates are performed for baseline subtraction. Scans run from 20-95° C. at 1° C./min using the medium feedback mode. Scans are analyzed using Origin 7.0. Nonzero baselines are corrected using a third order polynomial. The unfolding transitions of each immune complex are fit using the non-two-state unfolding model within the software.

Biochemical Stability (Gel electrophoresis after acid incubation): All samples with immune complexes and controls are buffer exchanged into the formulations of various pH values (4.0, 5.0, 6.0 and 7.0) by using a desalting column (NAP25 column, GE Healthcare), and their concentrations are adjusted to 5 mg/ml. The formulated antibody solutions are sterilized by 0.22 micrometer filter, and 1 ml of each solution is filled into sterilized USP type I, 5-ml capacity glass vial and sealed with autoclaved rubber stopper. These prepared samples are stored in the temperature-controlled incubator at 40° C. for 1 day before the size exclusion chromatography (SEC) analysis.

Size Exclusion Chromatography: The amount of aggregates (high molecular weight products) and degradation species (low molecular weight products) are analyzed by SEC using a G3000SWXL column (7.8 mm i.d. 30 cm; Tosoh Corp. Japan). The mobile phase consists of 50 mM sodium phosphate (pH 7.0) and 500 mM sodium chloride. The experimental conditions are as follows: injected protein, 20 mg; flow rate, 0.5 ml/min; detection wavelength, 215 and 280 nm; and analysis time, 30 min. The amounts of high molecular weight products and low molecular weight products present in the samples that have been stored at 40° C. for 1 day in glass vials are determined and expressed as a relative increment compared to those of respective freshly prepared samples.

Protease Stability

All digestions are performed at 37° C. for 8 hr with protein concentrations of the samples of 5 mg/ml and total volumes of 1 ml. Trypsin and pepsin (Sigma, USA) are used as proteolytic enzymes. Trypsin digestions are carried out in 0.05 M Tris buffer, pH 8.0. Digestions with pepsin are performed in 0.05 sodium acetate buffer, pH 4.0. All proteins are dialyzed for 24 hr against these buffers before digestion. Enzyme to protein ratios are 1:25 or 1:50 for both enzymes. Trypsin digestions are stopped by adding an equimolar amount of soybean trypsin inhibitor (Sigma) to the reaction mixture, while pepsin digestions are terminated by raising the pH of the solution to about 8 by the addition of 100 microliter 2.5 M Tris. After the digestions, all reaction mixtures are frozen before further analyses.

Evaluation of digestion: Each digest is thawed and applied to a column (1.5×90 cm) of Superdex 200 (GE Healthcare), calibrated with IgA dimer, IgG, and bovine serum albumin. The absorbance of the eluate is recorded at 280 nm.

The area under the peak for emerging peaks and at the position corresponding to intact molecules is expressed as percent of the total area.

Example 6

Specificity Testing of Differently Glycosylated SIgA

Various Lewis-positive and Lewis-negative SIgA (reconstituted SIgA as described in previous example) can be tested for binding to a spectrum of pathogen structures.

Titres of purified immune complexes of the invention can be tested in an ELISA procedure for binding *Escherichia coli*-derived lipopolysaccharide (LPS), *Staphylococcus aureus*-derived lipoteichoic acid (L2515, Sigma, USA), peptidoglycan from *Staphylococcus aureus* (PGN) and keyhole limpet hemocyanin (KLH, MP Biomedicals). The assay is described in J. Dairy Sci. vol. 93 pp. 5467-5473:

Plates are coated with 100 μL/well of 1 μg of KLH, 4 μg of LPS, 5 μg of LTA, or 2 μg of PGN per mL of carbonate buffer (10.6 g/L $Na_2CO_3$, pH 9.6). After washing, plates are blocked with 100 μL/well of 2.5% rabbit serum in PBS with 0.05% Tween20 for at least 30 min at room temperature (21° C.). Serial dilutions of samples (1:4) in PBS, 0.05% Tween20, and 2.5% rabbit serum are added. Plates are incubated for 1 h at room temperature (21° C.).

Binding of immune complexes and antibodies to LPS, LTA, PGN, or KLH is detected using 100 μL/well of 1:15,000 diluted rabbit anti-bovine-(anti-human, anti-goat)-IgA coupled to peroxidase. After washing, 100 μL/well of tetramethylbenzidine (71.7 μg/mL) and 0.05% $H_2O_2$ are added to the wells and incubated for 10 min at room temperature (21° C.). The reaction is stopped with 50 μL/well of 2.5 N of $H_2SO_4$. Extinctions are measured with a microplate spectrophotometer at a wavelength of 450 nm. Levels are calculated as titers, and titers were expressed as log 2 values of the dilutions that gives an extinction closest to 50% of Emax, where Emax represents the highest mean extinction of a standard positive sample present in duplicate on every microtiter plate.

Binding to *Clostridium difficile* toxin A and *E. coli* intimin has been described e.g in THE JOURNAL OF BIOLOGICAL CHEMISTRY VOL. 281, NO. 20, pp. 14280-14287, the binding to norovirus-VLPs is described e.g. in Journal of Virology, Vol. 79, pp. 6714-6722:

Microwell Binding Assay—The wells of Nunc MaxiSorp ELISA plates are coated with 200 ng of immune complex, antibodies, or Secretory Component in 100 microliter of 50 mM sodium bicarbonate (pH 9.6) for 1 h at room temperature. Wells are blocked with 200 microliter of PBS-T containing 5% (w/v) nonfat dry milk. Toxin A (500 ng/ml) or GST-intimin (200 ng/ml) or norovirus VLPs (1 microgram/ml) in 100 microliter of PBS are incubated for 2 h at room temperature. Following three washes with PBS-T, binding is detected using specific antibodies (SC-toxin A interaction is detected with murine anti-toxin A IgG, norovirus VLPs are detected with mouse anti-norovirus and GST-intimin is detected using murine mAb against GST), followed by goat anti-mouse IgG, horseradish peroxidase-conjugated and 1,2-

Example 7

Antibacterial Activity of Goat SIgA Obtained According to Example 11—Binding of Natural Antibodies to Bacterial Antigens Reactivity of purified immune complexes of the invention with *Escherichia coli* derived lipopolysaccharide (LPS) and *Clostridium difficile* Toxin A are tested in ELISA.

Plates are coated with 100 µL/well of 4 µg of LPS (Lipopolysaccharide from *E. coli* 0157H7, List Biological Laboratories, Campbell, Calif., USA, cat. no. 206) or 1 µg of *Clostridium difficile* Toxin A (List Biological Laboratories, Campbell, Calif., USA, cat. no. 152) per mL of carbonate buffer (10.6 g/L $Na_2CO_3$, pH 9.6). After washing, plates are blocked with 100 µL/well of 2.5% rabbit serum in PBS with 0.05% Tween20 for at least 30 min at room temperature (21° C.). Serial dilutions of samples (1:4) in PBS, 0.05% Tween20, and 2.5% rabbit serum are added. Plates are incubated for 1 h at room temperature (21° C.).

Binding of immune complexes and antibodies to LPS or *C. diff.* Toxin A is detected using 100 µL/well of 1:15,000 diluted rabbit anti-goat-IgA (and anti-human-IgA respectively) coupled to alkaline phosphatase. After washing, 100 µL/well of paranitrophenylphosphate are added to the wells and incubated for 30 min at room temperature (21° C.).

Optical density are measured with a microplate spectrophotometer at a wavelength of 405 nm.

The preparations tested were human SIgA (Sigma 12636) and several goat SIgA prepared from different samples according to Example 11 below, all having at least 0.01 mol non-core fucose per mol SIgA. As a result all goat SIgA were binding to *C. diff.* Toxin A and LPS (*E. coli* 0157H7) about five times higher than the human reference.

Example 8

Rapid Screening Test to Determine Non-Core Fucosylated Immune Complexes in Milk or Whey Samples by a Lateral Flow Assay A simple and rapid assay can be used to decide on the inclusion of a certain milk sample into the pool in order to increase the level of N-glycosylation with Lewis-epitopes on the Secretory Component in the pool.

Such an on-site assay can be a rapid immunoassay which is optimized to show positivity at a certain threshold with milk or whey samples.

Figure 15:
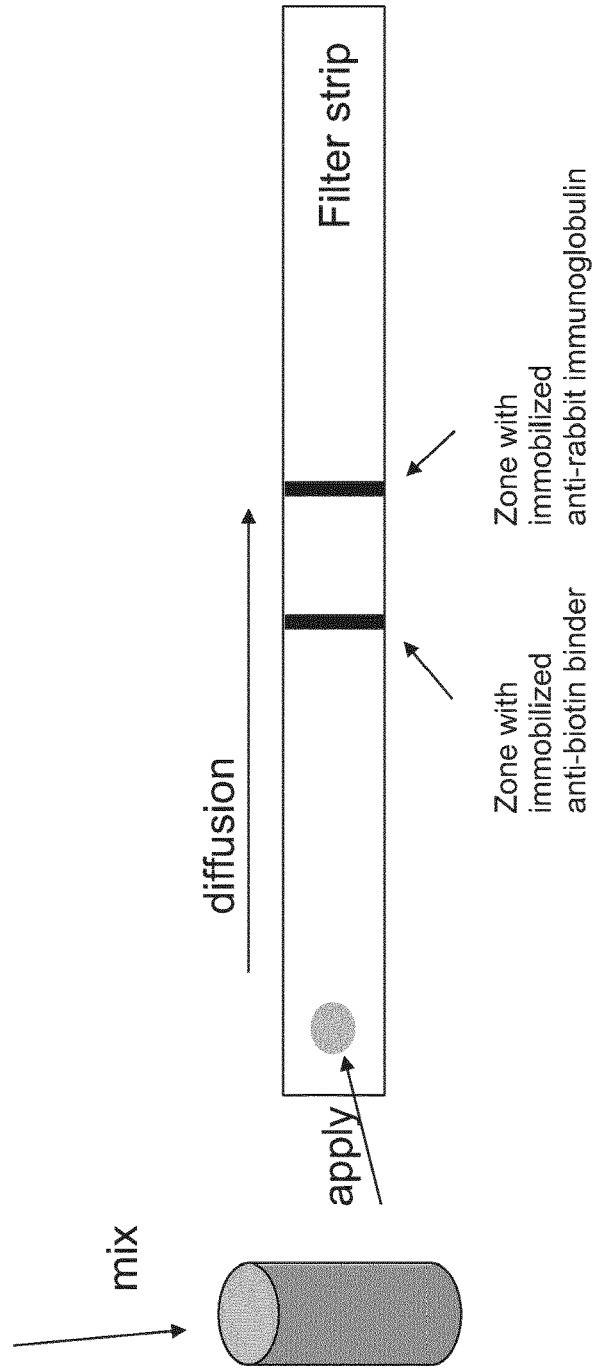
FIG. 15 shows a scheme of a rapid assay for detecting non-core fucosylated (Lewis-glycosylated) secretory immunoglobulins.

Lateral flow tests (Lateral Flow Immunochromatographic Assays) are a simple device intended to detect the presence of a target analyte in a sample. Often produced in a dipstick format, Lateral flow tests are a form of immunoassay in which the test sample flows along a solid substrate via capillary action. After the sample is applied to the test it encounters a coloured reagent which mixes with the sample and transits the substrate encountering lines or zones which have been immobilized binding proteins. Depending upon the analytes present in the sample the coloured reagent can become bound at the test line or zone. A scheme of such an assay is shown in FIG. 15.

A lateral flow immunoassay can be performed within 15 min and can be used to select milk or whey samples containing immune complexes with increased non-core fucosylation.

The specifications for the assay are the detection of non-core glycosylated Secretory Component in milk or whey matrix, at a certain threshold of glycosylation (expressed in mol non-core fucose per mol Secretory Component). For the optimization of such an assay, purified SIgA with no, low and high non-core fucosylation (as determined by glycoanalysis, see for example Example 9) is used.

Such assays with certain specifications can be developed with contracting companies such as Kestrel Biosciences (Carlsbad, USA), Biocare Diagnostics (Xiangzhou, China), Biotem (France) and others.

Alternatively the Assay is designed by using a generic Rapid Assay Device (gRAD, RapidAssays, Copenhagen, Denmark). Basically, a biotinylated capture reagent, a gold-labelled detection reagent and the sample is mixed and then applied to a lateral flow assay device. The gRAD device used in this example contains an immobilized anti-rabbit antibody zone and a biotin-binding zone (control).

The capture reagent in this example is biotinylated DC-SIGN-Fc fusion protein.

The gold labeled detection antibody in this example is a rabbit anti-goat-IgA.

The detection and capture reagents are produced according to the instructions provided by RapidAssays, Denmark. The assay is the optimized according to the instructions of the RapidAssays reagent kits.

Biotinylation:

DC-SIGN-Fc (R&D Systems, no. 161-DC-050) is first mixed with biotinylation reagent which reacts with free primary amine present on the protein. The non-protein coupled biotin reagent is then removed via chromatography. For use with the gRAD the linker should be as long as possible. EZ-Link NHS-PEG12-Biotin, Biotin-NHS, Biotin-LC-NHS and Biotin-PEG4-NHS (Pierce) should be tried and compared in the Assay optimization phase.

PBS pH 7.4 and 100 mM carbonate buffer pH8.0, respectively are used for the biotinylation of DC-SIGN-Fc (it must not be in Tris buffer or contain sodium azide as these will block conjugation). DC-SIGN-Fc concentration should be at 1 mg/ml.

2 µl of biotinylation stock (Stock concentrations in mg/ml DMSO: Biotin-NHS (40), Biotin-LC-NHS (53), Biotin-PEG4-NHS (69), Biotin-PEG12-NHS (110)) is added per mg of DC-SIGN-Fc.

The reaction mixture is then mixed at room temperature in the dark for 2 hours. The remaining active biotin-NHS is blocked with the addition of 10 µl of 3 M ethanolamine and incubating for a further 30 minutes.

Gel filtration/buffer exchange with Sphadex G25 media is used to remove the free biotin. For smaller volumes gel filtration can be carried out with small disposable columns for example a PD10 (General Electric). The process is repeated to remove as much of the free biotin as possible as it will compete for binding to the test line lowering the resulting response.

Preparation of the Colloidal Gold Coated Detection Reagent (According to RapidAssays Instructions):

Polyclonal rabbit anti-goat-IgA (Acris Antibodies GmbH, Germany, no. AP05548PU-N) is used and is prepared to be at a concentration of 1 mg/ml or greater and should be in a 0.5×PBS buffer solution.

Naked Gold Sol 40 nm and Naked Gold Sol 20 nm are used.

1. Shake or swirl gold to resuspend any settled gold. Place 0.5 ml Naked Gold sol into ten (10) clean individual test tubes.

2. Label each tube with the pH value (or, 1 through 10) from the provided pH charts: pH5.4, pH6.6, pH7.3, pH7.8, pH8.2, pH8.4, pH8.8, pH9.2, pH9.6, pH10.1

3. Use the pH charts to add varying amounts of buffer in microliters to each test tube. Shake to mix.

4. Place each tube on a low speed vortexer and add antibody solution (See Sample Preparation Section). Mix thoroughly (about 2 to 3 seconds).

Ideally, for the 40 nm gold, 7 µl of a 2 mg/ml solution of antibody is optimal. For the 20 nm gold, ideally, 14 ul of a 2 mg/ml solution of antibody is optimal.

5. A deepening purple colour and/or black precipitate on some tubes indicates that the antibody or protein is below its iso-electric point, leading to cross-linking of individual gold sols. Cross-linked sols cannot be used in immunological assays and should be discarded. Deep purple sols are usually mostly inactive as well. Only tubes with a slight purple colour or no change in colour are useful for immunological assays.

6. Allow the reaction to continue for a total of 30 minutes.

7. Stop the reaction by the addition of 50 µl of Blocking Stabilizer Solution.

It is best to allow the blocker to react for an additional 16 hours at room temperature.

In order to test the effectiveness of the conjugation reaction, 10 µl of coated gold sol (prior to the addition of the BSA blocking solution) is mixed with 10 µl of 1 M NaCl. Sols with incomplete coating will fall out of solution (turn black), while completely coated sols will remain stable (red).

The Lateral Flow assay is then optimized with the reagents as described above and gRAD devices according to the manufacturer (RapidAssays, Denmark). SIgA, purified from goat milk, and analysed for Lewis glycosylation is used for optimization procedures. SIgA with 0.00 mol non-core fucose/mol Secretory Component is used as negative control. As a positive control, goat SIgA with a predefined non-core fucosylation is used (if screening for milk containing SIgA with at least 0.01 mol non-core fucose/mol Secretory Component is desired, then a SIgA preparation with this amount of glycosylation is used as a reference, e.g. sample 12 of Example 9, for optimization. As a matrix, goat milk with no Lewis glycosylation is used. 50 µg of purified SIgA is added per ml of matrix. These mixtures are used as positive and negative samples for test optimization.

In order to provide for milk with elevated levels of non-core fucosylated secretory immunoglobulins at large scale, potential milk sources are tested for non-core fucosylated immunoglobulin with the described assay.

Only positive (i.e. Non-core fucosylation above threshold) samples are selected for pooling.

Example 9

Glycan Analysis of Goat Secretory Components Showing the Major Fucosylated Structures The following sequence of goat Secretory Component was used for analysis (SEQ ID 17)

MSRLFLACLLAVFPVVSMKSPIFGPKEVTSVEGRSVSITCYYPATSV

NRHTRKYWCRQGATGRCTTLISSEGYVSDDYVGRANLTNFPESGTFV

VDISHLTRNDSGRYKCGLGISSRGLNFDVSLEVSQDPAQASDAHIYP

-continued

VDVGRTVTINCPFTSANSQKRKSLCKKTGQGCFLIIDSTGYKNENYE

DRIRLNIAGTDTLVFSVVINRVLLSDAGTYVCQAGDDAKADKSNVYL

QVLEPEPELVYRDLRSSVTFDCSLGPEVANTAKFLCQQKNGEACNVV

INTLGKKAQDFQGRILFLPKDNGVFSVHIASLRKEDAGRYVCGGQPE

GQPEKGWPVQAWELFVNEETAIPASPSVVKGVKGGSVTVSCPYNPKD

ANSAKYWCRWEEAQNGRCPRLVQSKGLVKEQYKGRLALLAQPGNGTY

TVILNQLTDQDAGFYWCVTDGDTSWTSTVQLKVVEGEPSLKVPKNVT

AWLGEAFKLSCHFPCKFYSFEKYWCKWSNEGCSPLPTQNDGPSQAFV

SCDQNSQIVSLNLDTVTKEDEGWYWCGVKEGPRYGETAAVYVAVESR

AKGSQDAKQVNAAPAGGAIESRAGEIQNKALLDPRLFVEEIAVKDAA

GGPGAPADPGRPAGHSGSSK (Letters in bold indicate the N-glycosylation sites.)

Overall Glycosylation

Secretory Immunoglobulin is prepared according to Example 11. The purified secretory immunoglobulin is separated into Secretory Component, J-chain, H-chain, and light chain by reducing SDS-PAGE (80×80×1 mm, 10% BisTris NuPAGE gel, MES SDS running buffer (Invitrogen)). The protein bands are visualized by Coomassie staining. Molecular mass standards are used. The approx. 80 kDa Coomassie stained bands are excised and in-gel. Glycans were released from the Secretory Component using PNGAseF directly from the SDS page gel before tryptic digest for 16 hrs with subsequent borohydride reduction (PNGAse F/A digest after protease treatment with trypsin remained glycosite Nr.4 undigested and therefore would have been not complete). Glycan analysis was done per PGC (porous graphitized carbon chromatography) and ESI-MS detection. Before injection to the analysis system, glycans were de-sialylated using a linkage unspecific sialidase from *Clostridium perfringens* and analyzed according to elution times. Glyans with non-core fucose and core fucose can be separated and are represented in percent of the complete glycans.

Glycopeptide Analysis

Glycosites are analyzed in the same way as peptides by using RP-ESI-MSMS. Structures are eluting according to the peptide backbone and show a certain mass distribution due to glycosylation heterogeneity.

Analysis of peptides and glycopeptides is performed on a capillary LC-ESI-MS system consisting of an Aquasil C-18 precolumn (30 mm×0.32 mm, 5 micrometer, Thermo Scientific), a BioBasic C18 analytical column (150 mm×0.18 mm, 5 micrometer, Thermo Scientific), a Waters CapLC, a Rheodyne 10-port valve and a Waters Q-TOF Ultima with standard ESI-source. Solvent A consists of 65 mM ammonium formate of pH 3.0 and solvent B is 80% acetonitrile (ACN) in solvent A. The precolumn is equilibrated and loaded in the absence of ACN. Thereafter, a gradient from 6.3 to 62.5% solvent B is developed over 45 min. Positive ions in the range from m/z 150 to 1800 are measured. Capillary voltage is 3.2 kV and cone voltage 35 V, source temperature is 100° C., desolvation temperature 120° C.

Data are evaluated using MassLynx 4.0 software including MaxEnt3 deconvolution/deisotoping feature (Waters). The glycosylated peptides are identified by deglycosylation with PNGnase F (Roche) and further separation in reverse phase HPLC followed by mass spectroscopy. The deglycosylated peptide contains a glutamic acid instead of a glutamine residue, which results in a mass difference of 1 Da.

Different glycan structures on the same peptide backbone divide the possible glycopeptide signal into several molecular species of different mass. The presence of glycopeptides can also be indicated in a total mass spectrum as a ladder of masses with steps based on specific monosaccharide differences (e.g., m/z 146 [Fucose], 162 [Hexose], 203 [N-acetylhexosamine], 291 [N-acetyl neuraminic acid]) between the different glycoforms.

Once the glycopeptide peaks are identified, the peak "volume", i.e. the area under the peaks corresponding to a particular glycopeptide is measured. The peak volume can be translated directly into molar proportions of glycoforms as the ionization and hence detection of the glycopeptides is dominated by the peptide portion. The mass spectra are acquired over the elution time of an identified or potential glycopeptide and are summed, smoothed and centroided before the m/z vs intensity spectrum is submitted to the software for analysis.

To increase signal-to-noise ratio for low intensity glycoforms, it is recommended to sum the MS-spectra only over the respective elution peak rather than over a wider chromatographic time frame. From the list of glycoforms occurring on a particular glycosylation site, the molar fraction of fucosylated glycans is calculated. The results for the different sites are added to arrive at the molar proportion fucosylated glycans occurring in the Secretory Component.

The following glycosite peptides were identified:

```
            glycosite no.1
            position 82-89
                                    (SEQ ID 18)
ANLTNFPE glycosite no.2
            position 103-107
                                    (SEQ ID 19)
NDSGR glycosite no.3
            position 412-455
                                    (SEQ ID 20)
LALLAQPGNGTYTVILNQLTDQ
DAGFYWCVTDGDTSWTSTVQLK glycosite no.4
            position 468-476
                                    (SEQ ID 21)
NVTAWLGE
```

While Glycosites 1, 2 and 4 could be detected during the analytical procedure, glycosite peptide no. 3 remained unexplored, also using other proteases and mass spectrometers.

The table below shows the molar content of non-core fucose of Secretory Component various goat milk samples.

TABLE 1

Goat Secretory Component analysis for non-core fucose (at glycosylation sites 1, 2 and 4 (mmol per mol SC))

| Sample no. | non-core fucose (mmol per mol SC) |
|---|---|
| 5 | 1.99 |
| 6 | 3.08 |
| 11 | 9.00 |
| 12 | 18.47 |
| 13 | 5.32 |
| 21 | 4.64 |
| 22 | 0.00 |

TABLE 1-continued

Goat Secretory Component analysis for non-core fucose (at glycosylation sites 1, 2 and 4 (mmol per mol SC))

| Sample no. | non-core fucose (mmol per mol SC) |
|---|---|
| 23 | 0.60 |
| 27 | 4.95 |
| 30 | 0.12 |
| 32 | 4.96 |
| 33 | 3.82 |

Example 10

Cell Cytotoxitity Assay

Vero cells are grown to a confluent monolayer and subcultured by incubation 2 ml of 0.1% trypsin in 1 mM EDTA. Cells are counted and $6.25 \times 10^4$ cells/ml are seeded into 96-well plates in a total volume of 80 µl. The plates are incubated for 20-24 h in 37° C. and 5% $CO_2$. *Clostridium difficile* Toxin A (List Biological Laboratories, Campbell, Calif., USA, cat. no. 152) is diluted with PBS (PAA, Austria) to a final concentration of 0.2 µg/ml and incubated with dilutions of human hSIgA (Sigma no. 11010), respectively, bovine SIgA (<10 mmol non-core fucose/mol) and goat SIgA obtained according to Example 11 (Sample No. 6<10 mmol non-core fucose/mol, Sample No. 12>10 mmol non-core fucose/mol) for 1 h at 37° C. Human SIgA is used in a tenfold molar surplus as compared to toxin as well as equimolar. Bovine and goat SIgA is used equimolar. Bovine serum albumine (New England Biolabs) and PBS (phosphate buffered saline) serve as negative controls. Toxin A/antibody mixtures are added to 96-well plates in a randomized order and incubated for additional 48 h. 10 µl WST-8 (Sigma) is added to each well and the plates are incubated for 2-4 h at 37° C. Viable cells produce a water-soluble yellow formazan dye via reduction with dehydrogenases which is proportional to the cell number. Absorbance at 450 nm is determined using a microplate reader (Tecan® Infinity-1000). Each data point is performed in triplicates. FIG. 16 shows results of two SIgA goat samples, one bovine SIgA sample and the human hSIgA sample as control. The result shows that the level of neutralization of Toxin A in this assay correlates with the amount of non-core fucosylation on the respective samples.

Example 11

Preparation of Secretory Immunoglobulin from Milk Samples

This example describes the pilot scale preparation of secretory immunoglobulin from milk samples.

Materials and Methods

Preparation of Whey

For all centrifugation steps a Beckman-Coulter™ Avanti J-25 centrifuge with the rotor JLA10.500 was used. Beakers with a nominal volume of 0.5 L were used, but were filled only up to 0.4 L.

Delipidation

Delipidation was performed by centrifugation at 11827 g (8000 RPM), for 30 minutes at room temperature. The supernatant was used for further preparation. The pellet (fat) was discarded.

Acidic Precipitation of Casein

Acidic precipitation was performed by slowly adding a 5% HCl solution under constant vigorous stirring of the delipidated milk until a pH of 4.6 was obtained.

Removal of Precipitate

Removal of the precipitate was performed by centrifugation at 14969 g (9000 RPM), for 45 minutes at room temperature. The supernatant was used for further preparation. The pellet (precipitate) was discarded.

Depth Filtration

The whey was filtrated using a peristaltic pump (Watson-Marlow X-100) and a sterile filter unit (Sartorius-Stedim Sartobran P 0.45+0.2 μm pore size; filtration area 0.1 $m^2$).

Ultra/Diafiltration

Equipment

Millipore Labscale™ TFF System

Millipore Cogent μScale TFF System

Filtration membranes

GE Healthcare Kvick™ Start 100 kD 50 $cm^2$

GE Healthcare Kvick™ Lab 100 kD 100 $cm^2$

Concentration and Diafiltration of Whey

For the Millipore Labscale™ TFF System 3 membranes were used for ultra- and diafiltration of whey, with a total membrane area of 0.015 $m^2$. The pump setting was 2 and a transmembrane pressure of approximately 2.5 bar was adjusted. The whey was concentrated ~1:25 and diafiltrated with phosphate buffered saline (PBS) whereas the concentrated whey was buffer exchanged with a 7-fold excess of PBS.

Millipore Cogent μScale TFF System: 3 membranes with a total membrane area of 0.03 $m^2$ were used. The pump setting was 40% of the maximum flow, corresponding to approximately 150 mL/min, the transmembrane pressure 2.5 bar.

Permeate flux was measured by weighing permeate sample at distinct time intervals.

Preparative SEC

Superose 6

Superose 6 prep grade packed into a HiScale™ column 26/40 was used. The bed height was 32.5 cm and the column volume was 173 mL. The flow rate was 30 cm/h (2.65 ml/min) and the sample volume was 15 mL, corresponding to 4.7% of the column volume (CV). Fractionation was performed from 0.3 CV to 0.57 CV with a fraction size of 5 ml. The equilibration and running buffer was 1×PBS.

Superdex 200

A Superdex 200 prep grade HiLoad™ column 26/60 was used. The bed height was 59.7 cm and the column volume was 317 mL. Running conditions were same as described for Superose 6.

Milk Samples

Bovine and sheep milk was obtained form local food stores, all samples of goat whey and goat milk were obtained from Hofkäserei Dörfl (Untere Bergstrasse 1, 3041 Dörfl, Austria).

Analytical SEC

A HP Chemstation 1100 (Agilent) was used for analytical SEC. Columns were Superose 6 10/300 GL and Superdex 200 10/300 GL, both from GE Healthcare. The flow rate was 0.5 mL/min and the injection volume was 50 μL. The equilibration and running buffer was 1×PBS. UV signals were recorded at 214 nm.

SDS-Page

Samples were added with DTT to a final concentration of 200 mM and NuPAGE LDS Sample Buffer (4×) and were boiled for 10 minutes. Samples were loaded onto Tris-Acetate 3-8% gels, the running buffer was 1× NuPAGE Tris-Acetate SDS Running Buffer. The running conditions were 150 V, max Ampere, 1.5 hours. The marker was Invitrogen HiMark Pre-Stained High Molecular Weight Protein Standard. Protein staining was performed with Coomassie Blue.

Dot-Blot

5 μl portions of samples from preparative SEC runs were applied to a nitrocellulose membrane. After air-drying of the samples, membranes were blocked with 3% BSA for 1 hour and washed 3× with PBS buffer containing 0.1% Tween 20 (wash buffer). Afterwards membranes were incubated with specific antibody-HRP conjugates for 1 hour. Following conjugates were used: 1) Rabbit-anti-goat-IgM-HRP, product number AAI45P; 2) Rabbit-anti-goat-IgG(H/L)-HRP, product number 5160-2504; 3) Rabbit-anti-goat-IgA-HRP, product number AAI44P (AbD Serotec, Germany). The conjugate stock was diluted 1:30000-1:50000 with wash buffer containing 1% BSA. After washing 3× with wash buffer, signalling was performed with SuperSignal West Pico Chemiluminescent Substrate (Pierce, Germany) and the Lumi-Imager™ scanner from Boehringer Mannheim.

A complete mass balance of the process was established as described in 3.4.1 and is shown for two goat milk samples (Samples No. 11 and 12 of Example 9) in Table 2. All peak profiles from the HPLC analysis were deconvoluted into its individual immunoglobulins. The SIgA content was then calculated based on the purity and the amount of protein obtained from the preparative run data. IgA content of goat milk from literature data is 30-80 μg/ml. These values served as a base for the calculation of theoretical yield.

TABLE 2

Mass balance, yield and purity of processing of samples 11 and 12

| | Sample 11 | Sample 12 |
| --- | --- | --- |
| Initial volume milk [mL] | 900 | 900 |
| Volume whey [mL] | 875 | 875 |
| Volume concentrated whey [mL] | 35 | 35 |
| Concentration factor | 1:25 | 1:25 |
| Sample volume concentrated whey applied [mL] | 15 (42% of total volume) | 15 |
| Fractionation (fraction size, fractions containing IgA) | 5 ml, F7-F9 | 5 ml, F6-F10 |
| C (IgA) fraction F6 [μg/mL]; total amount [μg]; purity % | — | 295; 1475; 24% |
| C (IgA) fraction F7 [μg/mL]; total amount [μg]; purity % | 308; 1540; 39% | 412; 2060; 40% |
| C (IgA) fraction F8 [μg/mL]; total amount [μg]; purity % | 420; 2101; 76% | 782; 3910; 90% |
| C (IgA) fraction F9 [μg/mL]; total amount [μg]; purity % | 403; 2017; 71% | 305; 1527; 44% |
| C (IgA) fraction F10 [μg/mL]; total amount [μg]; purity % | — | 172; 861; 36% |
| Total amount IgA [mg]; theoretical yield[1] [mg] (%) | 5.7; 11.6-30.8 (49-19%) | 9.8; 11.6-30.8 (84-32%) |

[1]theoretical amount of total IgA based on 42% of sample volume was used

Example 12

ELISA for DC-SIGN Binding

This example shows that it is possible to screen individual milk samples for

Lewis-specific glycosylation on secretory IgA. The lectin DC-SIGN is known to bind to Lewis blood group structures and can therefore be used as a screening antigen.

Screening ELISA for DC-SIGN Reactivity of SIgA in Individual Goat Milk Samples

The ELISA is performed in 96 well NUNC immunplates.

Coating: DC-SIGN-Fc fusion protein (R&D Systems, no. 161-DC-050; Stocksolution 100 µg/ml) diluted 1:100 in fresh coating Buffer 100 µl/well, incubation for 4° C. over night. Wash 3× with PBS-Tween, afterwards incubate with PBS-Tween 300 µl/well for 30 min at room temperature. Wash 3× with PBS-Tween.

Sample preparation: 10 ml Milk from individual goats is sampled freshly and centrifuged at 40,000×g for 30 min at 4° C. The fat layer is removed with a spatula; the remaining liquid is transferred into a new centrifuge tube and centrifuged again at 40,000×g for 30 min. The liquid layer (milk serum) is aliquoted and stored at −20° C. or used for screening directly.

As a positive sample, human hSIgA (Sigma no. I1010) is used at a concentration of 5 µg/mL.

As negative control goat milk "Ja Natürlich" Ziegenmilch, Sennerei Zillertal, Austria, is used.

Samples are added always in two dilutions, 1:2 and 1:10 diluted in Conjugate Buffer, 100 µl/well, incubation for 2 h at room temperature.

After 3 washings with PBS-Tween, conjugate is added to the wells (100 µl, rabbit anti-goat IgA-Alkaline phosphatase conjugate, abcam no. ab112864, diluted 1:1000 in conjugate buffer) and incubated for 1.5 hours at room temperature in the dark.

For the positive controls, anti-human IgA-Alkaline phosphatase (Acris no. R1342AP, 1:1000) is used. The wells are subsequently washed 3 times with PBS-Tween. Detection is done with 100 µl colorigenic substrate (1 mg para-nitrophenylphosphate/ml staining buffer), incubation at room temperature.

The plates are measured after 30 minutes in a microplate photometer at 405 nm (reference wavelength 620 nm).

Coating buffer: 0.42 g Na$_2$CO$_3$+0.84 g NaHCO$_3$+100 ml A.D., =pH 9.7, store at 4° C., use max. 3 days Blocking solution/Washing Buffer: 100 ml PBS+100 µl Tween 20 (=0.1%), always FRESH Conjugate buffer: 10 g PVP+250 µl Tween 20+0.1 g MgCl$_2$+500 ml PBS, adjust pH to 7.4

Store at 4° C., preserve optionally by adding NaH$_3$

Staining buffer: 47.8 ml di-ethanolamin+3.3 ml 75 mM MgCl$_2$ sol.+448.9 ml A.D., adjust pH to 9.8 (when in hurry, coating buffer can be used instead, but signal will be weaker), store at 4° C., preserve optionally by adding NaH$_3$ Results of 2 ELISA plates are shown in FIG. 17

Statistical evaluation of the ELISA data (only OD (optical density) values of dilution 1:2 are used for exemplifying the evaluation):

Plate A:
Mean OD of negative controls: 0.082
Standard deviation of negative controls: 0.061
Threshold for positivity (mean of controls plus 3 times standard deviation): 0.265
Positive Samples (OD above threshold)

| sample 41 | (1.041) |
|---|---|
| sample 48 | (0.744) |
| sample 56 | (0.691) |
| sample 69 | (0.286) |

Plate B:
Mean OD of negative controls: 0.130
Standard deviation of negative controls: 0.074
Threshold for positivity (mean of controls plus 3 times standard deviation): 0.352
Positive Samples (OD above threshold)

| sample 90 | (0.584) |
|---|---|
| sample 91 | (0.385) |
| sample 107 | (1.627) |
| sample 109 | (0.498) |
| sample 112 | (1.100) |
| sample 115 | (0.371) |
| sample 132 | (0.889) |

All positive samples are pooled.

Positivity for DC-SIGN binding (which corresponds to Lewis-glycosylation) may be due to differences of these animals as compared to other animals in terms of race, feeding, health status etc.

For industrial preparation of milk containing the immune complex according to the invention, individual animals are retested in regular intervals in order to ensure collection of milk with high non-core fucosylated Secretory Immunoglobulin.

Milk from such animals producing DC-SIGN positive ELISA results is collected separately and subsequently processed. As soon as milk from an individual is tested to be negative, subsequent milk from the respective individual is not any longer used for preparation of a pool of milk containing Lewis-glycosylation-enriched Secretory Component and immune complexes.

When a sample of at least 10 mmol non-core fucose per mol SC or SIgA is used as a reference, the test can be calibrated to determine the level higher or lower than the reference.

Example 13

Binding of Recombinant Human SC to DC-SIGN

In order to show the surprising effect of non-core fucosylation of recombinant SC, the protein is produced by transfection of the gene for SC into appropriate cells. The gene of FIG. 2 is inserted at the HindIII and XbaI sites in the vector pCDNA3.1+(invitrogen, USA) as described in example 2 into CHO LEC11 (cell line and transfection techniques according to Rittershaus et al. J Biol Chem. Vol. 274, pp. 11237-44).

As a control, CHO DUK-(ATCC CRL 9096) according to Phalipon et al. 2002, Immunity, Vol. 17, pp 107-115) is used as expression host for the secretory component gene.

Supernatants of CHO clones are tested in ELISA specific for Secretory Component and Lewis glycosylation:

Screening is performed in a standard ELISA format. Cell culture supernatants ELISA plates (Nunc Maxi-Sorp Immuno Plate) are coated with anti-human-secretory component antibodies (Ray Biotech no. DS-PB-03010, USA) at a concentration of 1 microgram per ml coating buffer (3.03 g Na$_2$CO$_3$, 6.0 g NaHCO$_3$ in 1000 ml distilled water, pH 9.6) at 100 microliters per well.

The plates are closed with a lid and incubated overnight at 4° C.

Before the next step the coating solution is removed and the plates are washed three times by filling the wells with 200 µl TPBS (1.16 g Na$_2$HPO$_4$, 0.1 g KCl, 0.1 g K$_3$PO$_4$, 4.0 g NaCl in 500 ml distilled water, 0.05% (v/v) Tween20, pH 7.4). The solutions or washes are removed by flicking the plate over a sink. The remaining drops are removed by patting the plate on a paper towel. Alternatively, washing can be performed with an ELISA washer.

Plates are filled with Superblock blocking buffer (Thermo no 37515) 150 microliters/well and incubated at room temperature for 2 hours.

Again, the plates are washed as described above.

The cell culture supernatants are diluted in sample TPBS (1:2 and 1:10). 16 negative controls for each dilution (1:2 and 1:10) are added to each plate. 4 positive control samples for each dilution are added to the plate. 100 microliters of the respective dilutions are added into wells of the washed plate and incubated at room temperature for 2 hours.

After washing, 100 microliters of anti-sialyl Lewis x-antibody (Merck Millipore, MAB2096) at a dilution of 1:100 in TPBS are added to the respective sample wells and to the negative and positive control sample wells.

The plate is again incubated for 2 hours at room temperature and subsequently washed.

Then, 100 microliters per well of a chicken anti-mouse-IgG-HRP (Thermo, no. SA1-72029, 1:500 in TPBS) is added and incubated for 2 hours at room temperature. Subsequently, the plates are washed three times with TPBS.

A further washing step is then performed with substrate buffer (TMB Substrate kit; Vector Laboratories no SK-4400, USA). Thereafter, chromogenic substrate is added (Vector Laboratories SK-4400). After short incubation (measurement of positive control at OD 650>1.0, negative control OD<0.2) 50 microliters of 1 N sulfuric acid are added and the plate is read in the microplate reader at OD450, compensated by OD600 as in standard ELSA techniques utilizing TMB as substrate.

It can be shown that recombinant human SC expressed in LEC11 displays sialyl-Lewis x. In contrast, expression of recombinant SC in normal CHO (CHO DUK-) does not show any non-core fucosylation.

Purification:

Purification of recombinant Secretory Component from supernatant of animal cells and secretory IgA is performed by affinity chromatography with rabbit-anti-human Secretory Component coupled to Sepharose according to standard protocols for affinity chromatography.

Desialylation:

100 microgram of recombinant SC is desialylated in a reaction volume of 30 microliter with 0.1 units Sialidase A (Prozyme, Cat. no. GK80040) in 50 mM sodium phosphate buffer, pH 6.0 at 37° C. for 8 hours.

After desalting via PD SpinTrap G-25 (GE Healthcare, cat. no. 28-9180-04) according to the manufacturer the recombinant SC protein is being testet in an ELISA for binding to DC-SIGN

DC-SIGN ELISA

The ELISA is performed in 96 well NUNC immunplates.

Coating: DC-SIGN-Fc fusion protein (R&D Systems, no. 161-DC-050; stock solution 100 µg/ml) is diluted 1:100 in fresh coating buffer (0.42 g Na2CO3+0.84 g NaHCO3+100 ml A.D., =pH 9.7, store at 4° C., use max. 3 days).

The coating is added at 100 µl/well, incubation is performed for 4° C. over night.

Wash 3× with PBS-Tween, afterwards incubate with PBS-Tween with 300 µl/well for 30 min at room temperature. Wash again 3× with PBS-Tween.

Samples:

Recombinant SC preparations produced with CHO DUK-cells as well as with CHO LEC11, before and after sialidase treatment respectively at a starting concentration of 1 microgram per ml are serially diluted (in 1:5 steps) in conjugate buffer. 100 µl of each dilution is added in duplicates to the coated plate and incubated for 2 h at room temperature.

After 3 washings with PBS-Tween, conjugate is added to the wells (100 µl, anti-human SC-HRP conjugate, *Acris* no. AP21476HR-N, diluted 1:1000 in conjugate buffer) and incubated for 1.5 hours at room temperature.

The wells are subsequently washed 3 times with PBS-Tween. A further washing step is then performed with substrate buffer (TMB Substrate kit; Vector Laboratories no SK-4400, USA). Thereafter, chromogenic substrate is added (Vector Laboratories SK4400). After short incubation 50 microliters of 1 N sulfuric acid are added and the plate is read in the microplate reader at OD450, compensated by OD600 as in standard ELSA techniques utilizing TMB as substrate.

Blocking solution/Washing Buffer: 100 ml PBS+100 µl Tween 20 (=0.1%)

Conjugate buffer: 10 g PVP+250 µl Tween 20+0.1 g MgCl2+1 mM CaCl2+500 ml PBS, adjust pH to 7.4

PBS is phosphate buffered saline with 1 mM Ca.

Store at 4° C., preserve optionally by adding NaH3

It can be shown that the desialylated recombinant SC from CHO LEC11 binds stronger to DC-SIGN as compared to the desialylated secretory component produced in CHO CHO DUK—as well as the sialylated SC expressed in CHO LEC11.

The invention claimed is:

1. A preparation of recombinant human secretory component (SC) molecules having a Lewis-type N-glycosylation pattern and at least 2 mol non-core fucose per mol SC, wherein the SC is obtained by expressing the SC from a recombinant production host cell line expressing a heterologous functional alpha-1,x-fucosyltransferase, and wherein x is 2, 3, or 4, wherein at least 90% of the SC molecules have the same C-terminus.

2. The SC according to claim 1, wherein the production host cell line is a CHO cell line.

3. The SC according to claim 1, wherein the SC comprises the amino acid sequence of human SC as provided in SEQ ID NO:1, or a functionally active variant thereof which comprises at least the first extracellular domain of SC, or which is truncated at any amino acid site between K566 and E607 of SEQ ID NO:1.

4. The SC according to claim 1, wherein the SC comprises sialic acid.

5. The SC according to claim 4, wherein the SC comprises at least 2 mol sialic acid per mol SC.

6. The SC according to claim 4, wherein the SC comprises less than 0.1 mol sialic acid per mol SC.

7. The SC according to claim 1, wherein the SC is non-sialylated.

8. A composition comprising:
   recombinant human secretory component (SC) molecules having a Lewis-type N-glycosylation pattern and at least 2 mol non-core fucose per mol SC, wherein the SC is obtained by expressing the SC from a recombinant production host cell line expressing a heterologous functional alpha-1,x-fucosyltransferase, and wherein x is 2, 3, or 4, wherein at least 90% of the SC molecules have the same C-terminus; and
   one or more pharmaceutically acceptable additives for mucosal administration.

9. The composition of claim 8, wherein the composition is in the form of a syrup, a lozenge, a tablet, a spray, an inhalator formulation, a powder, granules, a suppository, a capsule, a cream, a paste, a gel, or drops.

10. The composition of claim 8, wherein the composition is in a dried form.

11. An immune complex preparation comprising the SC according to claim 1 and at least one of IgA or IgM immunoglobulins.

12. The immune complex preparation according to claim 11, wherein the immunoglobulins are human immunoglobulins.

13. The immune complex preparation according to claim 11, wherein the immunoglobulins have a human glycosylation pattern.

14. The immune complex preparation according to claim 11, wherein the immunoglobulins are plasma immunoglobulins.

15. The immune complex preparation according to claim 11, wherein the IgA is dimeric IgA.

16. The immune complex preparation according to claim 11, wherein the preparation is in the form of a liquid, an emulsion, or a suspension, or is in dried form.

17. The immune complex preparation of claim 16, wherein the preparation is a food product or a medicament.

18. The immune complex preparation of claim 16, wherein the preparation is formulated for oral or mucosal administration.

* * * * *

SEQUENCE LISTING

```
<160> NUMBER OF SEQ ID NOS: 21

<210> SEQ ID NO 1
<211> LENGTH: 607
<212> TYPE: PRT
<213> ORGANISM: human

<400> SEQUENCE: 1

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60
```

```
Ile Thr Leu Ile Ser Ser Glu Gly Tyr Val Ser Lys Tyr Ala Gly
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
            115                 120                 125

Gln Gly Pro Gly Leu Leu Asn Asp Thr Lys Val Tyr Thr Val Asp Leu
130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
            195                 200                 205

Gln Leu Arg Leu Ser Asp Ala Gly Gln Tyr Leu Cys Gln Ala Gly Asp
210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Val Asn Thr Leu Gly Lys
            275                 280                 285

Arg Ala Pro Ala Phe Glu Gly Arg Ile Leu Leu Asn Pro Gln Asp Lys
290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
            340                 345                 350

Pro Arg Ser Pro Thr Val Val Lys Gly Val Ala Gly Ser Ser Val Ala
            355                 360                 365

Val Leu Cys Pro Tyr Asn Arg Lys Glu Ser Lys Ser Ile Lys Tyr Trp
370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
            435                 440                 445

Trp Arg Thr Thr Val Glu Ile Lys Ile Ile Glu Gly Glu Pro Asn Leu
450                 455                 460

Lys Val Pro Gly Asn Val Thr Ala Val Leu Gly Glu Thr Leu Lys Val
465                 470                 475                 480
```

```
Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
        500                 505                 510

Pro Ser Lys Ala Phe Val Asn Cys Asp Glu Asn Ser Arg Leu Val Ser
            515                 520                 525

Leu Thr Leu Asn Leu Val Thr Arg Ala Asp Glu Gly Trp Tyr Trp Cys
        530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
                565                 570                 575

Lys Ala Asp Ala Ala Pro Asp Glu Lys Val Leu Asp Ser Gly Phe Arg
            580                 585                 590

Glu Ile Glu Asn Lys Ala Ile Gln Asp Pro Arg Leu Phe Ala Glu
                595                 600                 605

<210> SEQ ID NO 2
<211> LENGTH: 1844
<212> TYPE: DNA
<213> ORGANISM: human

<400> SEQUENCE: 2
ccccaagctt atgctgctgt tcgtgctgac ctgcctgctg gccgtgttcc ccgccatcag    60
caccaagagc cccatcttcg ccccgagga ggtgaacagc gtggagggca cagcgtgag    120 catcacctgc tactaccccc ccaccagcgt gaacagacac accagaaagt actggtgcag    180
acagggcgcc agaggcggct gcatcaccct gatcagcagc gagggctacg tgagcagcaa    240
gtacgccgga agagccaacc tgaccaactt ccccgagaac ggcaccttcg tggtgaacat    300
cgcccagctg agccaggacg acagcggcag atacaagtgc ggcctgggca tcaacagcag    360
aggcctgagc ttcgacgtga gcctggaggt gagccaggc cccggcctgc tgaacgacac    420
caaggtgtac accgtggacc tgggcagaac cgtgaccatc aactgcccct tcaagaccga    480
gaacgcccag aagagaaaga gcctgtacaa gcagatcggc ctgtacccg tgctggtgat    540 cgacagcagc ggctacgtga accccaacta caccggcaga atcagactgg acatccaggg    600
caccggccag ctgctgttca gcgtggtgat caaccagctg agactgagcg acgccggcca    660
gtacctgtgc caggccggcg acgacagcaa cagcaacaag aagaacgccg acctgcaggt    720
gctgaagccc gagcccgagc tggtgtacga ggacctgaga ggcagcgtga ccttccactg    780
cgccctgggc cccgaggtgg ccaacgtggc caagttcctg tgcagacaga gcagcggcga    840
gaactgcgac gtggtggtga acaccctggg caagagagcc cccgccttcg agggcagaat    900
cctgctgaac cccaggaca aggacggcag cttcagcgtg gtgatcaccg gcctgagaaa    960
ggaggacgcc ggcagatacc tgtgcggcgc ccacagcgac ggccagctgc aggagggcag    1020 cccccatccag gcctggcagc tgttcgtgaa cgaggagagc accatcccca agagccccac    1080
cgtggtgaag ggcgtggccg gcagcagcgt ggccgtgctg tgcccctaca cagaaaagga    1140
gagcaagagc atcaagtact ggtgcctgtg gagggcgcc agaacggca gatgccccct    1200 gctggtggac agcgagggct gggtgaaggc ccagtacgag ggcagactga gcctgctgga    1260
ggagcccggc aacggcacct tcaccgtgat cctgaaccag ctgaccagca gagacgccgg    1320
cttctactgg tgcctgacca cggcgacac cctgtgagga accaccgtgg agatcaagat    1380
catcgagggc gagcccaacc tgaaggtgcc cggcaacgtg accgccgtgc tgggcgagac    1440
```

-continued

```
cctgaaggtg ccctgccact tcccctgcaa gttcagcagc tacgagaagt actggtgcaa    1500
gtggaacaac accggctgcc aggccctgcc cagccaggac gagggcccca gcaaggcctt    1560
cgtgaactgc gacgagaaca gcagactggt gagcctgacc ctgaacctgg tgaccagagc    1620
cgacgagggc tggtactggt gcggcgtgaa gcagggccac ttctacggcg agaccgccgc    1680
cgtgtacgtg gccgtggagg agagaaaggc cgccggcagc agagacgtga gcctggccaa    1740
ggccgacgcc gccccgacg agaaggtgct ggacagcggc ttcagagaga tcgagaacaa    1800
ggccatccag gaccccagac tgttcgccga gtgatctaga cccc                    1844
```

<210> SEQ ID NO 3
<211> LENGTH: 343
<212> TYPE: PRT
<213> ORGANISM: human

<400> SEQUENCE: 3

```
Met Leu Val Val Gln Met Pro Phe Ser Phe Pro Met Ala His Phe Ile
1               5                   10                  15

Leu Phe Val Phe Thr Val Ser Thr Ile Phe His Val Gln Gln Arg Leu
            20                  25                  30

Ala Lys Ile Gln Ala Met Trp Glu Leu Pro Val Gln Ile Pro Val Leu
        35                  40                  45

Ala Ser Thr Ser Lys Ala Leu Gly Pro Ser Gln Leu Arg Gly Met Trp
    50                  55                  60

Thr Ile Asn Ala Ile Gly Arg Leu Gly Asn Gln Met Gly Glu Tyr Ala
65                  70                  75                  80

Thr Leu Tyr Ala Leu Ala Lys Met Asn Gly Arg Pro Ala Phe Ile Pro
                85                  90                  95

Ala Gln Met His Ser Thr Leu Ala Pro Ile Phe Arg Ile Thr Leu Pro
            100                 105                 110

Val Leu His Ser Ala Thr Ala Ser Arg Ile Pro Trp Gln Asn Tyr His
        115                 120                 125

Leu Asn Asp Trp Met Glu Glu Glu Tyr Arg His Ile Pro Gly Glu Tyr
    130                 135                 140

Val Arg Phe Thr Gly Tyr Pro Cys Ser Trp Thr Phe Tyr His His Leu
145                 150                 155                 160

Arg Gln Glu Ile Leu Gln Glu Phe Thr Leu His Asp His Val Arg Glu
                165                 170                 175

Glu Ala Gln Lys Phe Leu Arg Gly Leu Gln Val Asn Gly Ser Arg Pro
            180                 185                 190

Gly Thr Phe Val Gly Val His Val Arg Arg Gly Asp Tyr Val His Val
        195                 200                 205

Met Pro Lys Val Trp Lys Gly Val Val Ala Asp Arg Arg Tyr Leu Gln
    210                 215                 220

Gln Ala Leu Asp Trp Phe Arg Ala Arg Tyr Ser Ser Leu Ile Phe Val
225                 230                 235                 240

Val Thr Ser Asn Gly Met Ala Trp Cys Arg Glu Asn Ile Asp Thr Ser
                245                 250                 255

His Gly Asp Val Val Phe Ala Gly Asp Gly Ile Glu Gly Ser Pro Ala
            260                 265                 270

Lys Asp Phe Ala Leu Leu Thr Gln Cys Asn His Thr Ile Met Thr Ile
        275                 280                 285

Gly Thr Phe Gly Ile Trp Ala Ala Tyr Leu Thr Gly Gly Asp Thr Ile
    290                 295                 300
```

Tyr Leu Ala Asn Tyr Thr Leu Pro Asp Ser Pro Phe Leu Lys Ile Phe
305                 310                 315                 320

Lys Pro Glu Ala Ala Phe Leu Pro Glu Trp Thr Gly Ile Ala Ala Asp
            325                 330                 335

Leu Ser Pro Leu Leu Lys His
            340

<210> SEQ ID NO 4
<211> LENGTH: 1044
<212> TYPE: DNA
<213> ORGANISM: human

<400> SEQUENCE: 4

| | | | | | |
|---|---|---|---|---|---|
| gctagcatgc | tggtggtgca | gatgccgttt | agctttccga | tggcgcattt | tattctgttt | 60 |
| gtgtttaccg | tgagcaccat | ttttcatgtg | cagcagcgcc | tggcgaaaat | tcaggcgatg | 120 |
| tgggaactgc | cggtgcagat | tccggtgctg | gcgagcacca | gcaaagcgct | gggcccgagc | 180 |
| cagctgcgcg | gcatgtggac | cattaacgcg | attggccgcc | tgggcaacca | gatgggcgaa | 240 |
| tatgcgaccc | tgtatgcgct | ggcgaaaatg | aacggccgcc | cggcgtttat | tccggcgcag | 300 |
| atgcatagca | ccctggcgcc | gattttcgc | attaccctgc | cggtgctgca | tagcgcgacc | 360 |
| gcgagccgca | ttccgtggca | gaactatcat | ctgaacgatt | ggatggaaga | agaatatcgc | 420 |
| catattccgg | cgaatatgt | gcgctttacc | ggctatccgt | gcagctggac | cttttatcat | 480 |
| catctgcgcc | aggaaattct | gcaggaattt | accctgcatg | atcatgtgcg | cgaagaagcg | 540 |
| cagaaatttc | tgcgcggcct | gcaggtgaac | ggcagccgcc | cgggcacctt | tgtgggcgtg | 600 |
| catgtgcgcc | gcggcgatta | tgtgcatgtg | atgccgaaag | tgtggaaagg | cgtggtggcg | 660 |
| gatcgccgct | atctgcagca | ggcgctggat | tggtttcgcg | cgcgctatag | cagcctgatt | 720 |
| tttgtggtga | ccagcaacgg | catggcgtgg | tgccgcgaaa | acattgatac | cagccatggc | 780 |
| gatgtggtgt | ttgcgggcga | tgcattgaa | ggcagcccgg | cgaaagattt | tgcgctgctg | 840 |
| acccagtgca | accataccat | tatgaccatt | ggcacctttg | catttgggc | ggcgtatctg | 900 |
| accggcggcg | ataccattta | tctggcgaac | tataccctgc | cggatagccc | gtttctgaaa | 960 |
| attttaaac | cggaagcggc | gtttctgccg | aatggaccg | gcattgcggc | ggatctgagc | 1020 |
| ccgctgctga | acattaaga | attc | | | | 1044 |

<210> SEQ ID NO 5
<211> LENGTH: 361
<212> TYPE: PRT
<213> ORGANISM: human

<400> SEQUENCE: 5

Met Asp Pro Leu Gly Ala Ala Lys Pro Gln Trp Pro Trp Arg Arg Ser
1               5                   10                  15

Leu Ala Ala Leu Leu Phe Gln Leu Leu Val Ala Val Cys Phe Phe Ser
                20                  25                  30

Tyr Leu Arg Val Ser Arg Asp Asp Ala Thr Gly Ser Pro Arg Ala Pro
            35                  40                  45

Ser Gly Ser Ser Arg Gln Asp Thr Thr Pro Thr Arg Pro Thr Leu Leu
        50                  55                  60

Ile Leu Leu Arg Thr Trp Pro Phe His Ile Pro Val Ala Leu Ser Arg
65                  70                  75                  80

Cys Ser Glu Met Val Pro Gly Thr Ala Asp Cys His Ile Thr Ala Asp
                85                  90                  95

```
Arg Lys Val Tyr Pro Gln Ala Asp Met Val Ile Val His His Trp Asp
                100                 105                 110
Ile Met Ser Asn Pro Lys Ser Arg Leu Pro Ser Pro Arg Pro Gln
            115                 120                 125
Gly Gln Arg Trp Ile Trp Phe Asn Leu Glu Pro Pro Asn Cys Gln
        130                 135                 140
His Leu Glu Ala Leu Asp Arg Tyr Phe Asn Leu Thr Met Ser Tyr Arg
145                 150                 155                 160
Ser Asp Ser Asp Ile Phe Thr Pro Tyr Gly Trp Leu Glu Pro Trp Ser
                165                 170                 175
Gly Gln Pro Ala His Pro Pro Leu Asn Leu Ser Ala Lys Thr Glu Leu
            180                 185                 190
Val Ala Trp Ala Val Ser Asn Trp Lys Pro Asp Ser Ala Arg Val Arg
        195                 200                 205
Tyr Tyr Gln Ser Leu Gln Ala His Leu Lys Val Asp Val Tyr Gly Arg
        210                 215                 220
Ser His Lys Pro Leu Pro Lys Gly Thr Met Met Glu Thr Leu Ser Arg
225                 230                 235                 240
Tyr Lys Phe Tyr Leu Ala Phe Glu Asn Ser Leu His Pro Asp Tyr Ile
                245                 250                 255
Thr Glu Lys Leu Trp Arg Asn Ala Leu Glu Ala Trp Ala Val Pro Val
            260                 265                 270
Val Leu Gly Pro Ser Arg Ser Asn Tyr Glu Arg Phe Leu Pro Pro Asp
        275                 280                 285
Ala Phe Ile His Val Asp Asp Phe Gln Ser Pro Lys Asp Leu Ala Arg
        290                 295                 300
Tyr Leu Gln Glu Leu Asp Lys Asp His Ala Arg Tyr Leu Ser Tyr Phe
305                 310                 315                 320
Arg Trp Arg Glu Thr Leu Arg Pro Arg Ser Phe Ser Trp Ala Leu Asp
                325                 330                 335
Phe Cys Lys Ala Cys Trp Lys Leu Gln Gln Glu Ser Arg Tyr Gln Thr
            340                 345                 350
Val Arg Ser Ile Ala Ala Trp Phe Thr
        355                 360

<210> SEQ ID NO 6
<211> LENGTH: 1100
<212> TYPE: DNA
<213> ORGANISM: human

<400> SEQUENCE: 6
tctagaatgg atccgctggg cgcggcgaaa ccgcagtggc cgtggcgccg cagcctggcg      60
gcgctgctgt ttcagctgct ggtggcggtg tgcttttta gctatctgcg cgtgagccgc     120
gatgatgcga ccggcagccc gcgcgcgccg agcggcagca gccgccagga taccaccccg     180
acccgcccga ccctgctgat tctgctgcgc acctggccgt tcatattcc ggtggcgctg     240 agccgctgca gcgaaatggt gccgggcacc gcggattgcc atattaccgc ggatcgcaaa     300
gtgtatccgc aggcggatat ggtgattgtg catcattggg atattatgag caacccgaaa     360
agccgcctgc cgccgagccc gcgcccgcag ggccagcgct ggatttggtt taacctggaa     420
ccgccgccga actgccagca tctggaagcg ctggatcgct attttaacct gaccatgagc     480
tatcgcagcg atagcgatat ttttaccccg tatggctggc tggaaccgtg gagcggccag     540
ccggcgcatc cgccgctgaa cctgagcgcg aaaaccgaac tggtggcgtg ggcggtgagc     600
```

```
aactggaaac cggatagcgc gcgcgtgcgc tattatcaga gcctgcaggc gcatctgaaa    660
gtggatgtgt atggccgcag ccataaaccg ctgccgaaag caccatgat ggaaaccctg     720 agccgctata atttatct ggcgtttgaa acagcctgc atccggatta tattaccgaa       780
aaactgtggc gcaacgcgct ggaagcgtgg gcggtgccgg tggtgctggg cccgagccgc    840
agcaactatg aacgctttct gccgccggat gcgtttattc atgtggatga ttttcagagc    900
ccgaaagatc tggcgcgcta tctgcaggaa ctggataaag atcatgcgcg ctatctgagc    960
tattttcgct ggcgcgaaac cctgcgcccg cgcagcttta gctgggcgct ggattttgc   1020 aaagcgtgct ggaaactgca gcaggaaagc cgctatcaga ccgtgcgcag cattgcggcg   1080
tggtttacct aagcggccgc                                              1100

<210> SEQ ID NO 7
<211> LENGTH: 326
<212> TYPE: PRT
<213> ORGANISM: human

<400> SEQUENCE: 7

Met Ala Ser Lys Val Ser Cys Leu Tyr Val Leu Thr Val Val Cys Trp
1               5                   10                  15

Ala Ser Ala Leu Trp Tyr Leu Ser Ile Thr Arg Pro Thr Ser Ser Tyr
            20                  25                  30

Thr Gly Ser Lys Pro Phe Ser His Leu Thr Val Ala Arg Lys Asn Phe
        35                  40                  45

Thr Phe Gly Asn Ile Arg Thr Arg Pro Ile Asn Pro His Ser Phe Glu
    50                  55                  60

Phe Leu Ile Asn Glu Pro Asn Lys Cys Glu Lys Asn Ile Pro Phe Leu
65                  70                  75                  80

Val Ile Leu Ile Ser Thr Thr His Lys Glu Phe Asp Ala Arg Gln Ala
                85                  90                  95

Ile Arg Glu Thr Trp Gly Asp Glu Asn Asn Phe Lys Gly Ile Lys Ile
            100                 105                 110

Ala Thr Leu Phe Leu Leu Gly Lys Asn Ala Asp Pro Val Leu Asn Gln
        115                 120                 125

Met Val Glu Gln Glu Ser Gln Ile Phe His Asp Ile Val Glu Asp
    130                 135                 140

Phe Ile Asp Ser Tyr His Asn Leu Thr Leu Lys Thr Leu Met Gly Met
145                 150                 155                 160

Arg Trp Val Ala Thr Phe Cys Ser Lys Ala Lys Tyr Val Met Lys Thr
                165                 170                 175

Asp Ser Asp Ile Phe Val Asn Met Asp Asn Leu Ile Tyr Lys Leu Leu
            180                 185                 190

Lys Pro Ser Thr Lys Pro Arg Arg Arg Tyr Phe Thr Gly Tyr Val Ile
        195                 200                 205

Asn Gly Gly Pro Ile Arg Asp Val Arg Ser Lys Trp Tyr Met Pro Arg
    210                 215                 220

Asp Leu Tyr Pro Asp Ser Asn Tyr Pro Pro Phe Cys Ser Gly Thr Gly
225                 230                 235                 240

Tyr Ile Phe Ser Ala Asp Val Ala Glu Leu Ile Tyr Lys Thr Ser Leu
                245                 250                 255

His Thr Arg Leu Leu His Leu Glu Asp Val Tyr Val Gly Leu Cys Leu
            260                 265                 270

Arg Lys Leu Gly Ile His Pro Phe Gln Asn Ser Gly Phe Asn His Trp
```

```
            275                 280                 285
Lys Met Ala Tyr Ser Leu Cys Arg Tyr Arg Val Ile Thr Val His
    290                 295                 300

Gln Ile Ser Pro Glu Glu Met His Arg Ile Trp Asn Asp Met Ser Ser
305                 310                 315                 320

Lys Lys His Leu Arg Cys
            325

<210> SEQ ID NO 8
<211> LENGTH: 1005
<212> TYPE: DNA
<213> ORGANISM: human

<400> SEQUENCE: 8
cccccgctag catggccagc aaggtgagct gcctgtacgt gctgaccgtg gtgtgctggg      60
ccagcgccct gtggtacctg agcatcacca gacccaccag cagctacacc ggcagcaagc     120
ccttcagcca cctgaccgtg gccagaaaga acttcacctt cggcaacatc agaaccagac     180
ccatcaaccc ccacagcttc gagttcctga tcaacgagcc aacaagtgc gagaagaaca      240 tccccttcct ggtgatcctg atcagcacca cccacaagga gttcgacgcc agacaggcca     300
tcagagagac ctggggcgac gagaacaact tcaagggcat caagatcgcc accctgttcc     360
tgctgggcaa gaacgccgac cccgtgctga accagatggt ggagcaggag agccagatct     420
tccacgacat catcgtggag gacttcatcg acagctacca aacctgacc ctgaagaccc      480 tgatgggcat gagatgggtg ccaccttct gcagcaaggc caagtacgtg atgaagaccg      540
acagcgacat cttcgtgaac atggacaacc tgatctacaa gctgctgaag cccagcacca     600
agcccagaag aagatacttc accggctacg tgatcaacgg cggccccatc agagacgtga     660
gaagcaagtg gtacatgccc agagacctgt accccgacag caactacccc ccttctgca      720 gcggcaccgg ctacatcttc agcgccgacg tggccgagct gatctacaag accagcctgc     780
acaccagact gctgcacctg gaggacgtgt acgtgggcct gtgcctgaga aagctgggca     840
tccacccctt ccagaacagc ggcttcaacc actggaagat ggcctacagc ctgtgcagat     900
acagaagagt gatcaccgtg caccagatca gccccgagga gatgcacaga atctggaacg     960
acatgagcag caagaagcac ctgagatgct gagcggccgc ccccc                    1005

<210> SEQ ID NO 9
<211> LENGTH: 308
<212> TYPE: PRT
<213> ORGANISM: human

<400> SEQUENCE: 9

Met Ala His Met Lys Thr Arg Leu Val Tyr Ala Ser Ile Leu Met Met
1               5                   10                  15

Gly Ala Leu Cys Leu Tyr Phe Ser Met Asp Ser Phe Arg Glu Leu Pro
            20                  25                  30

Phe Val Phe Lys Lys Ser His Gly Lys Phe Leu Gln Ile Pro Asp Ile
        35                  40                  45

Asp Cys Lys Gln Lys Pro Pro Phe Leu Val Leu Val Thr Ser Ser
    50                  55                  60

His Lys Gln Leu Ala Ala Arg Met Ala Ile Arg Lys Thr Trp Gly Arg
65                  70                  75                  80

Glu Thr Ser Val Gln Gly Gln Gln Val Arg Thr Phe Phe Leu Leu Gly
                85                  90                  95
```

```
Thr Ser Asp Ser Thr Glu Glu Met Asp Ala Thr Leu Glu Ser Glu
            100                 105                 110

Gln His Arg Asp Ile Ile Gln Lys Asp Phe Lys Asp Ala Tyr Phe Asn
        115                 120                 125

Leu Thr Leu Lys Thr Met Met Gly Met Glu Trp Val Tyr His Phe Cys
130                 135                 140

Pro Gln Thr Ala Tyr Val Met Lys Thr Asp Ser Asp Met Phe Val Asn
145                 150                 155                 160

Val Gly Tyr Leu Thr Glu Leu Leu Leu Lys Asn Lys Thr Thr Arg
                165                 170                 175

Phe Phe Thr Gly Tyr Ile Lys Pro His Asp Phe Pro Ile Arg Gln Lys
            180                 185                 190

Phe Asn Lys Trp Phe Val Ser Lys Phe Glu Tyr Pro Trp Asp Arg Tyr
        195                 200                 205

Pro Pro Phe Cys Ser Gly Thr Gly Tyr Val Phe Ser Ser Asp Val Ala
210                 215                 220

Ile Gln Val Tyr Asn Val Ser Glu Ser Val Pro Phe Ile Lys Leu Glu
225                 230                 235                 240

Asp Val Phe Val Gly Leu Cys Leu Ala Lys Leu Lys Ile Arg Pro Glu
                245                 250                 255

Glu Leu His Thr Lys Gln Thr Phe Phe Pro Gly Gly Leu Arg Phe Ser
            260                 265                 270

Val Cys Arg Phe Gln Lys Ile Val Ala Cys His Phe Met Lys Pro Gln
        275                 280                 285

Asp Leu Leu Thr Tyr Trp Gln Ala Leu Glu Asn Ser Lys Glu Gln Asp
290                 295                 300

Cys Pro Ala Val
305

<210> SEQ ID NO 10
<211> LENGTH: 951
<212> TYPE: DNA
<213> ORGANISM: human

<400> SEQUENCE: 10
cccccgctag catggcccac atgaagacca gactggtgta cgccagcatc ctgatgatgg      60
gcgccctgtg cctgtacttc agcatggaca gcttcagaga gctgcccttc gtgttcaaga     120
agagccacgg caagttcctg cagatccccg acatcgactg caagcagaag ccccccttcc     180
tggtgctgct ggtgaccagc agccacaagc agctggccgc cagaatggcc atcagaaaga     240
cctggggcag agagaccagc gtgcagggcc agcaggtgag aaccttcttc ctgctgggca     300
ccagcgacag caccgaggag atggacgcca ccaccctgga gagcgagcag cacagagaca     360
tcatccagaa ggacttcaag gacgcctact tcaacctgac cctgaagacc atgatgggca     420
tggagtgggt gtaccacttc tgcccccaga ccgcctacgt gatgaagacc gacagcgaca     480
tgttcgtgaa cgtgggctac ctgaccgagc tgctgctgaa gaacaagacc accagat       540 tcttcaccgg ctacatcaag ccccacgact tccccatcag acagaagttc aacaagtggt     600
tcgtgagcaa gttcgagtac cctgggacag atacccccc cttctgcagc ggcaccggct     660
acgtgttcag cagcgacgtg gccatccagg tgtacaacgt gagcgagagc gtgcccttca     720
tcaagctgga ggacgtgttc gtgggcctgt gcctggccaa gctgaagatc agacccgagg     780
agctgcacac caagcagacc ttcttccccg gcggcctgag attcagcgtg tgcagattcc     840
agaagatcgt ggcctgccac ttcatgaagc cccaggacct gctgacctac tggcaggccc     900
```
tggagaacag caaggagcag gactgccccg ccgtgtgagc ggccgccccc c    951

<210> SEQ ID NO 11
<211> LENGTH: 397
<212> TYPE: PRT
<213> ORGANISM: human

<400> SEQUENCE: 11

Met Ser Val Gly Arg Arg Val Lys Leu Leu Gly Ile Leu Met Met
1               5                   10                  15

Ala Asn Val Phe Ile Tyr Leu Ile Val Glu Val Ser Lys Asn Ser Ser
            20                  25                  30

Gln Asp Lys Asn Gly Lys Gly Val Ile Ile Pro Lys Glu Lys Phe
            35                  40                  45

Trp Lys Pro Pro Ser Thr Pro Arg Ala Tyr Trp Asn Arg Glu Gln Glu
    50                  55                  60

Lys Leu Asn Arg Trp Tyr Asn Pro Ile Leu Asn Arg Val Ala Asn Gln
65              70                  75                  80

Thr Gly Glu Leu Ala Thr Ser Pro Asn Thr Ser His Leu Ser Tyr Cys
                85                  90                  95

Glu Pro Asp Ser Thr Val Met Thr Ala Val Thr Asp Phe Asn Asn Leu
            100                 105                 110

Pro Asp Arg Phe Lys Asp Phe Leu Leu Tyr Leu Arg Cys Arg Asn Tyr
            115                 120                 125

Ser Leu Leu Ile Asp Gln Pro Lys Lys Cys Ala Lys Lys Pro Phe Leu
    130                 135                 140

Leu Leu Ala Ile Lys Ser Leu Ile Pro His Phe Ala Arg Arg Gln Ala
145                 150                 155                 160

Ile Arg Glu Ser Trp Gly Arg Glu Thr Asn Val Gly Asn Gln Thr Val
                165                 170                 175

Val Arg Val Phe Leu Leu Gly Lys Thr Pro Pro Glu Asp Asn His Pro
            180                 185                 190

Asp Leu Ser Asp Met Leu Lys Phe Glu Ser Asp Lys His Gln Asp Ile
            195                 200                 205

Leu Met Trp Asn Tyr Arg Asp Thr Phe Phe Asn Leu Ser Leu Lys Glu
    210                 215                 220

Val Leu Phe Leu Arg Trp Val Ser Thr Ser Cys Pro Asp Ala Glu Phe
225                 230                 235                 240

Val Phe Lys Gly Asp Asp Asp Val Phe Val Asn Thr His His Ile Leu
            245                 250                 255

Asn Tyr Leu Asn Ser Leu Ser Lys Ser Lys Ala Lys Asp Leu Phe Ile
            260                 265                 270

Gly Asp Val Ile His Asn Ala Gly Pro His Arg Asp Lys Lys Leu Lys
            275                 280                 285

Tyr Tyr Ile Pro Glu Val Phe Tyr Thr Gly Val Tyr Pro Pro Tyr Ala
    290                 295                 300

Gly Gly Gly Gly Phe Leu Tyr Ser Gly Pro Leu Ala Leu Arg Leu Tyr
305                 310                 315                 320

Ser Ala Thr Ser Arg Val His Leu Tyr Pro Ile Asp Asp Val Tyr Thr
                325                 330                 335

Gly Met Cys Leu Gln Lys Leu Gly Leu Val Pro Glu Lys His Lys Gly
            340                 345                 350

Phe Arg Thr Phe Asp Ile Glu Glu Lys Asn Lys Lys Asn Ile Cys Ser
            355                 360                 365

Tyr Ile Asp Leu Met Leu Val His Ser Arg Lys Pro Gln Glu Met Ile
        370                 375                 380

Asp Ile Trp Ser Gln Leu Gln Ser Pro Asn Leu Lys Cys
385                 390                 395

<210> SEQ ID NO 12
<211> LENGTH: 1218
<212> TYPE: DNA
<213> ORGANISM: human

<400> SEQUENCE: 12

| | | | | | |
|---|---|---|---|---|---|
| cccccgctag | catgagcgtg | ggcagaagaa | gagtgaagct | gctgggcatc | ctgatgatgg | 60 |
| ccaacgtgtt | catctacctg | atcgtggagg | tgagcaagaa | cagcagccag | acaagaacg | 120 |
| gcaagggcgg | cgtgatcatc | cccaaggaga | agttctggaa | gccccccagc | acccccagag | 180 |
| cctactggaa | cagagagcag | gagaagctga | acagatggta | caacccccatc | ctgaacagag | 240 |
| tggccaacca | gaccggcgag | ctggccacca | gccccaacac | cagccacctg | agctactgcg | 300 |
| agcccgacag | caccgtgatg | accgccgtga | ccgacttcaa | caacctgccc | gacagattca | 360 |
| aggacttcct | gctgtacctg | agatgcagaa | actacagcct | gctgatcgac | agcccaaga | 420 |
| agtgcgccaa | gaagcccttc | ctgctgctgg | ccatcaagag | cctgatcccc | cacttcgcca | 480 |
| gaagacaggc | catcagagag | agctggggca | gagagaccaa | cgtgggcaac | agaccgtgg | 540 |
| tgagagtgtt | cctgctgggc | aagaccccc | ccgaggacaa | ccaccccgac | ctgagcgaca | 600 |
| tgctgaagtt | cgagagcgac | aagcaccagg | acatcctgat | gtggaactac | agagacacct | 660 |
| tcttcaacct | gagcctgaag | gaggtgctgt | tcctgagatg | ggtgagcacc | agctgccccg | 720 |
| acgccgagtt | cgtgttcaag | ggcgacgacg | acgtgttcgt | gaacacccac | acatcctga | 780 |
| actacctgaa | cagcctgagc | aagagcaagg | ccaaggacct | gttcatcggc | gacgtgatcc | 840 |
| acaacgccgg | cccccacaga | gacaagaagc | tgaagtacta | catccccgag | gtgttctaca | 900 |
| ccggcgtgta | ccccccctac | gccggcggcg | gcggcttcct | gtacagcggc | ccctggccc | 960 |
| tgagactgta | cagcgccacc | agcagagtgc | acctgtaccc | catcgacgac | gtgtacaccg | 1020 |
| gcatgtgcct | gcagaagctg | ggcctggtgc | ccgagaagca | caagggcttc | agaaccttcg | 1080 |
| acatcgagga | gaagaacaag | aagaacatct | gcagctacat | cgacctgatg | ctggtgcaca | 1140 |
| gcagaaagcc | ccaggagatg | atcgacatct | ggagccagct | gcagagcccc | aacctgaagt | 1200 |
| gctgagcggc | cgcccccc | | | | | 1218 |

<210> SEQ ID NO 13
<211> LENGTH: 479
<212> TYPE: PRT
<213> ORGANISM: Artificial sequence
<220> FEATURE:
<223> OTHER INFORMATION: chimeric protein

<400> SEQUENCE: 13

Met Gly Trp Ser Trp Ile Phe Leu Phe Leu Leu Ser Gly Thr Ala Gly
1               5                   10                  15

Val Leu Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Arg Gly Leu
    50                  55                  60

-continued

```
Glu Trp Ile Gly Arg Ile Asp Pro Asn Ser Gly Thr Lys Tyr Asn
 65                  70                  75                  80

Glu Lys Phe Lys Ser Lys Ala Thr Leu Thr Val Asp Lys Pro Ser Ser
                 85                  90                  95

Thr Ala Tyr Met Gln Leu Ser Ser Leu Thr Ser Glu Asp Ser Ala Val
            100                 105                 110

Tyr Tyr Cys Ala Arg Tyr Asp Tyr Tyr Gly Ser Ser Tyr Phe Asp Tyr
        115                 120                 125

Trp Gly Gln Gly Thr Thr Val Thr Val Ser Ser Ala Ser Pro Thr Ser
    130                 135                 140

Pro Lys Val Phe Pro Leu Ser Leu Asp Ser Thr Pro Gln Asp Gly Asn
145                 150                 155                 160

Val Val Val Ala Cys Leu Val Gln Gly Phe Phe Pro Gln Glu Pro Leu
                165                 170                 175

Ser Val Thr Trp Ser Glu Ser Gly Gln Asn Val Thr Ala Arg Asn Phe
            180                 185                 190

Pro Pro Ser Gln Asp Ala Ser Gly Asp Leu Tyr Thr Thr Ser Ser Gln
        195                 200                 205

Leu Thr Leu Pro Ala Thr Gln Cys Pro Asp Gly Lys Ser Val Thr Cys
    210                 215                 220

His Val Lys His Tyr Thr Asn Pro Ser Gln Asp Val Thr Val Pro Cys
225                 230                 235                 240

Pro Val Pro Pro Pro Pro Cys Cys His Pro Arg Leu Ser Leu His
                245                 250                 255

Arg Pro Ala Leu Glu Asp Leu Leu Leu Gly Ser Glu Ala Asn Leu Thr
            260                 265                 270

Cys Thr Leu Thr Gly Leu Arg Asp Ala Ser Gly Ala Thr Phe Thr Trp
        275                 280                 285

Thr Pro Ser Ser Gly Lys Ser Ala Val Gln Gly Pro Pro Glu Arg Asp
    290                 295                 300

Leu Cys Gly Cys Tyr Ser Val Ser Ser Val Leu Pro Gly Cys Ala Gln
305                 310                 315                 320

Pro Trp Asn His Gly Glu Thr Phe Thr Cys Thr Ala Ala His Pro Glu
                325                 330                 335

Leu Lys Thr Pro Leu Thr Ala Asn Ile Thr Lys Ser Gly Asn Thr Phe
            340                 345                 350

Arg Pro Glu Val His Leu Leu Pro Pro Ser Glu Glu Leu Ala Leu
        355                 360                 365

Asn Glu Leu Val Thr Leu Thr Cys Leu Ala Arg Gly Phe Ser Pro Lys
370                 375                 380

Asp Val Leu Val Arg Trp Leu Gln Gly Ser Gln Glu Leu Pro Arg Glu
385                 390                 395                 400

Lys Tyr Leu Thr Trp Ala Ser Arg Gln Glu Pro Ser Gln Gly Thr Thr
                405                 410                 415

Thr Phe Ala Val Thr Ser Ile Leu Arg Val Ala Ala Glu Asp Trp Lys
            420                 425                 430

Lys Gly Asp Thr Phe Ser Cys Met Val Gly His Glu Ala Leu Pro Leu
        435                 440                 445

Ala Phe Thr Gln Lys Thr Ile Asp Arg Leu Ala Gly Lys Pro Thr His
    450                 455                 460

Val Asn Val Ser Val Val Met Ala Glu Val Asp Gly Thr Cys Tyr
465                 470                 475
```

<210> SEQ ID NO 14
<211> LENGTH: 1460
<212> TYPE: DNA
<213> ORGANISM: Artificial sequence
<220> FEATURE:
<223> OTHER INFORMATION: chimeric DNA

<400> SEQUENCE: 14

```
ccccaagctt atgggctgga gctggatctt cctgttcctg ctgagcggca ccgccggcgt      60
gctgagccag gtgcagctgc agcagcccgg cgccgagctg gtgaagcccg gcgccagcgt     120
gaagctgagc tgcaaggcca gcggctacac cttcaccagc tactggatgc actgggtgaa     180
gcagagaccc ggcagaggcc tggagtggat cggcagaatc gaccccaaca cgcggcggca     240
caagtacaac gagaagttca gagcaaggc caccctgacc gtggacaagc ccagcagcac     300
cgcctacatg cagctgagca gcctgaccag cgaggacagc gccgtgtact actgcgccag     360
atacgactac tacggcagca gctacttcga ctactggggc cagggcacca ccgtgaccgt     420
gagcagcgcc agccccacca gcccaaggt gttcccctg agcctggaca gccccccca     480
ggacggcaac gtggtggtgg cctgcctggt gcagggcttc ttccccagg agccctgag     540
cgtgacctgg agcgagagcg ccagaacgt gaccgccaga acttccccc ccagccagga     600
cgccagcggc gacctgtaca ccaccagcag ccagctgacc ctgcccgcca cccagtgccc     660
cgacggcaag agcgtgacct gccacgtgaa gcactacacc aaccccagcc aggacgtgac     720
cgtgccctgc cccgtgcccc cccccccc ctgctgccac cccagactga gcctgcacag     780
acccgccctg gaggacctgc tgctgggcag cgaggccaac ctgacctgca ccctgaccgg     840
cctgagagac gccagcggcg ccaccttcac ctggaccccc agcagcggca gagcgccgt     900
gcagggcccc ccgagagag acctgtgcgg ctgctacagc gtgagcagcg tgctgccgg     960
ctgcgcccag ccctggaacc acggcgagac cttcacctgc accgccgccc accccgagct    1020
gaagaccccc ctgaccgcca acatcaccaa gagcggcaac accttcagac ccgaggtgca    1080
cctgctgccc ccccccagcg aggagctggc cctgaacgag ctggtgaccc tgacctgcct    1140
ggccagaggc ttcagcccca aggacgtgct ggtgagatgg ctgcagggca gccaggagct    1200
gcccagagag aagtacctga cctgggccag cagacaggag cccagccagg caccaccac    1260
cttcgccgtg accagcatcc tgagagtggc cgccgaggac tggaagaagg gcgacacctt    1320
cagctgcatg gtgggccacg aggccctgcc cctggccttc acccagaaga ccatcgacag    1380
actggccggc aagcccaccc acgtgaacgt gagcgtggtg atggccgagg tggacggcac    1440
ctgctactga tctagacccc                                                1460
```

<210> SEQ ID NO 15
<211> LENGTH: 4
<212> TYPE: PRT
<213> ORGANISM: Artificial sequence
<220> FEATURE:
<223> OTHER INFORMATION: Sequence motif
<220> FEATURE:
<221> NAME/KEY: MISC_FEATURE
<222> LOCATION: (2)..(2)
<223> OTHER INFORMATION: X is any amino acid but Proline
<220> FEATURE:
<221> NAME/KEY: MISC_FEATURE
<222> LOCATION: (4)..(4)
<223> OTHER INFORMATION: X is any amino acid but Proline

<400> SEQUENCE: 15

Asn Xaa Thr Xaa
1

<210> SEQ ID NO 16
<211> LENGTH: 4
<212> TYPE: PRT
<213> ORGANISM: Artificial sequence
<220> FEATURE:
<223> OTHER INFORMATION: Sequence motif
<220> FEATURE:
<221> NAME/KEY: MISC_FEATURE
<222> LOCATION: (2)..(2)
<223> OTHER INFORMATION: X is any amino acid but Proline
<220> FEATURE:
<221> NAME/KEY: MISC_FEATURE
<222> LOCATION: (4)..(4)
<223> OTHER INFORMATION: X is any amino acid but Proline

<400> SEQUENCE: 16

Asn Xaa Ser Xaa
1

<210> SEQ ID NO 17
<211> LENGTH: 631
<212> TYPE: PRT
<213> ORGANISM: goat

<400> SEQUENCE: 17

Met Ser Arg Leu Phe Leu Ala Cys Leu Leu Ala Val Phe Pro Val Val
1               5                   10                  15

Ser Met Lys Ser Pro Ile Phe Gly Pro Lys Glu Val Thr Ser Val Glu
            20                  25                  30

Gly Arg Ser Val Ser Ile Thr Cys Tyr Tyr Pro Ala Thr Ser Val Asn
        35                  40                  45

Arg His Thr Arg Lys Tyr Trp Cys Arg Gln Gly Ala Thr Gly Arg Cys
    50                  55                  60

Thr Thr Leu Ile Ser Ser Glu Gly Tyr Val Ser Asp Asp Tyr Val Gly
65              70                  75                  80

Arg Ala Asn Leu Thr Asn Phe Pro Glu Ser Gly Thr Phe Val Val Asp
                85                  90                  95

Ile Ser His Leu Thr Arg Asn Asp Ser Gly Arg Tyr Lys Cys Gly Leu
            100                 105                 110

Gly Ile Ser Ser Arg Gly Leu Asn Phe Asp Val Ser Leu Glu Val Ser
        115                 120                 125

Gln Asp Pro Ala Gln Ala Ser Asp Ala His Ile Tyr Pro Val Asp Val
    130                 135                 140

Gly Arg Thr Val Thr Ile Asn Cys Pro Phe Thr Ser Ala Asn Ser Gln
145                 150                 155                 160

Lys Arg Lys Ser Leu Cys Lys Lys Thr Gly Gln Gly Cys Phe Leu Ile
                165                 170                 175

Ile Asp Ser Thr Gly Tyr Lys Asn Glu Asn Tyr Glu Asp Arg Ile Arg
            180                 185                 190

Leu Asn Ile Ala Gly Thr Asp Thr Leu Val Phe Ser Val Val Ile Asn
        195                 200                 205

Arg Val Leu Leu Ser Asp Ala Gly Thr Tyr Val Cys Gln Ala Gly Asp
    210                 215                 220

Asp Ala Lys Ala Asp Lys Ser Asn Val Tyr Leu Gln Val Leu Glu Pro
225                 230                 235                 240

Glu Pro Glu Leu Val Tyr Arg Asp Leu Arg Ser Ser Val Thr Phe Asp
                245                 250                 255

Cys Ser Leu Gly Pro Glu Val Ala Asn Thr Ala Lys Phe Leu Cys Gln

```
                    260                 265                 270
Gln Lys Asn Gly Glu Ala Cys Asn Val Val Ile Asn Thr Leu Gly Lys
                275                 280                 285

Lys Ala Gln Asp Phe Gln Gly Arg Ile Leu Phe Leu Pro Lys Asp Asn
            290                 295                 300

Gly Val Phe Ser Val His Ile Ala Ser Leu Arg Lys Glu Asp Ala Gly
305                 310                 315                 320

Arg Tyr Val Cys Gly Gly Gln Pro Glu Gly Gln Pro Glu Lys Gly Trp
                325                 330                 335

Pro Val Gln Ala Trp Glu Leu Phe Val Asn Glu Glu Thr Ala Ile Pro
            340                 345                 350

Ala Ser Pro Ser Val Val Lys Gly Val Lys Gly Gly Ser Val Thr Val
                355                 360                 365

Ser Cys Pro Tyr Asn Pro Lys Asp Ala Asn Ser Ala Lys Tyr Trp Cys
            370                 375                 380

Arg Trp Glu Glu Ala Gln Asn Gly Arg Cys Pro Arg Leu Val Gln Ser
385                 390                 395                 400

Lys Gly Leu Val Lys Glu Gln Tyr Lys Gly Arg Leu Ala Leu Leu Ala
                405                 410                 415

Gln Pro Gly Asn Gly Thr Tyr Thr Val Ile Leu Asn Gln Leu Thr Asp
            420                 425                 430

Gln Asp Ala Gly Phe Tyr Trp Cys Val Thr Asp Gly Asp Thr Ser Trp
                435                 440                 445

Thr Ser Thr Val Gln Leu Lys Val Val Glu Gly Glu Pro Ser Leu Lys
450                 455                 460

Val Pro Lys Asn Val Thr Ala Trp Leu Gly Glu Ala Phe Lys Leu Ser
465                 470                 475                 480

Cys His Phe Pro Cys Lys Phe Tyr Ser Phe Glu Lys Tyr Trp Cys Lys
                485                 490                 495

Trp Ser Asn Glu Gly Cys Ser Pro Leu Pro Thr Gln Asn Asp Gly Pro
            500                 505                 510

Ser Gln Ala Phe Val Ser Cys Asp Gln Asn Ser Gln Ile Val Ser Leu
                515                 520                 525

Asn Leu Asp Thr Val Thr Lys Glu Asp Glu Gly Trp Tyr Trp Cys Gly
            530                 535                 540

Val Lys Glu Gly Pro Arg Tyr Gly Glu Thr Ala Ala Val Tyr Val Ala
545                 550                 555                 560

Val Glu Ser Arg Ala Lys Gly Ser Gln Asp Ala Lys Gln Val Asn Ala
                565                 570                 575

Ala Pro Ala Gly Gly Ala Ile Glu Ser Arg Ala Gly Glu Ile Gln Asn
            580                 585                 590

Lys Ala Leu Leu Asp Pro Arg Leu Phe Val Glu Ile Ala Val Lys
                595                 600                 605

Asp Ala Ala Gly Gly Pro Gly Ala Pro Ala Asp Pro Gly Arg Pro Ala
            610                 615                 620

Gly His Ser Gly Ser Ser Lys
625                 630

<210> SEQ ID NO 18
<211> LENGTH: 8
<212> TYPE: PRT
<213> ORGANISM: Artificial sequence
<220> FEATURE:
<223> OTHER INFORMATION: peptide
```

```
<400> SEQUENCE: 18

Ala Asn Leu Thr Asn Phe Pro Glu
1               5

<210> SEQ ID NO 19
<211> LENGTH: 5
<212> TYPE: PRT
<213> ORGANISM: Artificial sequence
<220> FEATURE:
<223> OTHER INFORMATION: peptide

<400> SEQUENCE: 19

Asn Asp Ser Gly Arg
1               5

<210> SEQ ID NO 20
<211> LENGTH: 44
<212> TYPE: PRT
<213> ORGANISM: Artificial sequence
<220> FEATURE:
<223> OTHER INFORMATION: peptide

<400> SEQUENCE: 20

Leu Ala Leu Leu Ala Gln Pro Gly Asn Gly Thr Tyr Thr Val Ile Leu
1               5                   10                  15

Asn Gln Leu Thr Asp Gln Asp Ala Gly Phe Tyr Trp Cys Val Thr Asp
            20                  25                  30

Gly Asp Thr Ser Trp Thr Ser Thr Val Gln Leu Lys
        35                  40

<210> SEQ ID NO 21
<211> LENGTH: 8
<212> TYPE: PRT
<213> ORGANISM: Artificial sequence
<220> FEATURE:
<223> OTHER INFORMATION: peptide

<400> SEQUENCE: 21

Asn Val Thr Ala Trp Leu Gly Glu
1               5
```